(12) United States Patent
Mahboobi et al.

(10) Patent No.: US 11,198,694 B2
(45) Date of Patent: Dec. 14, 2021

(54) HDAC6 INHIBITORS, WITH IMPROVED SOLUBILITY AND THEIR USES

(71) Applicant: UNIVERSITÄT REGENSBURG, Regensburg (DE)

(72) Inventors: Siavosh Mahboobi, Regensburg (DE); Herwig Pongratz, Regensburg (DE); Elisabeth Grünstein, Regensburg (DE)

(73) Assignee: UNIVERSITÄT REGENSBURG, Regensburg (DE)

( * ) Notice: Subject to any disclaimer, the term of this patent is extended or adjusted under 35 U.S.C. 154(b) by 0 days.

(21) Appl. No.: 16/621,003

(22) PCT Filed: Jun. 29, 2018

(86) PCT No.: PCT/EP2018/067573
§ 371 (c)(1),
(2) Date: Dec. 10, 2019

(87) PCT Pub. No.: WO2019/007836
PCT Pub. Date: Jan. 10, 2019

(65) Prior Publication Data
US 2020/0308174 A1    Oct. 1, 2020

(30) Foreign Application Priority Data
Jul. 6, 2017 (EP) .................................... 17180002

(51) Int. Cl.
*C07D 471/18* (2006.01)
*A61K 31/529* (2006.01)
*A61P 25/28* (2006.01)
*A61P 35/00* (2006.01)
*C07D 471/14* (2006.01)
*C07D 471/22* (2006.01)
*A61K 45/06* (2006.01)

(52) U.S. Cl.
CPC ............ *C07D 471/18* (2013.01); *A61P 25/28* (2018.01); *A61P 35/00* (2018.01); *C07D 471/14* (2013.01); *C07D 471/22* (2013.01); *A61K 45/06* (2013.01)

(58) Field of Classification Search
CPC .. C07D 471/18; C07D 413/14; A61K 31/529; A61K 31/5377; A61P 25/28
USPC ........................ 544/247, 115; 514/257, 233.2
See application file for complete search history.

(56) References Cited

U.S. PATENT DOCUMENTS 10,106,540 B2 * 10/2018 Mahboobi ............ C07D 471/14

FOREIGN PATENT DOCUMENTS

| CN | 105524061 A | 4/2016 |
|---|---|---|
| WO | 2011011186 A2 | 1/2011 |
| WO | 2016020369 A1 | 2/2011 |

* cited by examiner

*Primary Examiner* — Charanjit Aulakh
(74) *Attorney, Agent, or Firm* — Saliwanchik, Lloyd & Eisenschenk

(57) ABSTRACT

The present invention relates to small molecule compounds and their use as HDAC inhibitors and their use in the treatment of various diseases, such as cancer. The present invention further relates to methods for improvement of solubility by introducing basic substituents which offer the opportunity to create pharmaceutically acceptable salts. Moreover, it comprises methods of synthesizing the compounds and methods of treatment.

14 Claims, 4 Drawing Sheets

HDAC6 INHIBITORS, WITH IMPROVED SOLUBILITY AND THEIR USES

CROSS REFERENCE TO RELATED APPLICATIONS

This application is a National Stage Application of International Application Number PCT/EP2018/067573, filed Jun. 29, 2018; which claims priority to European Patent Application Number 17 180 002.2, filed Jul. 6, 2017.

The present invention relates to small molecule compounds and their use as HDAC inhibitors and their use in the treatment of various diseases, such as cancer. The present invention further relates to methods for improvement of solubility by introducing basic substituents which offer the opportunity to create pharmaceutically acceptable salts. Moreover, it comprises methods of synthesizing the compounds and methods of treatment.

BACKGROUND OF THE INVENTION

Epigenetic alterations are involved in the pathogenesis of many diseases. Histone deacetylases (HDACs) are epigenetic regulators that are frequently overexpressed in tumor cells and cause dysregulation of cell growth and differentiation. Histone deacetylase inhibitors (HDACi) are therefore considered as promising agents for tumor therapy and characterized extensively clinically and on a molecular level. HDACi inhibit the deacetylation of histones and many other proteins (Buchwald, Krämer et al. 2009; Spange, Wagner et al. 2009). As a result, HDACi modulate chromatin structure and gene expression. This further includes reexpression of tumor suppressor genes which effect differentiation, inhibition of cell growth and apoptosis. At the moment, HDACi of different drug classes are in development or in preclinical and clinical trials for cancer therapy (Schneider, Krämer et al. 2010; Quintas-Cardama, Santos et al. 2011).

HDACs can be grouped in four classes (I-IV) (Brandl, Heinzel et al. 2009; Spange, Wagner et al. 2009), whereby class I, II and IV are defined by a zinc depending mechanism. Class II HDACs can be subdivided in IIa (HDAC4, -5, -7, -9) and IIb (HDAC6, -10). Class III HDACs need NAD$^+$ as a cofactor. Whilst HDACs of class I and IV are expressed ubiquitously, they are primarily localized in the nucleus. In contrast, class II HDACs can move from the nucleus to the cytoplasm and show higher tissue specifity (Brandl, Heinzel et al. 2009; Spange, Wagner et al. 2009).

So-called pan-HDACi have a wide range of cytotoxic profile due to the inhibition of several HDAC isoforms. In contrast, isoenzyme-selective HDAC inhibitors appear to be more suitable considering the therapy and to have fewer side effects. They usually do not generate the undesired side effects which are associated with the broad inhibition of HDACs ("off-target" effects) (Pandey, Nie et al. 2007).

Several HDACi are currently in clinical trials and the HDACi SAHA and depsipeptide have been FDA approved for the treatment of cutaneous T-cell lymphomas (Müller and Krämer 2010). Nevertheless, HDACi show its full activity against cancer only in combination with other cytostatic compounds (see e.g. (Spange, Wagner et al. 2009)).

Along with the generally increasing importance of enzymes as therapy targets, HDAC6 is closely associated with the development of cancer. Whilst the expression of HDAC6 is induced by oncogenic RAS transformation and it is necessary for an efficient tumor formation. For example, HDAC6 is highly overexpressed in acute myeloid leukemia cells (AML) compared to normal cells (Lee, Lim et al. 2008).

Beneficial therapeutic effects on tumor cells have been described not only for pan-HDACi, but also for HDAC6 selective inhibitors. For example, ST80 (see FIG. 1(A), compound 1) is an HDAC6 selective inhibitor with an IC$_{50}$ value of circa 1 μM for HDAC6 and 31 times more selective against HDAC6 than against HDAC1 (Scott, Marx et al. 2008), which has the same antiproliferative effect in low micro molar range in myeloid cell lines and primary AML blasts as pan-HDACi. Thus, HDAC6 is a potential target structure of antileukemic therapy regimens.

Further, the influence of HDAC6 on the HSP-90 activity can also be important for the treatment efficiency (Chou, Inks et al. 2012). Amongst other things, HSP90 serves the folding and stabilization of oncogenic kinases, including the leukemia fusion protein BCR-ABL, mutated FLT3 (FLT3-ITD), c-KIT, AKT and c-RAF. HSP90 is also important for the stability of the pan-leukemic marker protein WT1 and for the leukemic fusion protein AML1-ETO (see e.g. (Choudhary, Kumar et al. 2009)). New and highly selective HDAC6 activity modulating compounds are necessary, in order to capture the detailed molecular mechanisms.

Tubastatin A (see FIG. 1(A), compound 2) and its derivatives are currently one the most selective HDAC6 inhibitors. The development of this compound is based on rational structure-based design (Buffer, Kalin et al. 2010). Further developments resulted in an even superior HDAC6 selective inhibitor called marbostat-100 (MARB 1) (Mahboobi, Sellmer et al. 2016) (see FIG. 1(A), compound 3).

One lack of these compounds is an in part reduced solubility, which might result in a reduced bioavailability. Moreover, the possibility for an oral application is reduced, therefore. There is a need in the art for improved HDAC inhibitors with enhanced solubility.

SUMMARY OF THE INVENTION

The present invention provides for a compound having the general formula I

Y—[CH$_2$]$_p$-Q-H-L-(HAm)  (formula I)

wherein H is a head group selected from

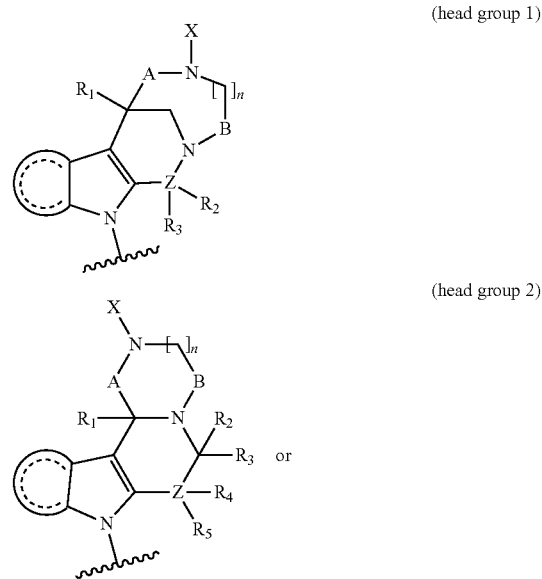

(head group 1)

(head group 2) or

-continued (head group 3)

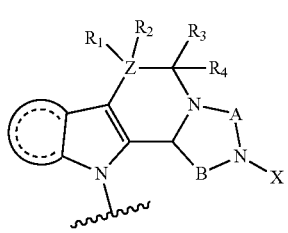

wherein L is a linker having the formula

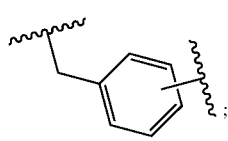

wherein (HAm) is hydroxamic acid with the formula

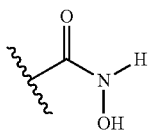

or a carbamate-protected hydroxyamic acid;
wherein A is $CH_2$, C=O or C=S;
B is $CH_2$, C=O or C=S;
n is 0 or 1;
p is 0 to 6;
Q is selected from the group comprising —$CH_2$—, O, NH, alkylamino, an ester, and an amide-group;
$R_1$ to $R_5$ are each independently selected from the group comprising hydrogen, branched or unbranched alkyl selected from $C_1$ to $C_6$, and aryl;
X is a branched or unbranched alkyl selected from $C_1$ to $C_6$;
Y is selected from the group comprising amino, alkylamino, cyclic alkylamino, dialkylamino, cyclic diaminoalkyl, such as, but not limited to, piperazinyl or 1-alkylpiperazinyl, in particular 1-methylpiperazinyl; heterocyclic alkylamino, such as, but not limited to, morpholinyl; amino acid substituents connected either via their α-amino group or their carboxy group, preferably basic amino acid substituents, such as, but not limited to, lysine, proline, histidine or arginine and pharmaceutically acceptable salts thereof, such as, but not limited to, hydrochloride, sulfate, phosphate, mesylate, tosylate or formiate or acetate;
Z is carbon, nitrogen or oxygen; with the proviso that
For headgroup 1, when Z is nitrogen, only one of R2 and R3 are present, and when Z is oxygen, none of R2 and R3 are present;
For headgroup 2, when Z is nitrogen, only one of R4 and R5 are present, and when Z is oxygen, none of R4 and R5 are present;
For headgroup 3, when Z is nitrogen, only one of R1 and R2 are present, and when Z is oxygen, none of R1 and R2 are present; and wherein the symbol

represents a five or six membered aromatic or heteroaromatic ring system, preferably a benzene-ring system;
and wherein Q is connected to said headgroup H at said

or a pharmaceutically acceptable salt thereof.

In one embodiment, at least one of A and B is C=O, preferably both are C=O.

In one embodiment, n is 0.

In one embodiment, Q is O, and p is 1-6, in particular 1, 2 or 3, preferably 2.

In one embodiment, Y is selected from the group comprising amino, alkylamino, cyclic alkylamino, dialkylamino, cyclic diaminoalkyl, such as, but not limited to, piperazinyl or 1-alkyl piperazinyl, in particular 1-methylpiperazinyl, heterocyclic alkylamino, such as, but not limited to, morpholinyl.

In one embodiment, Q is O, p is 2, and Y is morpholinyl.

In one embodiment, the hydroxyamic acid (HAm) is protected by a carbamate, such that preferably the hydroxamic acid is represented by formula

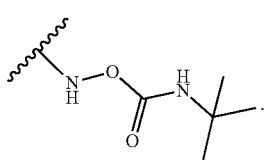 [SMILES: *NOC(=O)NC(C)(C)C]

In one embodiment, H is head group 1.
In one embodiment, H is head group 2.
In one embodiment, H is head group 3.
In one embodiment, said head group 1 is selected from the group consisting of:

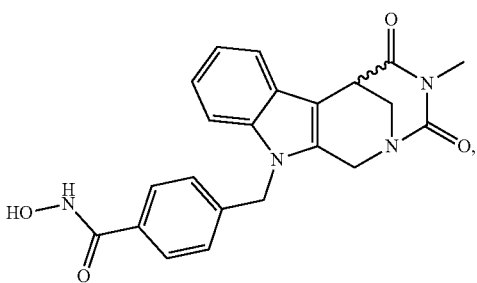

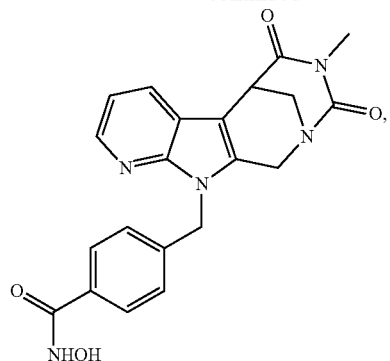
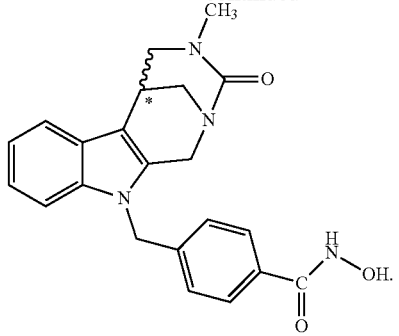
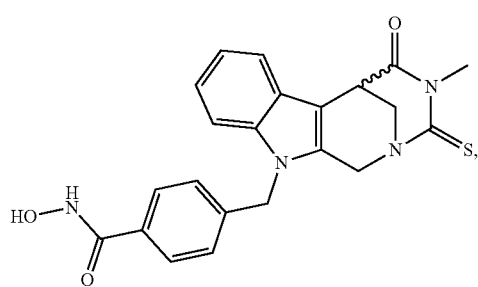
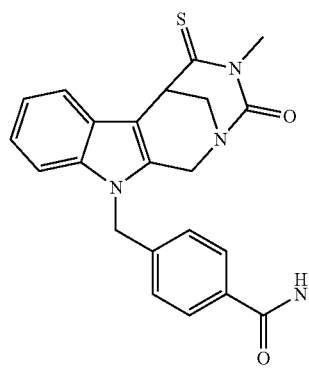
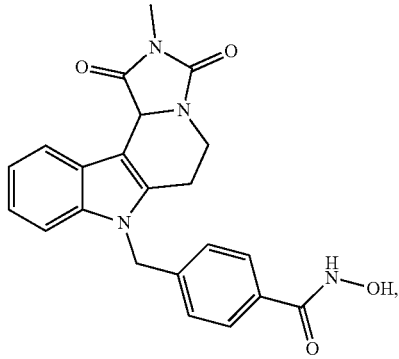
In one embodiment, said head group 2 is selected from the group consisting of
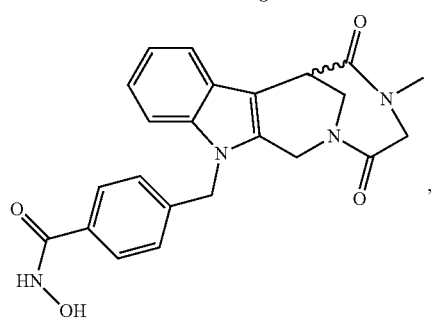
31a
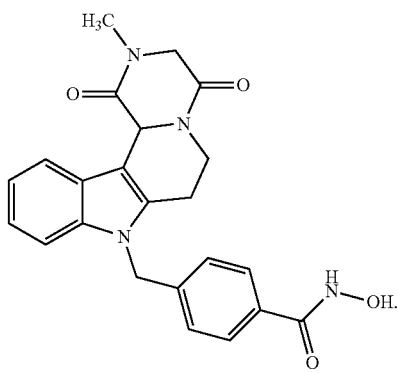
and
31b
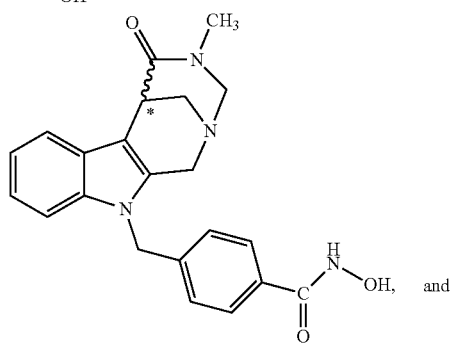
In one embodiment, said head group 3 is selected from the group consisting of
41
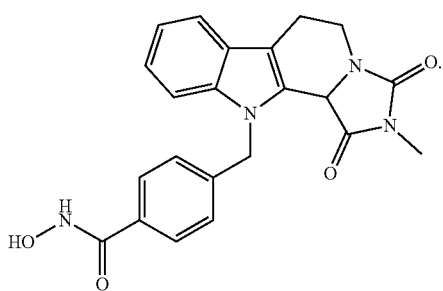

In one embodiment, said compound is selected from

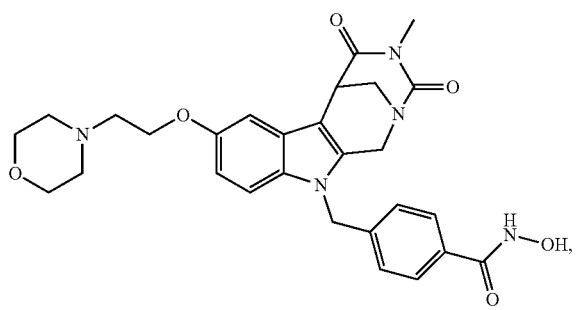

21

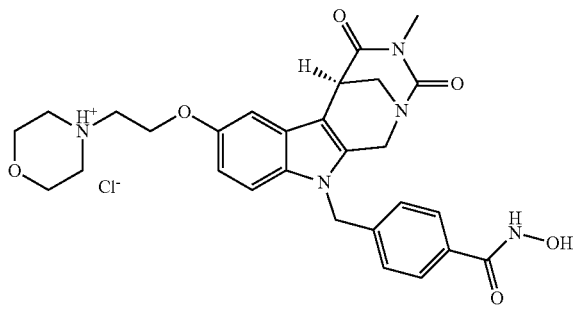

R-21

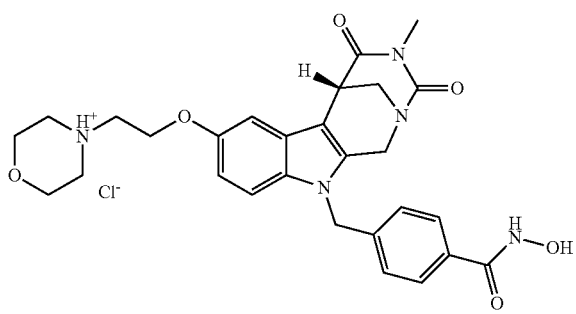

S-21 and or, in another embodiment, said compound is selected from

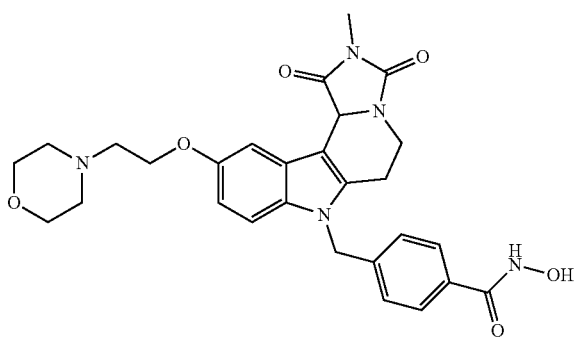

53a and

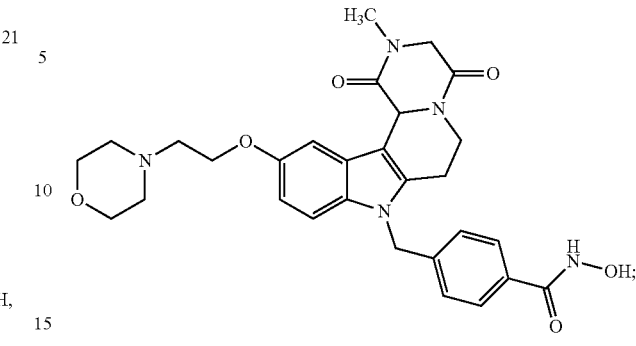

53b or, in another embodiment, said compound is selected from

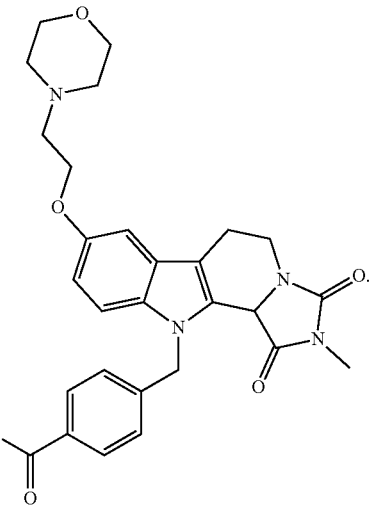

65

The present invention also relates to a pharmaceutical composition comprising
  at least one compound, or a pharmaceutically acceptable salt thereof, according to the present invention as defined above,
  optionally, one or more further agent(s) or drug(s), such as, but not limited to, cytostatic compound(s), preferably tyrosine kinase inhibitor(s) or proteasome inhibitors, and
  (c) optionally, one or more pharmaceutically acceptable excipient(s) and/or carrier(s).

The present invention also relates to a use of a compound according to the present invention, as defined above, as histone deacetylase (HDAC) inhibitor, preferably HDAC6 inhibitor. In one embodiment such use is in-vivo, in another embodiment such use is in-vitro.

The present invention also relates to a compound according to the present invention, as defined above, or pharmaceutical composition according to the present invention, as defined above, for use as a drug or medicament.

Furthermore, the present invention relates to a compound according to the present invention, as defined above, or pharmaceutical composition according to the present invention as defined above, for use in the treatment of cancer, such as, but not limited to, leukemia, breast cancer, colon cancer, uterus cancer, prostate cancer, ovarian cancer; neurological disorders; neurodegenerative diseases, such as, but not limited to, Huntington's disease, spinal muscular atrophy or Alzheimer's; stroke; inflammatory diseases; traumatic brain injury; rheumatoid arthritis; graft rejection after organ transplantation and autoimmune diseases.

In one embodiment, such use is in combination with one or more further agent(s) or drug(s), such as, but not limited to, cytostatic compound(s), such as tyrosine kinase inhibitor(s) or proteasome inhibitor(s), and/or such use is in combination with a therapy comprising a sensitization of cancer cells, e.g. radiation therapy.

Furthermore, the present invention relates to the use of a compound according to the present invention as defined above, for the manufacture of a medicament for the treatment of diseases, as defined above, in particular for the treatment of cancer, as defined above, neurological disorders, neurodegenerative diseases, as defined above, stroke, inflammatory diseases, traumatic brain injury, rheumatoid arthritis, graft rejection after organ transplantation and/or autoimmune diseases, all as defined above.

Moreover, the present invention relates to a method of treatment of a disease, comprising the step of administering to a subject a therapeutically effective amount of a compound according to the present invention, as defined above, or of a pharmaceutical composition according to the present invention as defined above, wherein the disease is preferably selected from cancer, such as, but not limited to, leukemia, breast cancer, colon cancer, uterus cancer, prostate cancer, ovarian cancer; neurological disorders; neurodegenerative diseases, such as, but not limited to, Huntington's disease, spinal muscular atrophy or Alzheimer's; stroke; inflammatory diseases; traumatic brain injury; rheumatoid arthritis; graft rejection after organ transplantation and autoimmune diseases.

In one embodiment, the method comprises administering to a subject the therapeutically effective amount of a compound according to the present invention as defined above, or a pharmaceutical composition according to the present invention as defined above, in combination with one or more further agent(s) or drug(s), such as, but not limited to, cytostatic compound(s), e.g. tyrosine kinase inhibitor(s) or proteasome inhibitors.

The present invention also relates to a method of generating/synthesizing a compound having the general formula I

wherein H is head group 1, as defined above,
said method comprising the steps of
(1) reduction of a methyl 2-(1H-indol-3-yl)-3-nitropropanoate derivative;
(2) ring closure employing a pictet-spengler reaction;
(3) transformation to the respective urea or thiourea derivative by use of 2,5-dioxopyrrolidin-1-yl carbamate derivatives, isocyanates or isothiocyanates, and
(4) ring closure mediated by a base, such as $Cs_2CO_3$;
(5) alkylating the product of (4) by use of an alkylating agent, such as tert-butyl 4-(bromomethyl)benzoate;
(6) deprotection of the benzyloxy group;
(7) introduction of an alkylamine, such as morpholine, by alkylation of the phenol resulting from (6).

In one embodiment, the method further comprises the steps of
(8) transformation of the product of (7) to trifluoroaceticacid salt of a carboxylic acid;
(9) amidation of product of (8) with O-(tetrahydro-2H-pyran-2-yl)hydroxylamine ($NH_2OTHP$) and benzotriazolyloxytris(dimethylamino)-phosphoniumhexafluorophosphate (BOP); and optionally
(10) treatment of product of (9) with an acid, such as hydrochloric acid, to form an acid addition salt.

The present invention also relates to a method of generating/synthesizing a compound having the general formula I

wherein H is head group 2, as defined above,
said method comprising the steps of
(1') alkylating an indole-2-aldehyde by use of by use of an alkylating agent, such as tert-butyl 4-(bromomethyl)benzoate;
(2') deprotection of the benzyloxy group;
(3') introduction of an alkylamine, such as morpholine, by alkylation of the phenole resulting from (2');
(4') Henry reaction with $CH_3NO_2$ to form a nitrovinyl-aryl-derivative;
(5') reduction of the nitrovinyl-aryl-derivative to an ethylamino-derivative;
(6') Pictet Spengler reaction with a glyoxalate;
(7') introduction of an urea group with 2,5-dioxopyrrolidin-1-yl methylcarbamate or an isocyanate followed by ring closure;

or alternatively reaction from the product of step (6') with 2-chloroacetyl chloride, followed by reaction with an alkylamine, such as methylamine;
(9') cleavage of the t-butyl protecting group by an acid, such as $CF_3COOH$;
(10') amidation of product of (9') with O-(tetrahydro-2H-pyran-2-yl)hydroxylamine ($NH_2OTHP$) and benzotriazolyloxytris(dimethylamino)-phosphoniumhexafluorophosphate (BOP); and optionally
(11') treatment of product of (10') with an acid, such as hydrochloric acid to form an acid addition salt.

Typically, the indole-2-aldehyde used in step (1') is commercially available. It should be noted that step (1') of the above synthesis is equivalent to step (5) of the synthesis of a compound with head group 1.

The present invention also relates to a method of generating/synthesizing a compound having the general formula I

wherein H is head group 3, as defined above, said method comprising the steps of
(1") alkylating an indole-3-aldehyde by use of an alkylating agent, such as tert-butyl 4-(bromomethyl)benzoate;
(2") deprotection of the benzyloxy group;
(3") introduction of an alkylamine, such as morpholine, by alkylation of the phenol resulting from (2");
(4") Henry reaction with $CH_3NO_2$ to form a nitrovinyl-aryl-derivative;
(5") reduction of the nitrovinyl-aryl-derivative to an ethylamino-derivative;
(6") Pictet Spengler reaction with a glyoxalate;
(7") introduction of an urea group with 2,5-dioxopyrrolidin-1-yl methylcarbamate or an isocyanate followed by ring closure;
(8") cleavage of the t-butyl protecting group by an acid, such as $CF_3COOH$;

(9") amidation of product of (8") with O-(tetrahydro-2H-pyran-2-yl)hydroxylamine (NH$_2$OTHP) and benzotriazolyloxytris(dimethylamino)-phosphoniumhexafluorophosphate (BOP); and optionally (10") treatment of product of (9") with an acid, such as hydrochloric acid, to form an acid addition salt.

Typically, the indole-3-aldehyde used in step (1") is commercially available. It should also be noted that step (1") is equivalent to step (5) of the synthesis of a compound with head group 1.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "0.03 to 60 mg per kg" should be interpreted to include not only the explicitly recited values of 0.03 to 60, but also include individual values and sub-ranges within the indicated range. Thus, included in this numerical range are individual values such as 0.03, 0.035, 0.04, 0.045, . . . , 59, 60 and sub-ranges such as from 14 to 20, from 14 to 30, from 15 to 25, from 19 to 25, from 20 to 25, from 20 to 30 and from 15 to 30, etc. This same principle applies to ranges reciting only one numerical value, such as "at least 0.03 mg per kg". Furthermore, such an interpretation should apply regardless of the breadth of the range or the characteristics being described.

HDAC Inhibitory Compounds

As discussed above, the present invention provides for a compound having the general formula I Y—[CH$_2$]$_p$-Q-H-L-(HAm)        (formula I)

wherein H is a head group selected from

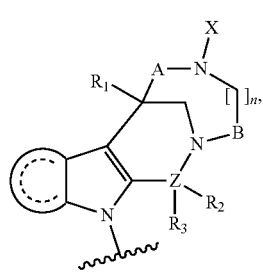

(head group 1)

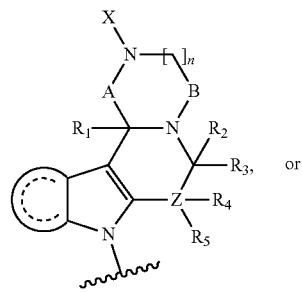

(head group 2)

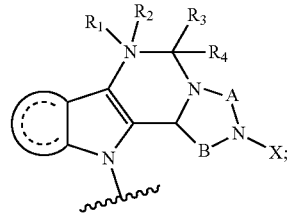

(head group 3)

wherein L is a linker having the formula

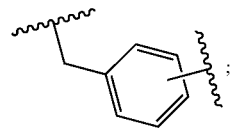

wherein (HAm) is hydroxamic acid with the formula

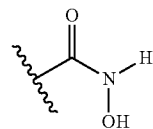 [SMILES: *C(=O)NO]

or a carbamate-protected hydroxyamic acid;

wherein A is CH$_2$, C=O or C=S;

B is CH$_2$, C=O or C=S;

n is 0 or 1;

p is 0 to 6;

Q is selected from the group comprising —CH$_2$—, O, NH, alkylamino, an ester, and an amide-group;

R$_1$ to R$_5$ are each independently selected from the group comprising hydrogen, branched or unbranched alkyl selected from C$_1$ to C$_6$, and aryl;

X is a branched or unbranched alkyl selected from C$_1$ to C$_6$;

Y is selected from the group comprising amino, alkylamino, cyclic alkylamino, dialkylamino, cyclic diaminoalkyl, such as, but not limited to, piperazinyl or 1-alkylpiperazinyl, in particular 1-methylpiperazinyl; heterocyclic alkylamino, such as, but not limited to, morpholinyl; amino acid substituents connected either via their α-amino group or their carboxy group, preferably basic amino acid substituents, such as, but not limited to, lysine, proline, histidine or arginine and pharmaceutically acceptable salts thereof, such as, but not limited to, hydrochloride, sulfate, phosphate, mesylate, tosylate or formiate or acetate;

Z is carbon, nitrogen or oxygen; with the proviso that

For headgroup 1, when Z is nitrogen, only one of R2 and R3 are present, and when Z is oxygen, none of R2 and R3 are present;

For headgroup 2, when Z is nitrogen, only one of R4 and R5 are present, and when Z is oxygen, none of R4 and R5 are present;

For headgroup 3, when Z is nitrogen, only one of R1 and R2 are present, and when Z is oxygen, none of R1 and R2 are present; and wherein the symbol

represents a five or six membered aromatic or heteroaromatic ring system, preferably a benzene-ring system;

and wherein Q is connected to said head group H at said

or a pharmaceutically acceptable salt thereof.

The inventors have surprisingly found that the attachment of a Y—[CH$_2$]$_p$-Q- part to the head group dramatically enhances the solubility, in particular the solubility in aqueous solutions, of the compound(s). Typically, such enhancement in solubility may be by 2-3 orders of magnitude. The enhancement in solubility, in turn, drastically enhances the bioavailability of the compounds according to the present invention. In one embodiment, in the Y—[CH$_2$]$_p$-Q-part, Y is selected from amino, alkylamino, cyclic alkylamino, dialkylamino, cyclic diaminoalkyl, such as, but not limited to, piperazinyl or 1-alkyl piperazinyl, in particular 1-methylpiperazinyl, heterocyclic alkylamino, such as, but not limited to, morpholinyl. In a preferred embodiment, Y is heterocyclic alkylamino, e.g. morpholinyl or morpholinoethyl. In one embodiment, Q is O In one embodiment, Y is morpholinyl, p is 2 and Q is O.

The headgroups 1-3 in accordance with the present invention, and compounds comprising these, may serve as a core for attachment of a suitable solubility-conferring Y—[CH$_2$]$_p$-Q- part, as defined above.

In one embodiment, the head group H in formula I of the compound of the invention is head group 1 and is preferably selected from

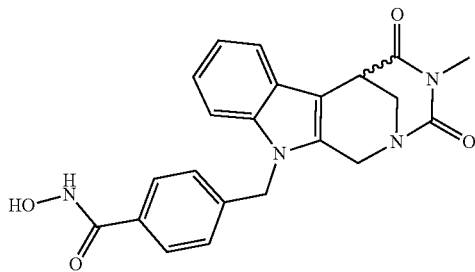

N-Hydroxy-4-((4-methyl-3,5-dioxo-3,4,5,6-tetrahydro-2,6-methano[1,3]diazocino[5,6-b]indol-11(1H)-yl)methyl)benzamide

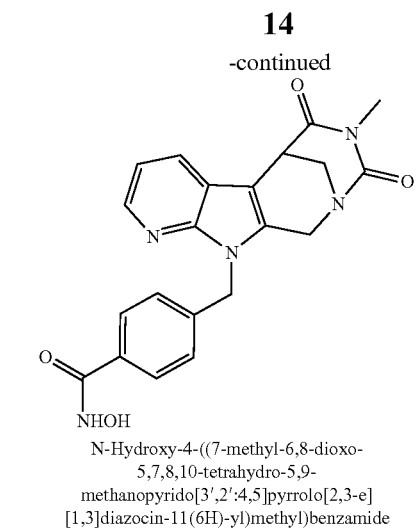

N-Hydroxy-4-((7-methyl-6,8-dioxo-5,7,8,10-tetrahydro-5,9-methanopyrido[3',2':4,5]pyrrolo[2,3-e][1,3]diazocin-11(6H)-yl)methyl)benzamide

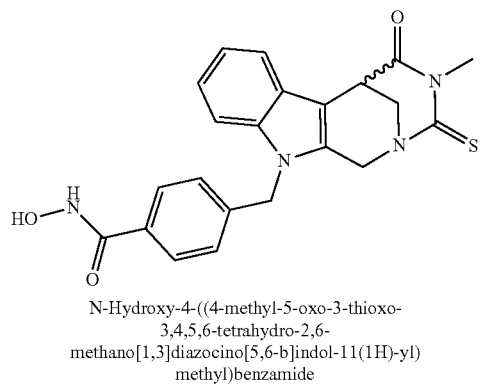

N-Hydroxy-4-((4-methyl-5-oxo-3-thioxo-3,4,5,6-tetrahydro-2,6-methano[1,3]diazocino[5,6-b]indol-11(1H)-yl)methyl)benzamide

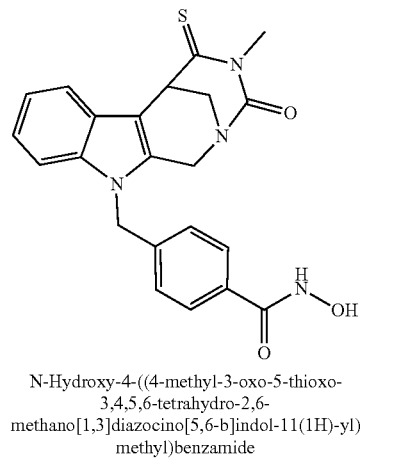

N-Hydroxy-4-((4-methyl-3-oxo-5-thioxo-3,4,5,6-tetrahydro-2,6-methano[1,3]diazocino[5,6-b]indol-11(1H)-yl)methyl)benzamide

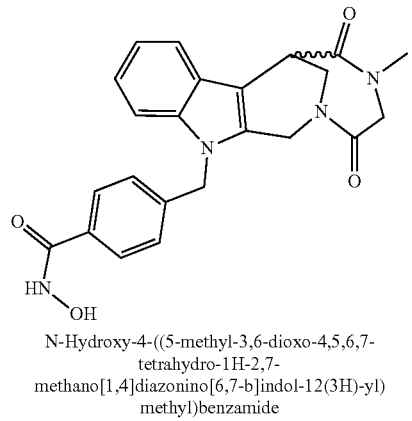

N-Hydroxy-4-((5-methyl-3,6-dioxo-4,5,6,7-tetrahydro-1H-2,7-methano[1,4]diazonino[6,7-b]indol-12(3H)-yl)methyl)benzamide

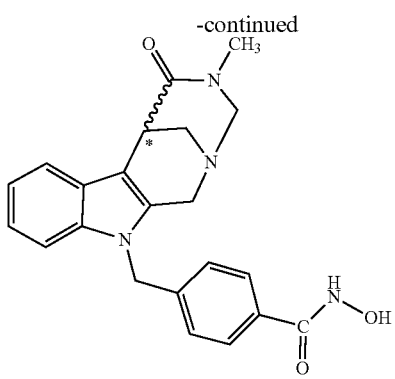

N-Hydroxy-4-((4-methyl-5-oxo-3,4,5,6-tetrahydro-2,6-methano[1,3]diazocino-[5,6-b]indol-11(1H)-yl)methyl)benzamide

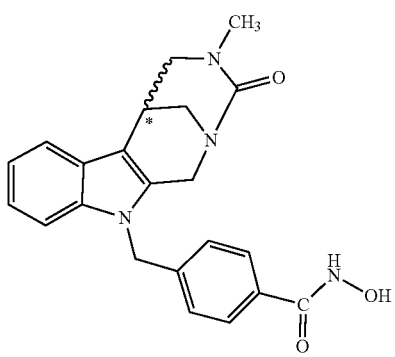

N-Hydroxy-4-((4-methyl-3-oxo-3,4,5,6-tetrahydro-2,6-methano[1,3]diazocino-[5,6-b]indol-11(1H)-yl)methyl)benzamide A preferred compound according to the present invention having head group 1 is compound 21, respective its enantiomers R-21 and S-21

21

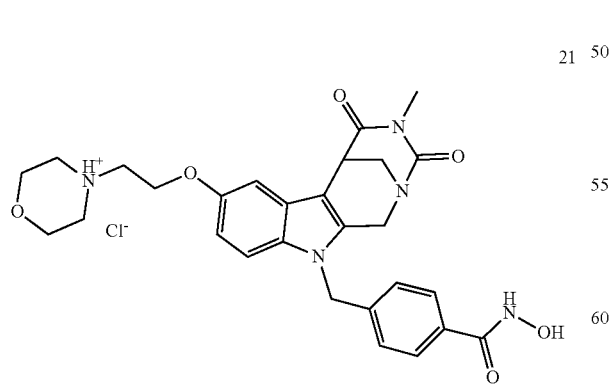

4-(2-((11(4-Hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride

R-21

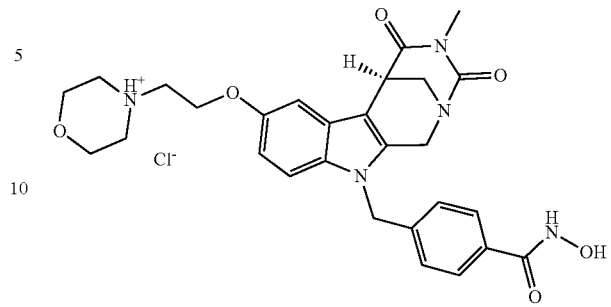

4-(2-(((6R)-11-(4-(hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride

S-21

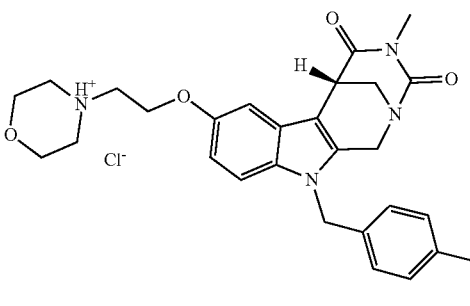

4-(2-(((6S)-11-(4-(hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride In one embodiment, the head group H in formula I of the compound of the invention is head group 2 and is preferably selected from 31a

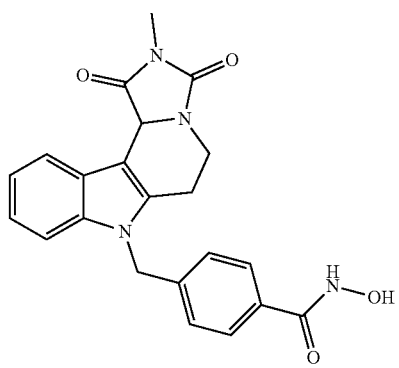

N-Hydroxy-4-((2-methyl-1,3-dioxo-2,3,5,6-tetrahydro-1H-imidazo[1',5':1,2]pyrido[4,3-b]indol-7(11cH)-yl)methyl)benzamide -continued

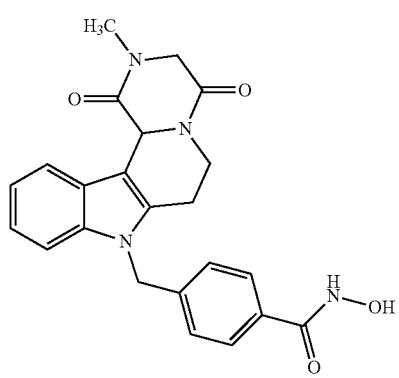

N-hydroxy-4-((2-methyl-1,4-dioxo-1,3,4,6,7,12c-hexahydropyrazino[1',2':1,2]pyrido[4,3-b]indol-8(2H)-yl)methyl)benzamide Preferred compounds according to the present invention having head group 2 are compounds 53a and 53b:

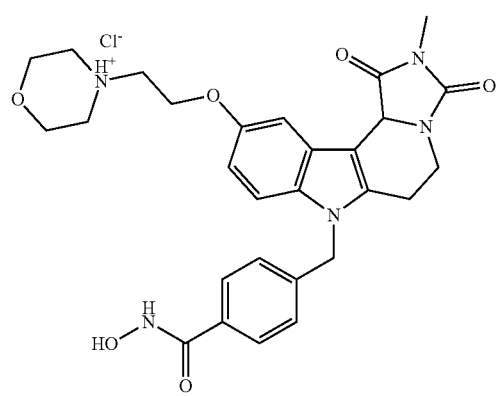

4-(2-((7-(4-(Hydroxycarbamoyl)benzyl)-2-methyl-1,3-dioxo-2,3,5,6,7,11c-hexahydro-1H-imidazo[1',5':1,2]pyrido[4,3-b]indol-10-yl)oxy)ethyl)morpholin-4-ium chloride

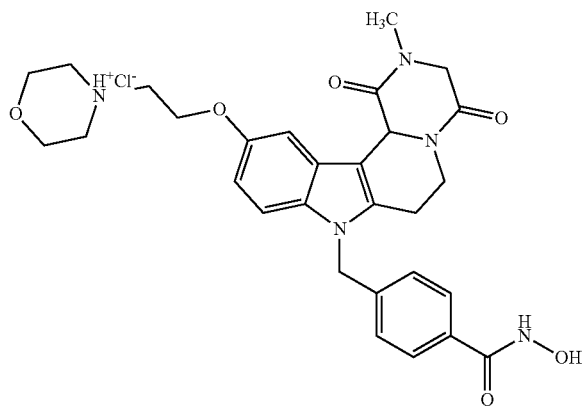

4-(2-((8-(4-(Hydroxycarbamoyl)benzyl)-2-methyl-1,4-dioxo-1,2,3,4,6,7,8,12c-octahydropyrazino[1',2":1,2]pyrido[4,3-b]indol-11-yl)oxy)ethyl)morpholin-4-ium chloride In one embodiment, the head group H in formula I of the compound of the invention is head group 3 and is preferably selected from

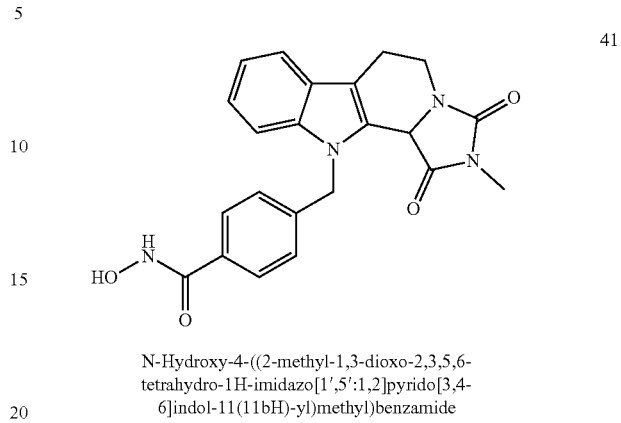

N-Hydroxy-4-((2-methyl-1,3-dioxo-2,3,5,6-tetrahydro-1H-imidazo[1',5':1,2]pyrido[3,4-6]indol-11(11bH)-yl)methyl)benzamide A preferred compound according to the present invention having head group 3 is compound 65:

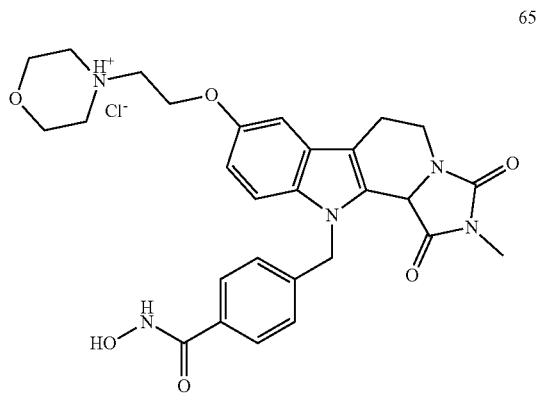

4-(2-((11-(4-(Hydroxycarbamoyl)benzyl)-2-methyl-1,3-dioxo-2,3,5,6,11,11b-hexahydro-1H-imidazo[1',5':1,2]pyrido[3,4-b]indol-8-yl)oxy)ethyl)morpholin-4-ium chloride Pharmaceutically Acceptable Salts The present invention also relates to pharmaceutically acceptable salts of the compounds according to the present invention as defined herein. Examples of pharmaceutically acceptable salts include, without limitation, the non-toxic inorganic and organic acid addition salts such as the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Pharmaceutical Compositions and Medical Uses

The present invention provides for a pharmaceutical composition comprising
(a) at least one compound, or a pharmaceutically acceptable salt thereof, according to according to the invention,
(b) optionally, one or more further agent(s) or drug(s), such as, but not limited to, cytostatic compound(s), preferably tyrosine kinase inhibitor(s) or proteasome inhibitors (e.g. Bortezomib (PS-341)), and
(c) optionally, one or more pharmaceutically acceptable excipient(s) and/or carrier(s).

The present invention also provides for the use of a compound according to the invention as histone deacetylase (HDAC) inhibitor, preferably HDAC6 inhibitor.

The present invention provides for the compound according to the present invention or the pharmaceutical composition according to the present invention for use as a drug.

The present invention provides for a compound according to the present invention or the pharmaceutical composition according to the present invention for use in the treatment of a disease.

Preferably, the disease is selected from
cancer, such as leukemia, breast cancer, colon cancer, uterus cancer, prostate cancer, ovarian cancer,
neurological disorders,
neurodegenerative diseases, such as Huntington's disease, spinal muscular atrophy or Alzheimer's,
stroke,
inflammatory diseases,
traumatic brain injury,
rheumatoid arthritis,
graft rejection after organ transplantation
and
autoimmune diseases.

In one embodiment, the compound according to the present invention or the pharmaceutical composition according to the present invention is used in combination with one or more further agent(s) or one or more drug(s), such as, but not limited to cytostatic compound(s), such as tyrosine kinase inhibitor(s) or proteasome inhibitors (e.g. Bortezomib (PS-341)).

In one embodiment, the compound according to the present invention or the pharmaceutical composition according to the present invention is used in combination with one or more further agent(s) or one or more drug(s), such as, but not limited to cytostatic compound(s), such as tyrosine kinase inhibitor(s) or proteasome inhibitors (e.g. Bortezomib (PS-341)) and/or is used in combination with another suitable therapy, such as a sensitization of cancer cells, e.g. radiation therapy. Such combined use may for example involve the administration of a compound according to the present invention during a time period while another therapy is ongoing or being performed. Such combination use may therefore be concomitant or in an overlapping manner.

Acetylated chromatin is more open and has been implicated in the increased radiation sensitivities observed in some cell types. Thus, HDAC inhibitors may be useful as radiation sensitizing agents.

Administration and Formulation

The administration of the compounds according to the present invention and of the pharmaceutical compositions according to the present invention may be performed in any of the generally accepted modes of administration available in the art. Illustrative examples of suitable modes of administration include intravenous, oral, by inhalation, parenteral, topical, transdermal and rectal delivery. Oral and intravenous deliveries are preferred.

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a pharmaceutically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, topical, sub-lingual, transdermal, parenteral (including cutaneous, subcutaneous, intramuscular, intraperitoneal, intravenous, intraarterial, intracerebral, injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents.

Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

Compositions suitable for administration also include lozenges comprising the active agent in a flavoured base, usually sucrose and acacia or tragacanth; pastilles comprising the active ingredient in an inert base such as gelatin and glycerol or sucrose and acacia.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

The present invention also provides for the use of a compound according to the present invention, as defined above, for the manufacture of a medicament for the treatment of diseases, as defined above, in particular for the treatment of cancer, as defined above, neurological disorders, neurodegenerative diseases, stroke, inflammatory diseases, traumatic brain injury, rheumatoid arthritis, graft rejection after organ transplantation and/or autoimmune diseases, all as defined above.

Methods for Treatment

The present invention also provides a method of treatment of a disease. Said treatment method comprises the step of administering to a subject a therapeutically effective amount of a compound according to the present invention or of a pharmaceutical composition according to the present invention.

A "therapeutically effective amount" of a compound according to the present invention preferably refers to the amount necessary to achieve the therapeutic outcome.

The dosage of the compounds according to the present invention is carried out in the order of magnitude customary for histone deacetylases inhibitors. For example, the customary dose in the case of systemic therapy (p.o.) may be between 0.03 and 60 mg/kg body weight per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

Preferably, the present invention provides a method of treatment of a disease, comprising the step of administering to a subject a therapeutically effective amount of a compound according to the present invention or of a pharmaceutical composition according to the present invention, wherein the disease is selected from cancer, such as leukemia, breast cancer, colon cancer, uterus cancer, prostate cancer, ovarian cancer,
neurological disorders,
neurodegenerative diseases, such as Huntington's disease, spinal muscular atrophy or Alzheimer's,
stroke,
inflammatory diseases,
traumatic brain injury,
rheumatoid arthritis,
graft rejection after organ transplantation
and
autoimmune diseases.

In one embodiment, the method of treatment of a disease of the present invention comprises administering to a subject a therapeutically effective amount of a compound according to the present invention or a pharmaceutical composition of the present invention in combination with one or more further agent(s) or drug(s), such as, but not limited to, cytostatic compound(s), e.g. tyrosine kinase inhibitor(s), as discussed above.

In one embodiment, the method of treatment of a disease of the present invention comprises sensitization of cancer cells, preferably during radiation therapy, as discussed above.

As discussed above, the administration of the compounds according to the present invention and the pharmaceutical compositions according to the present invention may be performed in any of the generally accepted modes of administration available in the art. Illustrative examples of suitable modes of administration include intravenous, oral, nasal, by inhalation, parenteral, topical, transdermal and rectal delivery. Oral and intravenous delivery are preferred.

Synthesis of the Compounds of the Invention

The present invention provides a method of generating/synthesizing compounds according to the present invention:

More specifically, in one aspect, the present invention relates to a method of generating/synthesizing a compound having the general formula I

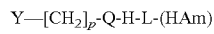
Y—[CH$_2$]$_p$-Q-H-L-(HAm)  (formula I)

wherein H is head group 1, as defined above,
said method comprising the steps of
(1) reduction of a methyl 2-(1H-indol-3-yl)-3-nitropropanoate derivative;
(2) ring closure employing a pictet-spengler reaction;
(3) transformation to the respective urea or thiourea derivative by use of 2,5-dioxopyrrolidin-1-yl carbamate derivatives, isocyanates or isothiocyanates, and
(4) ring closure mediated by a base, such as Cs$_2$CO$_3$;
(5) alkylating the product of (4) by use of an alkylating agent, such as tert-butyl 4-(bromomethyl)benzoate;
(6) deprotection of the benzyloxy group;
(7) introduction of an alkylamine, such as morpholine, by alkylation of the phenol resulting from (6).

In one embodiment, the method further comprises the steps of
(8) transformation of the product of (7) to trifluoroacetic-acid salt of a carboxylic acid;
(9) amidation of product of (8) with O-(tetrahydro-2H-pyran-2-yl)hydroxylamine (NH$_2$OTHP) and benzotriazolyloxytris(dimethylamino)-phosphoniumhexafluorophosphate (BOP); and optionally
(10) treatment of product of (9) with an acid, such as hydrochloric acid, to form an acid addition salt.

In a further aspect, the present invention relates to a method of generating/synthesizing a compound having the general formula I

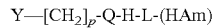
Y—[CH$_2$]$_p$-Q-H-L-(HAm)  (formula I)

wherein H is head group 2, as defined above,
said method comprising the steps of
(1') alkylating an indole-2-aldehyde by use of by use of an alkylating agent, such as tert-butyl 4-(bromomethyl)benzoate;
(2') deprotection of the benzyloxy group;
(3') introduction of an alkylamine, such as morpholine, by alkylation of the phenole resulting from (2');
(4') Henry reaction with CH$_3$NO$_2$ to form a nitrovinyl-aryl-derivative;
(5') reduction of the nitrovinyl-aryl-derivative to an ethylamino-derivative;
(6') Pictet Spengler reaction with a glyoxalate;
(7') introduction of an urea group with 2,5-dioxopyrrolidin-1-yl methylcarbamate or an isocyanate followed by ring closure;
or alternatively reaction from the product of step (6') with 2-chloroacetyl chloride, followed by reaction with an alkylamine, such as methylamine;
(9') cleavage of the t-butyl protecting group by an acid, such as CF$_3$COOH;

(10') amidation of product of (9') with O-(tetrahydro-2H-pyran-2-yl)hydroxylamine (NH₂OTHP) and benzotriazolyloxytris(dimethylamino)-phosphoniumhexafluorophosphate (BOP); and optionally (11') treatment of product of (10') with an acid, such as hydrochloric acid to form an acid addition salt.

In yet a further aspect, the present invention relates to a method of generating/synthesizing a compound having the general formula I Y—[CH$_2$]$_p$-Q-H-L-(HAm)   (formula I)

wherein H is head group 3, as defined above, said method comprising the steps of (1") alkylating an indole-3-aldehyde by use of an alkylating agent, such as tert-butyl 4-(bromomethyl)benzoate;

(2") deprotection of the benzyloxy group;

(3") introduction of an alkylamine, such as morpholine, by alkylation of the phenol resulting from (2");

(4") Henry reaction with CH$_3$NO$_2$ to form a nitrovinyl-aryl-derivative;

(5") reduction of the nitrovinyl-aryl-derivative to an ethylamino-derivative;

(6") Pictet Spengler reaction with a glyoxalate;

(7") introduction of an urea group with 2,5-dioxopyrrolidin-1-yl methylcarbamate or an isocyanate followed by ring closure;

(8") cleavage of the t-butyl protecting group by an acid, such as CF$_3$COOH;

(9") amidation of product of (8") with O-(tetrahydro-2H-pyran-2-yl)hydroxylamine (NH₂OTHP) and benzotriazolyloxytris(dimethylamino)-phosphoniumhexafluorophosphate (BOP); and optionally (10") treatment of product of (9") with an acid, such as hydrochloric acid, to form an acid addition salt.

Further exemplary details of the synthesis of embodiments of compounds according to the present invention are described in the following:

Regarding the Compounds of the Invention with Head Group 1:

Formation of 4-(2-((11-(4-(hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride (compound 21)

With regard to the development of specific HDAC6 inhibitors with improved solubility the phenolic intermediate 15 was synthesized as described in the literature (Mahboobi, Sellmer et al. 2016) according to the Scheme 1A below.

Subsequent alkylation of 15 with 4-(2-chloroethyl)morpholine hydrochloride (16) resulted in formation of 17, which was transformed to the trifluoroacetic-acid salt of carboxylic acid 18. Amidation of 18 with O-(tetrahydro-2H-pyran-2-yl)hydroxylamine (NH₂OTHP) (19) mediated by BOP (Benzotriazolyloxytris(dimethylamino)-phosphoniumhexafluorophosphate) led to 20, which was treated with hydrochloric acid to give the desired product 21.

Cleavage of the O-(tetrahydro-2H-pyran-2-yl) group by another suitable acid leads to the salt of the respective acid.

Scheme 1A: Synthesis of compound 21 with H being a head group 1.

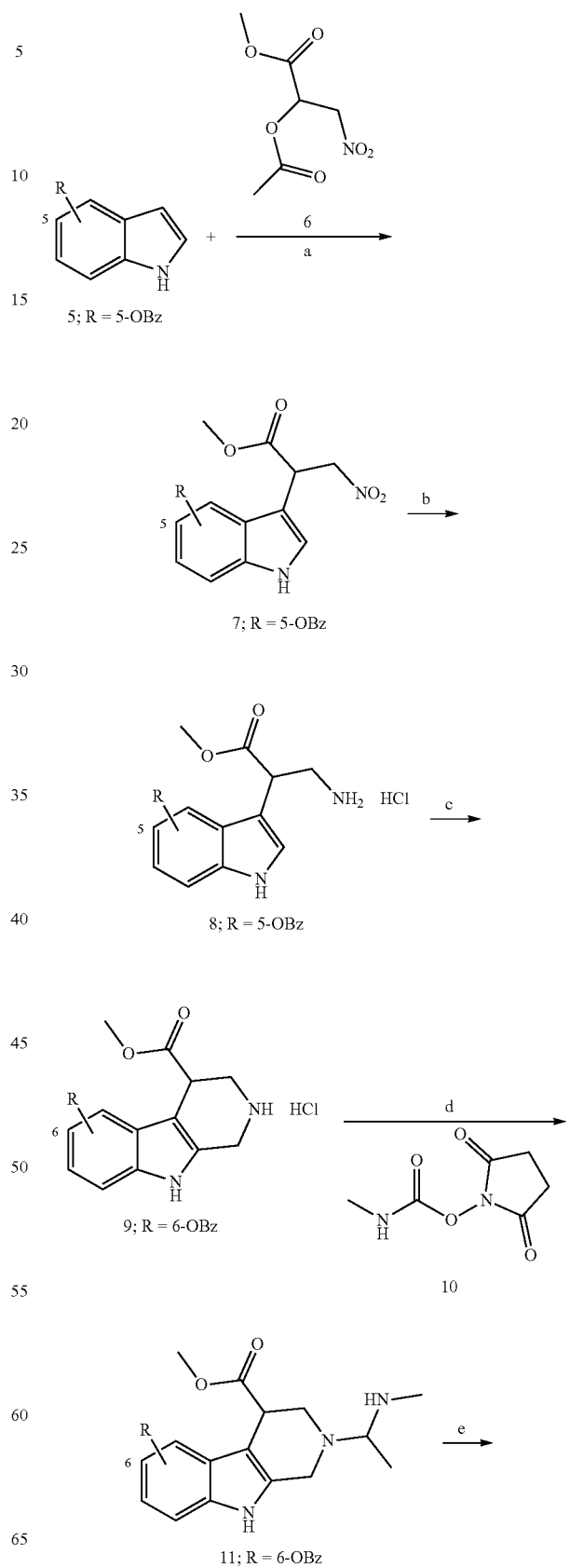

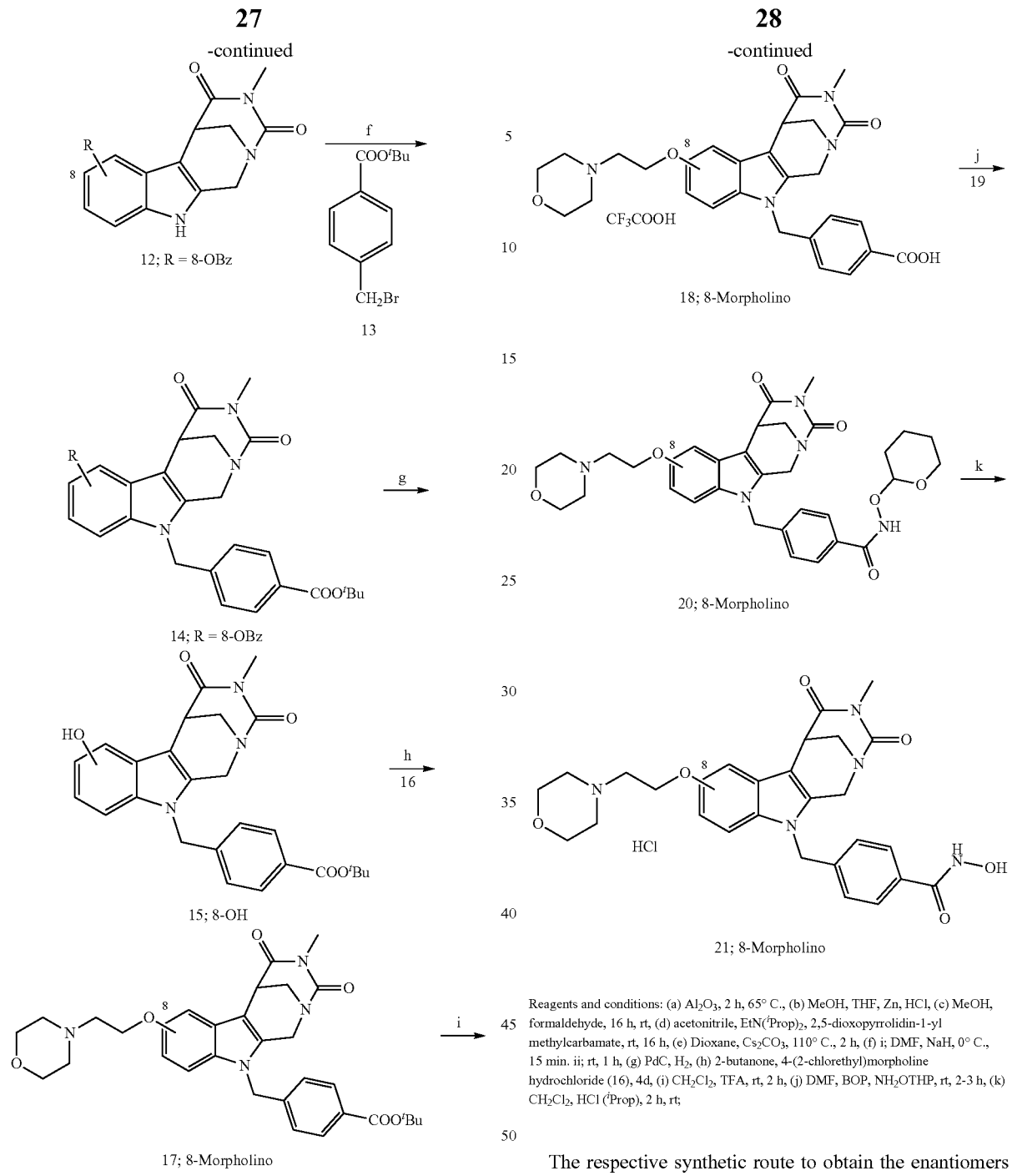

Reagents and conditions: (a) Al$_2$O$_3$, 2 h, 65° C., (b) MeOH, THF, Zn, HCl, (c) MeOH, formaldehyde, 16 h, rt, (d) acetonitrile, EtN($^i$Prop)$_2$, 2,5-dioxopyrrolidin-1-yl methylcarbamate, rt, 16 h, (e) Dioxane, Cs$_2$CO$_3$, 110° C., 2 h, (f) i; DMF, NaH, 0° C., 15 min. ii; rt, 1 h, (g) PdC, H$_2$, (h) 2-butanone, 4-(2-chlorethyl)morpholine hydrochloride (16), 4d, (i) CH$_2$Cl$_2$, TFA, rt, 2 h, (j) DMF, BOP, NH$_2$OTHP, rt, 2-3 h, (k) CH$_2$Cl$_2$, HCl ($^i$Prop), 2 h, rt;

The respective synthetic route to obtain the enantiomers of 21 is given in scheme 1B below.

Scheme 1B: Enantioselective synthesis of (R)-21 and (S)-21

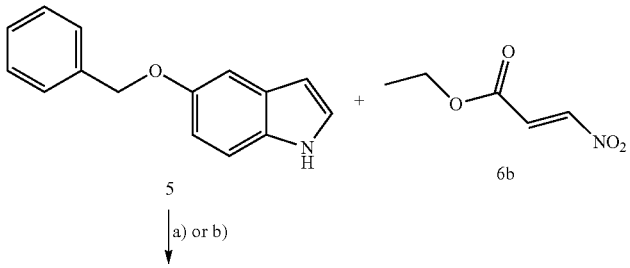

-continued
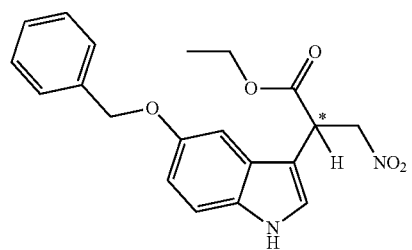
(R)-7a: R/S >99.5:0.5
(S)-7a: S/R >99.5:0.5
↓ c
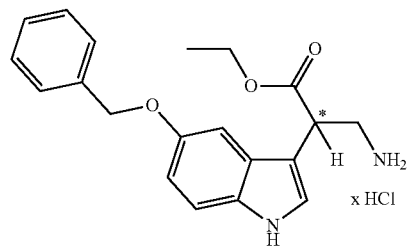
(R)-8a: R
(S)-8a: S
d →
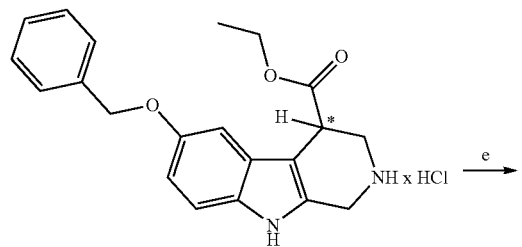
(R)-9a: R/S >98:2
(S)-9a: S/R >98:2
e →
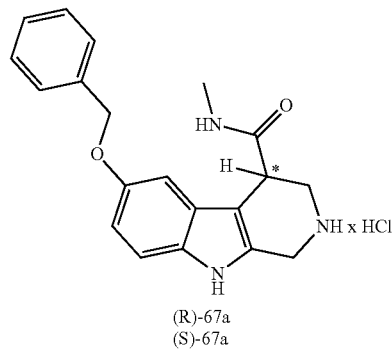
(R)-67a
(S)-67a
f →
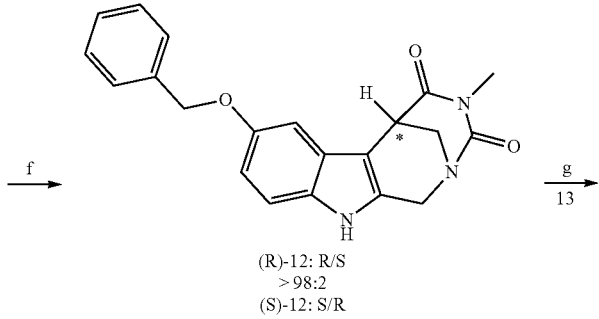
(R)-12: R/S >98:2
(S)-12: S/R >98:2
g / 13 →
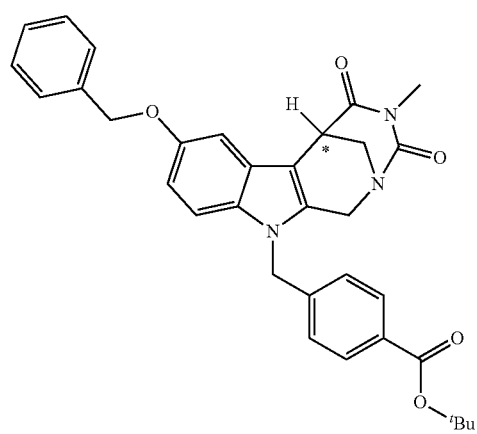
(R)-14
(S)-14
h →
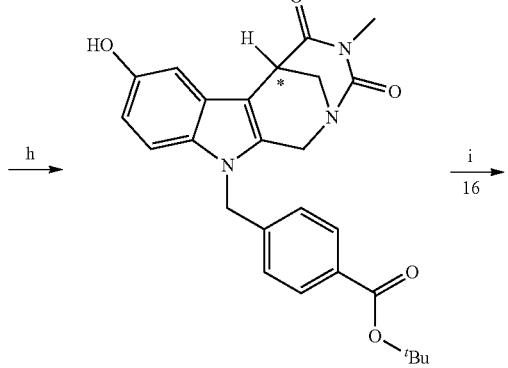
(R)-15
(S)-15
i / 16 →

-continued

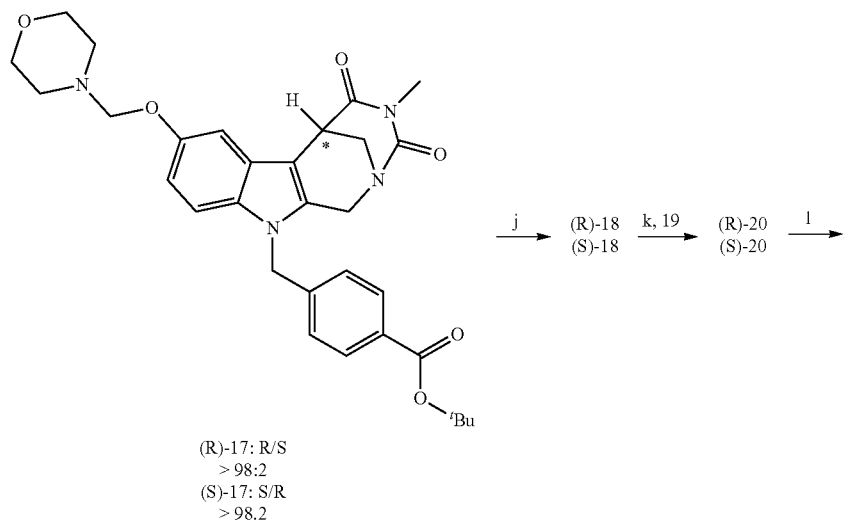

(R)-17: R/S > 98:2
(S)-17: S/R > 98:2

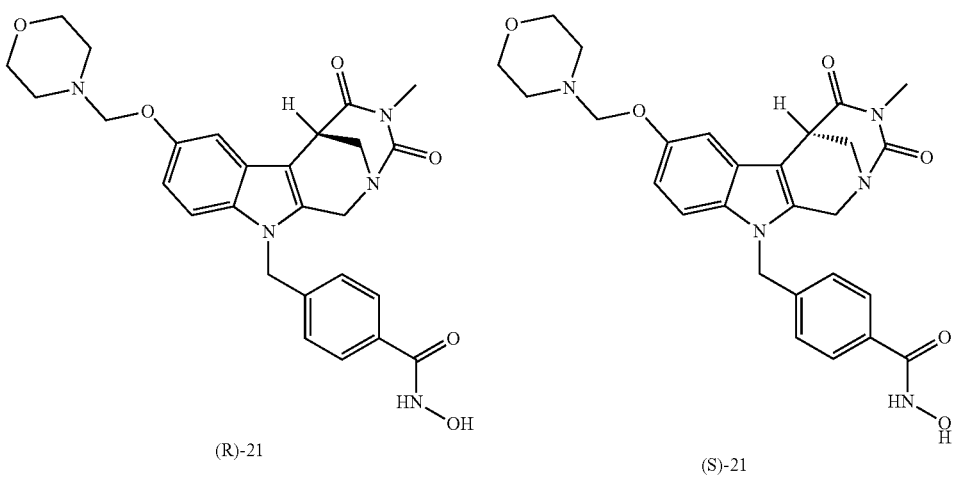

(R)-21

(S)-21

Reagents and conditions: (a) 2-(((1R,2S)-2-hydroxy-2,3-dihydro-1H-inden-1-yl)carbamothioyl)quinolin-1-ium tetrakis[35-bis(trifluoromethyl)phenyl]borate (66a), CHCl$_3$, -60° C., 16 H. (b)2-(((1S,2R)-2-hydroxy-2,3-dihydro-1H-inden-1-yl)carbamothioyl)quinolin-1-ium tetrakis[3,5-bis(trifluoromethyl)phenyl]borate (66b), CHl$_3$, -60° C., 16 h. (c)) MeOH, THF, Zn, HCl. (d) formaldehyde, MeOH, r.t., 24 h. (e) CH$_3$NH$_2$, NaCN (kat), DCM/MeOH (1:1), DMSO, DMF, 0° C., 6d. (f)i) dil.NH$_3$-solution (5%), ii) triphosgene, pyridine, CH$_2$Cl$_2$, 0° C., 3 h. (g) (13), K$_2$CO$_3$, 2-butanone, 80° C., 16 h. (h) ammonium formate, Pd/C (10%), 75° C., 20 min, (i) K$_2$CO$_3$, 2-butanone, 80° C., 16 h, (j) CH$_2$Cl$_2$, CF$_3$COOH, rt. (k) NH$_2$OTHP (19), BOP, ($^i$Prop)$_2$NEt, THF, r.t., 1,5 h. (l) DCM, HCl$_{aqu.}$, r.t..

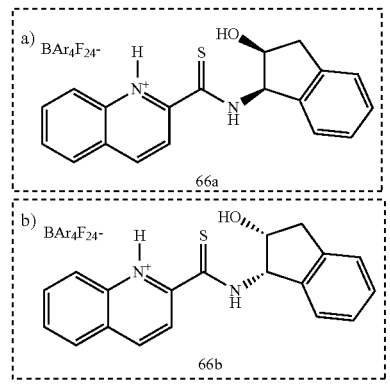

BAr$_4$F$_{24}$- = tetrakis[3,5-bis(trifluoromethyl)phenyl]borate

Regarding the Compounds of the Invention with Head Group 2:

Based on the reaction pathway shown in Schemes 2 and 3, the synthesis of compounds according to the invention with H being a head group 2 is possible.

Formation of N-Hydroxy-4-((2-methyl-1,3-dioxo-2,3,5,6-tetrahydro-1H-imidazo[1',5':1,2]pyrido[4,3-b]indol-7(11cH)-yl)methyl)benzamide (compound 31a)

With regard to the development of specific HDAC6 inhibitors with head group 2, 22 is treated with tert-butyl 4-(bromomethyl)benzoate to from 23. 23 is subsequently treated with $NH_4OAc$ and $CH_3NO_2$ to form 24. Treatment with $CHCl_3$, iProp, $NaBH_4$, $SiO_2$ builds 25, subsequently forming 26 and 27 with ethyl glyoxalate. 2,5-Dioxopyrrolidin-1-yl methylcarbamate, $Cs_2CO_3$ and dioxane treatment forms 28a. The tBu-group of 28a is transformed with $CF_3COOH$ to a carboxylate-group in 29a. Amidation of 29a with O-(tetrahydro-2H-pyran-2-yl)hydroxylamine ($NH_2OTHP$) and benzotriazolyloxytris-(dimethylamino)-phosphoniumhexafluorophosphate (BOP) forms 30a, which was treated with hydrochloric acid to give the desired product 31a.

Scheme 2a: Synthesis of compound 31a with H being a head group 2, bearing an angular annulated hydantoin increment; reagents and conditions: (a) DMF, NaH, tert-butyl 4-(bromomethyl)benzoate, (b) $NH_4OAc$, $CH_3NO_2$, (c) $CHCl_3$, iProp, $NaBH_4$, $SiO_2$, (d) i) HOAc, Zn, ii) $NH_4OH$, iii) THF, HCl; (e) MeOH, $SiO_2$, ethyl glyoxalate; (f) i) acetonitrile, EtN($^i$Prop)$_2$, 2,5-dioxopyrrolidin-1-yl methylcarbamate, rt, 16 h; ii) $Cs_2CO_3$, dioxane, (g) $CF_3COOH$, (h) DMF, BOP, $NH_2OTHP$, rt, 2-3 h, (i) MeOH, HCl$_{aqu}$, rt;

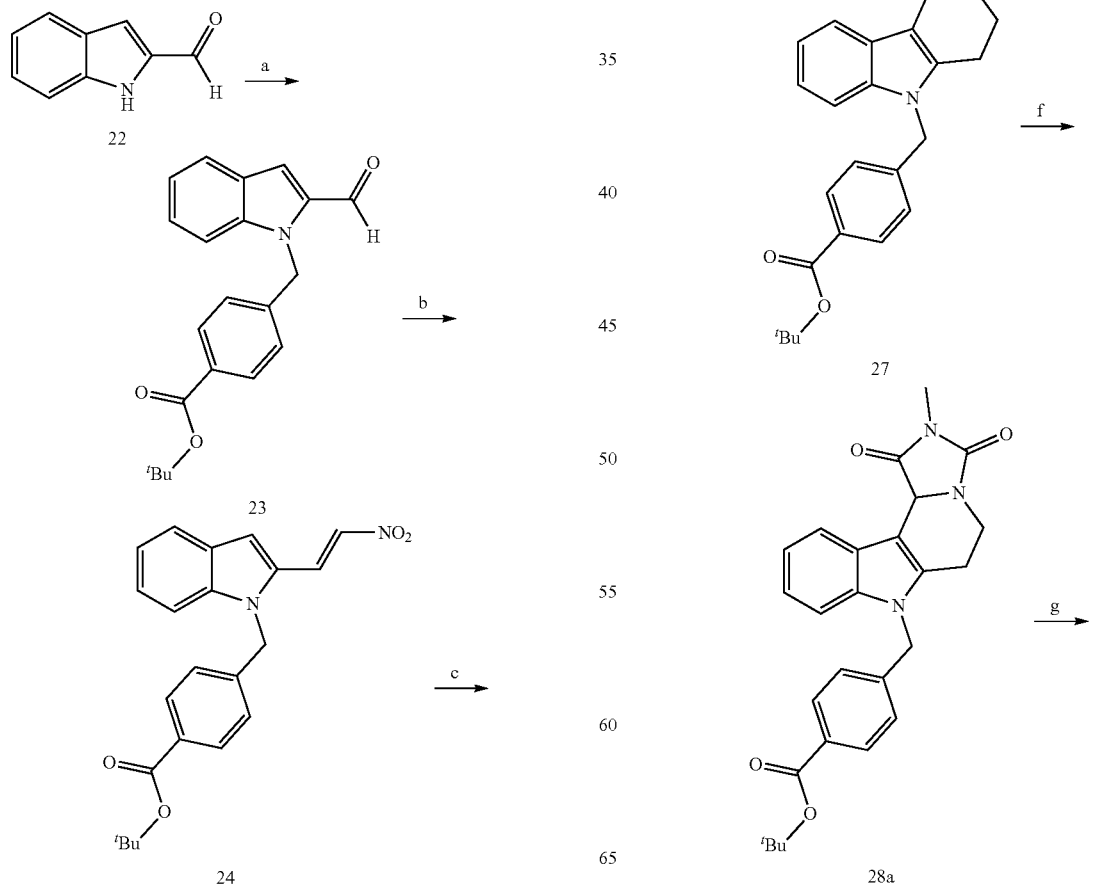

-continued
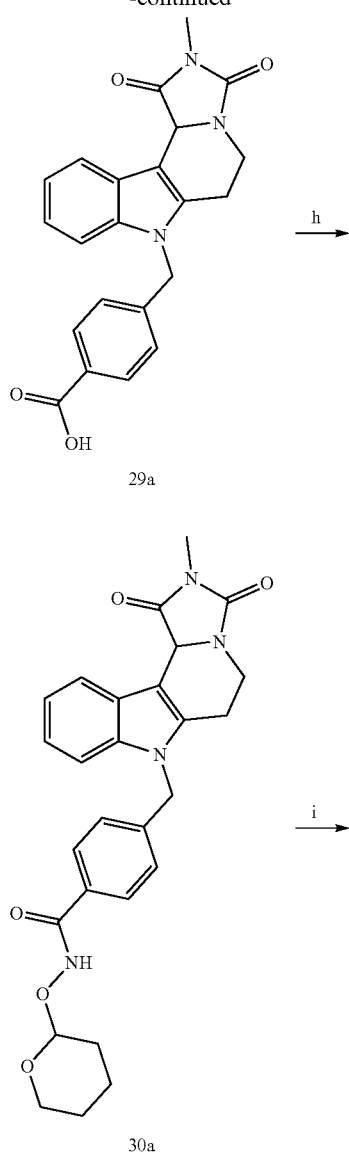
29a
30a
31a
Scheme 2b: Synthesis of compound 53a as an example.
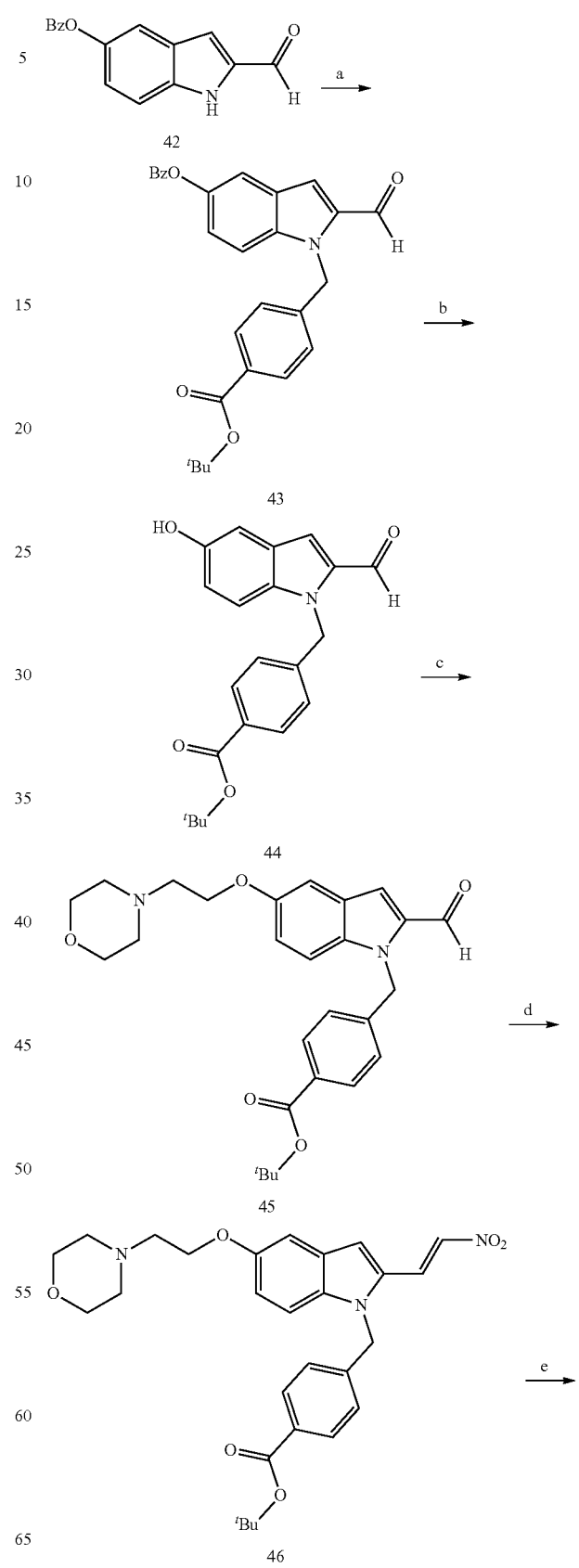
42
43
44
45
46

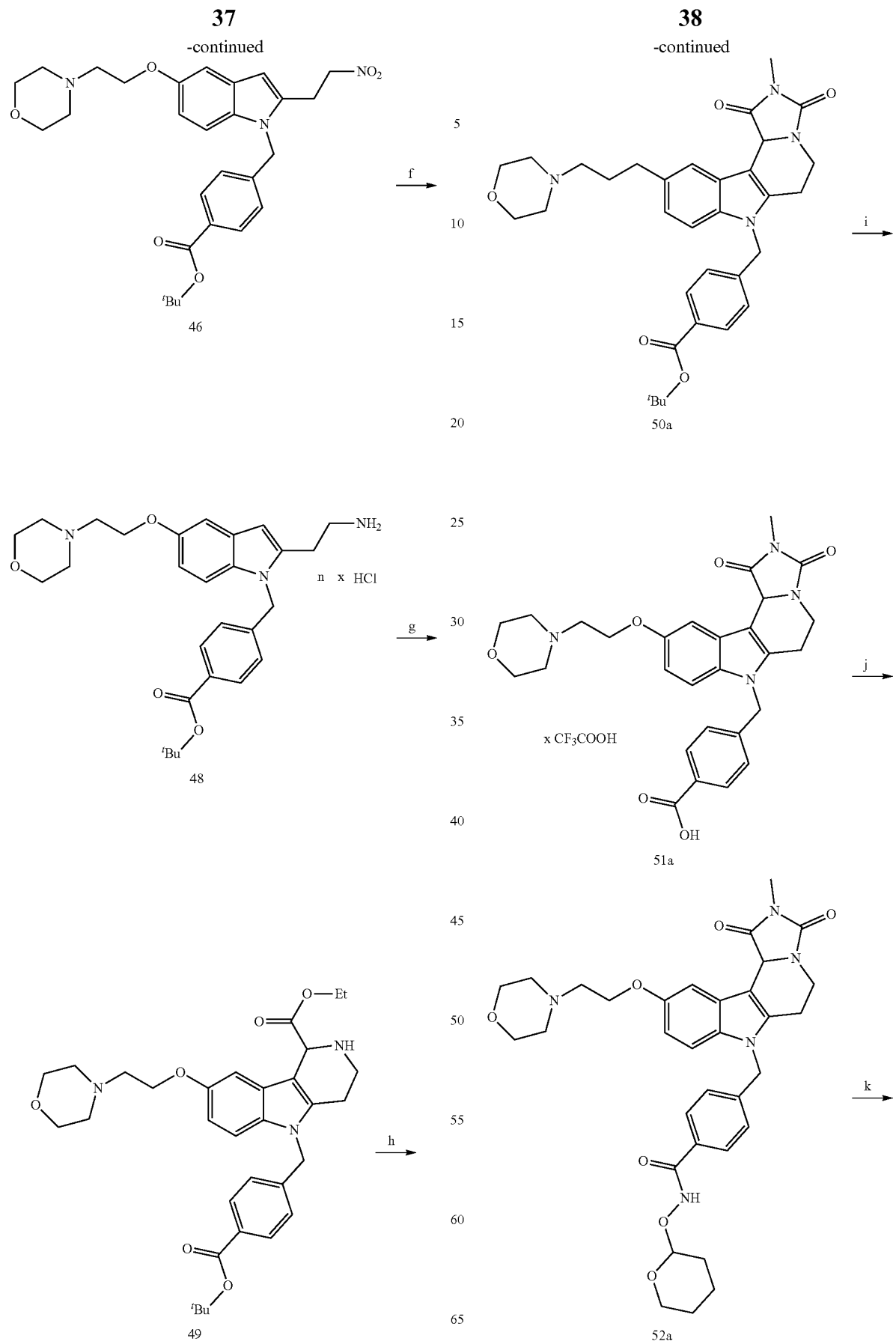

-continued

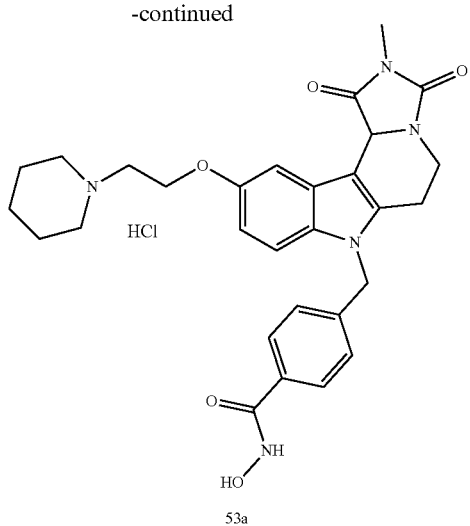

53a

Reagents and conditions: (a) DMF, NaH, tert-butyl 4-(bromomethyl)benzoate, (b) PdC, H₂. (c) 2-butanone, 4-(2-chloroethyl)-morpholine hydrochloride (16), 4d, (d) NH₄OAc, CH₃NO₂, (e) CHCl₃, iProp, NaBH₄, SiO₂, (f) i) HOAc, Zn, ii) NH₄OH, iii) THF, HCl; (g) MeOH, SiO₂, ethyl glyoxalate; (h) i) acetonitrile, EtN(iProp)₂, 2,5-dioxopyrrolidin-1-yl methylcarbamate, rt, 16 h; ii) Cs₂CO₃, dioxane, (i) CF₃COOH, (j) DMF, BOP, NH₂OTHP, rt, 2-3 h, (k) MeOH, HCl_{aqu}, rt;

Formation of N-hydroxy-4-((2-methyl-1,4-dioxo-1,3,4,6,7,12c-hexahydropyrazino[1',2':1,2]pyrido[4,3-b]indol-8(2H)-yl)methyl)benzamide (compound 31b)

With regard to the development of specific HDAC6 inhibitors with head group 2, 22 is treated with tert-butyl 4-(bromomethyl)benzoate to from 23. 23 is subsequently treated with NH₄OAc and CH₃NO₂ to form 24. Treatment with CHCl₃, iProp, NaBH₄, SiO₂ builds 25, subsequently forming 26 and 27 with ethyl glyoxalate. Treatment with ClCH₂COCl, EtN(iProp)₂, CH₂Cl₂ and subsequently with CH₃NH₂ and MeOH treatment forms 28b. The tBu-group of 28b is transformed with CF₃COOH to a carboxylate-group in 29b. Amidation of 29b with O-(tetrahydro-2H-pyran-2-yl)hydroxylamine (NH₂OTHP) and benzotriazolyloxytris-(dimethylamino)-phosphonium-hexafluorophosphate (BOP) forms 30b, which was treated with hydrochloric acid to give the desired product 31b.

Scheme 3a: Synthesis of compound 31b with H being a head group 2, bearing an angular annulated 6-membered ring system; reagents and conditions: (a) i) ClCH₂COCl, EtN(iProp)₂, CH₂Cl₂, -50° C. -> 0° C., ii) CH₃NH₂, MeOH, (b) CH₂Cl₂, CF₃COOH, 16 h, rt, (c) THF, BOP, NH₂OTHP, rt, 3.5 h, (d) MeOH, THF, CH₂Cl₂, HCl (iProp), rt.

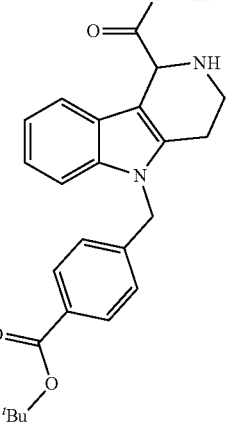

27

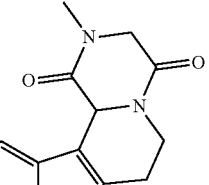

28b

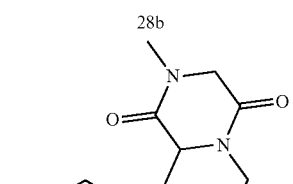

29b

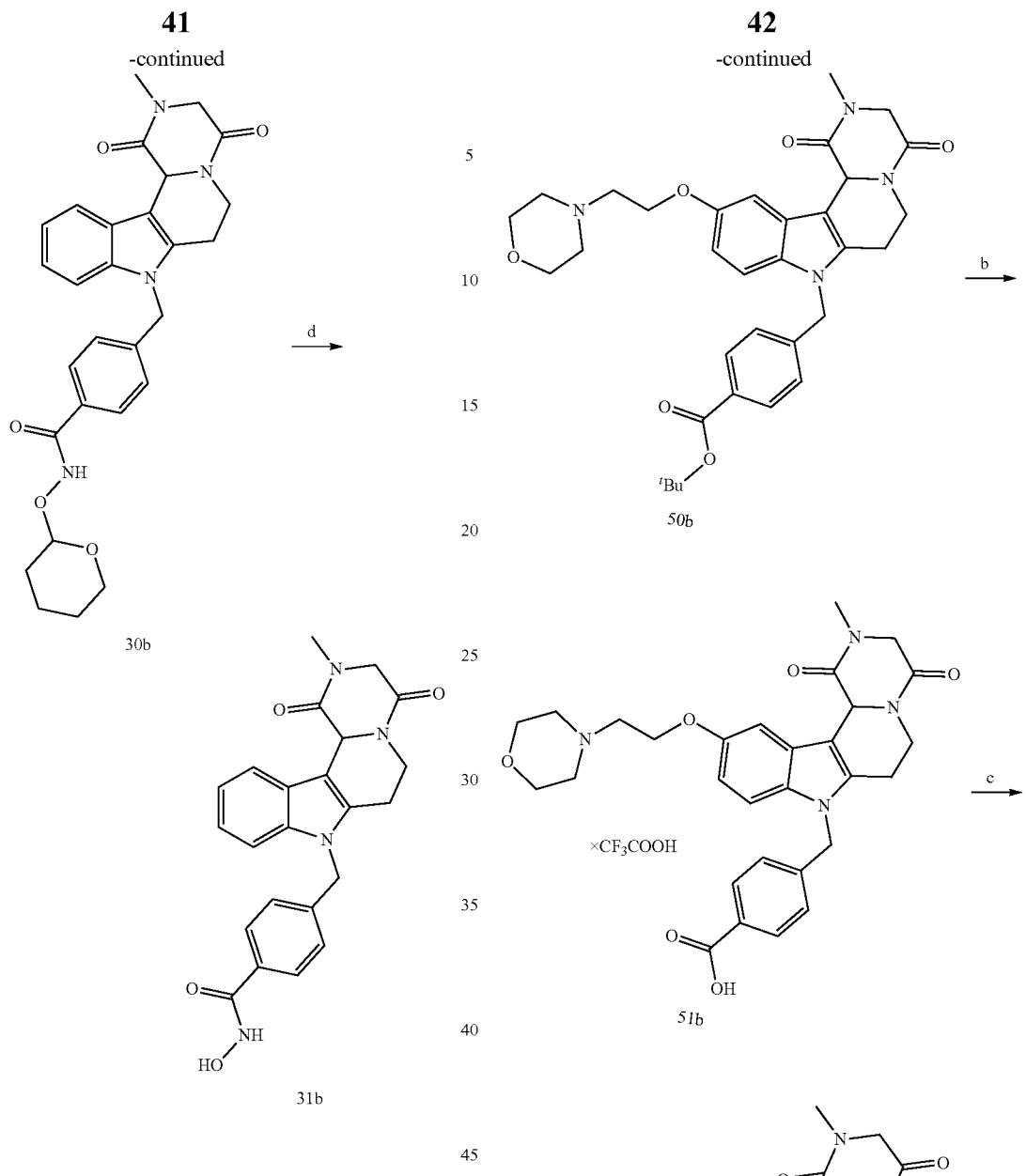
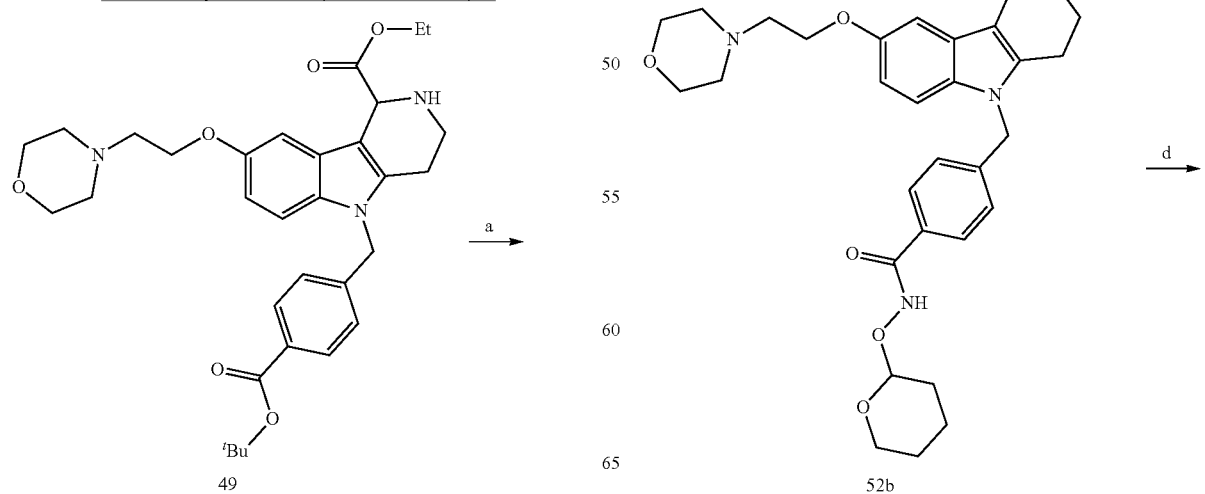
Scheme 3b: Synthesis of compound 53b as example.

-continued

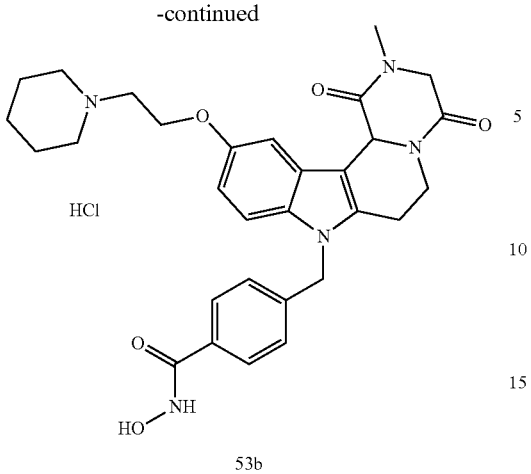

53b

Reagents and conditions: (a) i) ClCH₂COCl, EtN(iProp)₂, CH₂Cl₂, -50° C. -> 0° C., ii) CH₃NH₂, MeOH, (b) CH₂Cl₂, CF₃COOH, 16 h, rt, (c) THF, BOP, NH₂OTHP, rt, 3.5 h, (d) MeOH, THF, CH₂Cl₂, HCl (ⁱProp), rt.

Regarding the Compounds of the Invention with Head Group 3:

Based on the reaction pathway shown in Scheme 4 below, the synthesis of compounds according to the invention with H being a head group 3 is possible.

Formation of N-Hydroxy-4-((2-methyl-1,3-dioxo-2,3,5,6-tetrahydro-1H-imidazo[1',5':1,2]pyrido[3,4-b]indol-11(11 bH)-yl)methyl)benzamide (compound 41)

With regard to the development of specific HDAC6 inhibitors with improved solubility with head group 3 32 is treated with tert-butyl 4-(bromomethyl)benzoate to from 33. This is subsequently treated with NH₄OAc and CH₃NO₂ to form 34. Treatment with CHCl₃, iProp, NaBH₄, SiO₂ builds 35, subsequently forming 36 and 37 with ethyl glyoxalate. Treatment with acetonitrile, EtN(ⁱProp)₂ and 2,5-dioxopyrrolidin-1-yl methylcarbamate, Cs₂CO₃ and dioxane forms 38. The tBu-group of 38 is transformed with CF₃COOH to a carboxylate-group in 39. Amidation of 39 with O-(tetrahydro-2H-pyran-2-yl)hydroxylamine (NH₂OTHP) and benzotriazolyloxytris-(dimethylamino)-phosphoniumhexafluorophosphate (BOP) forms 40, which was treated with hydrochloric acid to give the desired product 41.

Scheme 4a: Synthesis of compound 41 with H being a head group 3, bearing an angular annulated hydantoin increment, reagents and conditions: (a) DMF, NaH, tert-butyl 4-(bromomethyl)benzoate, (b) NH₄OAc, CH₃NO₂, (c) CHCl₃, iProp, NaBH₄, SiO₂, (d) i) HOAc, Zn, ii) NH₄OH iii) THF, HCl, (e) MeOH, SiO₂, ethyl glyoxalate, (f) i) acetonitrile, EtN(ⁱProp)₂, 2,5-dioxopyrrolidin-1-yl methylcarbamate, rt, 16 h. ii) Cs₂CO₃, dioxane, (g) CF₃COOH, (h) DMF, BOP, NH₂OTHP, rt, 2-3 h, (i) MeOH, HCl_aqu, rt.

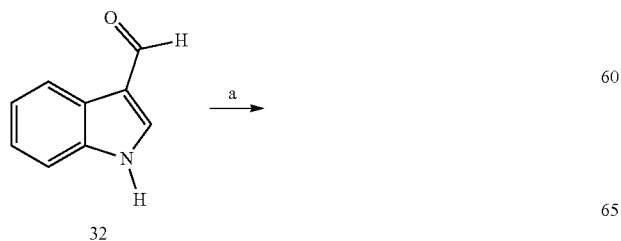

32

-continued

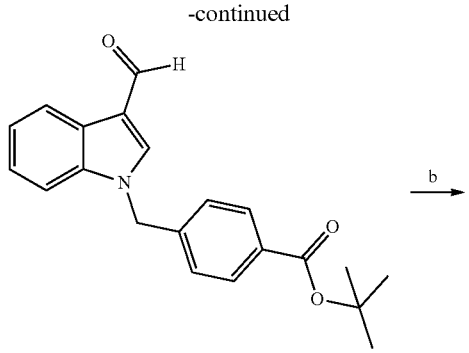

33

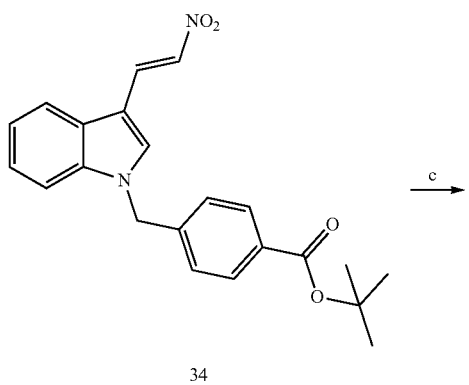

34

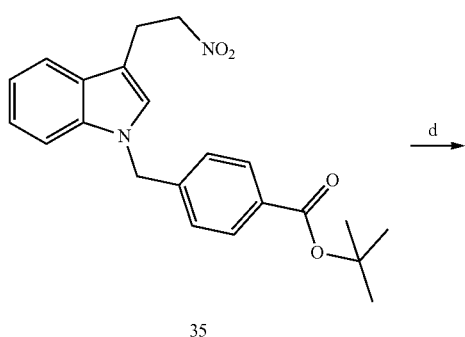

35

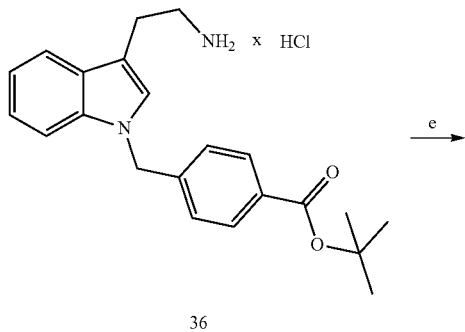

36

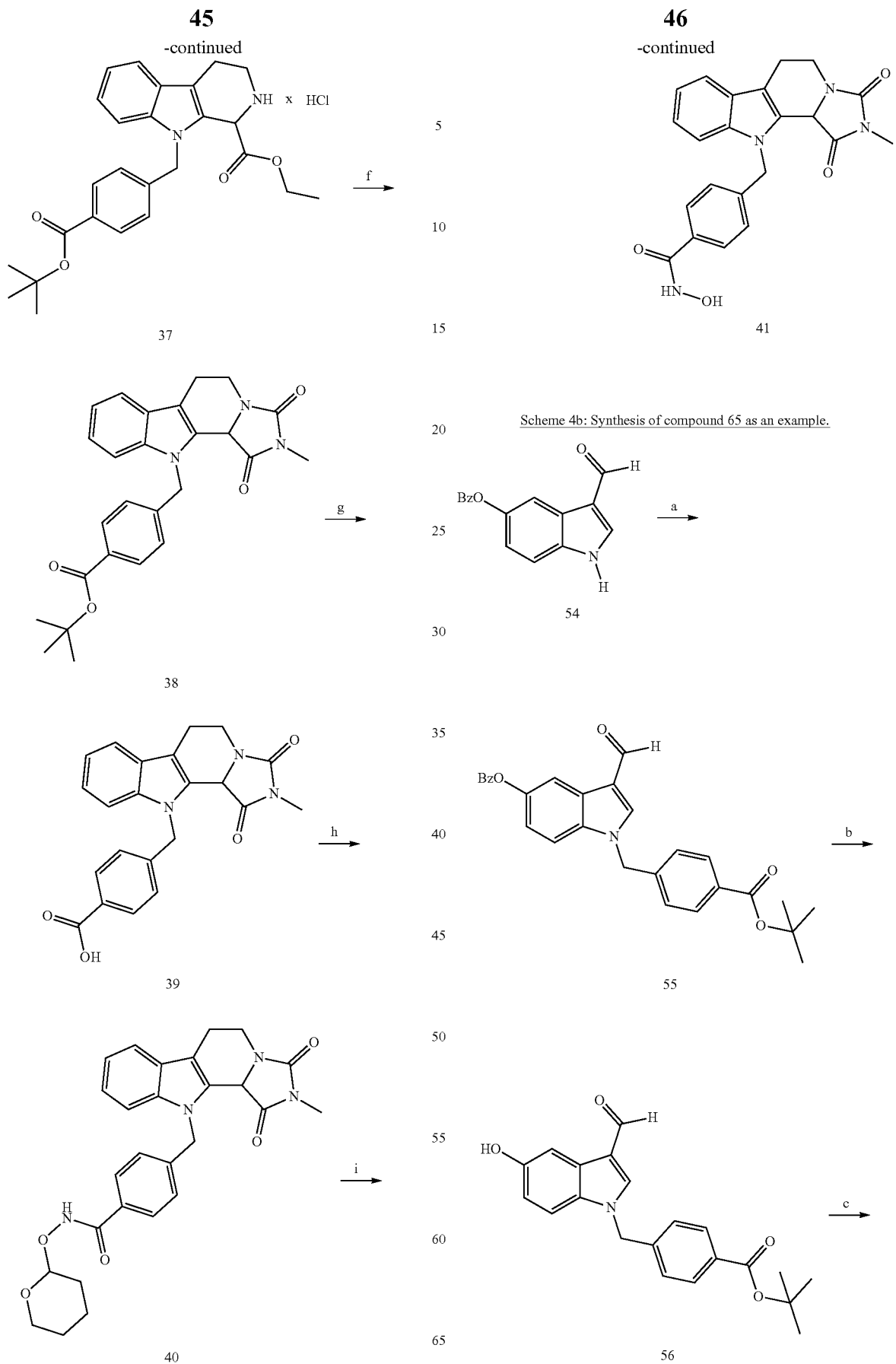

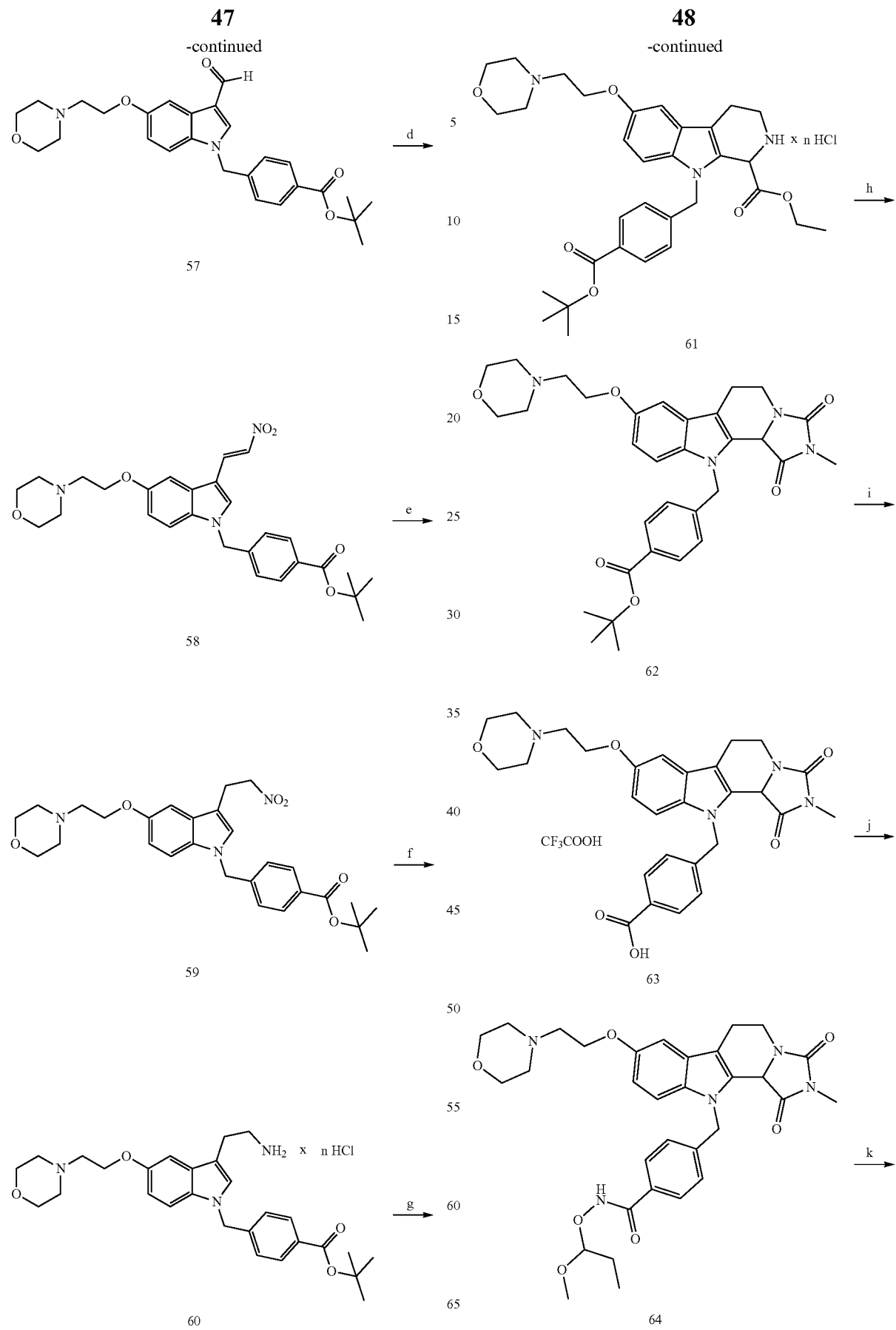

-continued

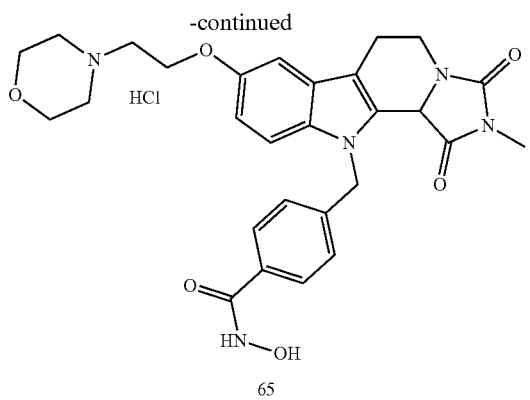

65 reagents and conditions: (a) DMF, NaH, tert-butyl 4-(bromomethyl)benzoate, (b) PdC, H$_2$, (c) 2-butanone, 4-(2-chloroethyl)-morpholine hydrochloride (16), 4d,
(d) NH$_4$OAc, CH$_3$NO$_2$, (e) CHCl$_3$, iProp, NaBH$_4$, SiO$_2$, (f) i) HOAc, Zn, ii) NH$_4$OH
iii) THF, HCl, (g) MeOH, SiO$_2$, ethyl glyoxalate, (h) i) acetonitrile,
EtN($^i$Prop)$_2$, 2,5-dioxopyrrolidin-1-yl methylcarbamate, rt, 16 h.
ii) Cs$_2$CO$_3$, dioxane, (i) CF$_3$COOH, (j) DMF, BOP, NH$_2$OTHP, rt, 2-3 h,
(k) MeOH, HCl$_{aqu}$, rt.

Further Description of Preferred Embodiments

The present invention discloses novel HDAC inhibitors. Furthermore, the present invention discloses pharmaceutical compositions comprising HDAC inhibitor(s) and exemplary treatment regimens for various diseases. These especially include cancer, neurological disorders, neurodegenerative diseases, stroke, inflammatory diseases, traumatic brain injury, rheumatoid arthritis, graft rejection after organ transplantation and autoimmune diseases. The present invention further discloses the use of HDAC inhibitors in adjuvant therapy with various standard cytostatic compounds and the sensitization of cancer cells in the context of a radiation therapy.

Histone deacetylases (HDACs) are epigenetic regulators that cleave the acetyl groups from lysine residues in proteins. HDACs are often overexpressed in tumors and thus involved in carcinogenesis. Histone deacetylase inhibitors (HDACi) inhibit the protein-deacetylation and modulate gene expression. Thereby, the growth of abnormal cells is inhibited. HDACi have shown promising effects, for example, in leukemia therapy which is up to now often impossible. Transcriptional dysregulation also seems to be involved in the molecular pathogenesis of certain neurodegenerative diseases, such as Huntington's disease, spinal muscular atrophy or Alzheimer's. While pan-HDACi have broad cytotoxic profiles due to the inhibition of several HDAC isoforms, isoform-specific HDACi have fewer side effects.

HDAC6 has two catalytic domains and a specific substrate spectrum. Substrates of HDAC6 are, for example, Tubulin-α and the chaperone HSP90. Deacetylated HSP90 stabilizes the leukemia fusion proteins BCR-ABL, PML-RAR and AML1-ETO, mutant FLT3, the pan-leukemic marker protein WT1 and oncogenic p53. As these and other substrates of HDAC6 are critically involved in tumorigenesis, HDAC6 inhibitors are suitable for the treatment of cancer.

The HDAC6 inhibitors of the present invention effect potent cytostatic and cytotoxic effects in different cell models. We also show for the first time that the expression of the protein survivin, an important factor for tumorigenesis and chemoresistance, is HDAC6 dependent. Furthermore, our selective HDAC6 inhibitors in combination with imatinib generate cytotoxic effects on BCR-ABL positive cells. At a molecular level, this is linked to a reduction of BCR-ABL, WT1 and the accumulation of acetylated tubulin.

Moreover, a synergism in killing of ovarian cancer cells by application of the proteasome inhibitor Bortezomib (PS-341) has been shown (Bazzaro et al., 2008).

The following examples and drawings illustrate the present invention without, however, limiting the same thereto.

Also shown are three compounds which may serve as core structures for further attachment of a Y—(CH$_2$)$_p$-Q- part, namely:
N-Hydroxy-4-((2-methyl-1,3-dioxo-2,3,5,6-tetrahydro-1H-imidazo[1',5':1,2]pyrido[4,3-b]indol-7(11cH)-yl)methyl)benzamide (31a),
N-hydroxy-4-((2-methyl-1,4-dioxo-1,3,4,6,7,12c-hexahydropyrazino[1',2':1,2]pyrido[4,3-b]indol-8(2H)-yl)methyl)benzamide (31b); and
N-Hydroxy-4-((2-methyl-1,3-dioxo-2,3,5,6-tetrahydro-1H-imidazo[1',5':1,2]pyrido[3,4-b]indol-11(11bH)-yl)methyl)benzamide (41).

Figure 1A:
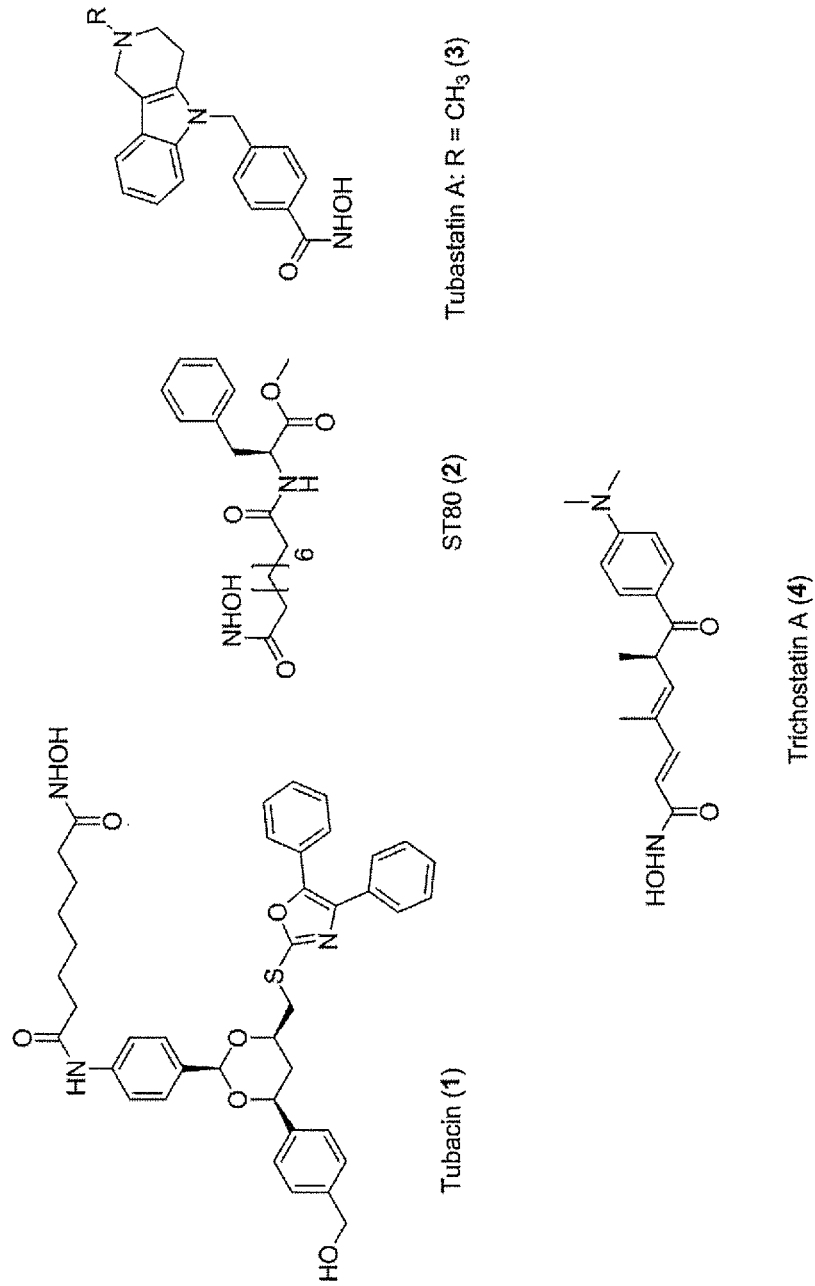
FIG. 1. Structure of HDAC inhibitors
(A) Shown are the structures of the prior art HDAC inhibitor stubacin (1), ST80 (2), tubastatin A (3) and of the pan-HDACi trichostatin A (4).
(B) Overview: general structure of the novel HDAC6 inhibitors of the invention.
(C) Shown are the structures of four specific exemplary HDAC6 inhibitors of the invention, in the form of their corresponding HCl-salts; they may however also be used in the form of their free base:
4-(2-((11-(4-(Hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride (21);
4-(2-((7-(4-(Hydroxycarbamoyl)benzyl)-2-methyl-1,3-dioxo-2,3,5,6,7,11c-hexahydro-1H-imidazo[1',5':1,2]pyrido[4,3-b]indol-10-yl)oxy)ethyl)morpholin-4-ium chloride (53a):
4-(2-((8-(4-(Hydroxycarbamoyl)benzyl)-2-methyl-1,4-dioxo-1,2,3,4,6,7,8,12c-octahydropyrazino[1',2':1,2]pyrido[4,3-b]indol-11-yl)oxy)ethyl)morpholin-4-ium chloride (53b); and
4-(2-((11-(4-(Hydroxycarbamoyl)benzyl)-2-methyl-1,3-dioxo-2,3,5,6,11,11 b-hexahydro-1H-imidazo[1',5':1,2]pyrido[3,4-b]indol-8-yl)oxy)ethyl)morpholin-4-ium chloride (65).
Figure 1B:
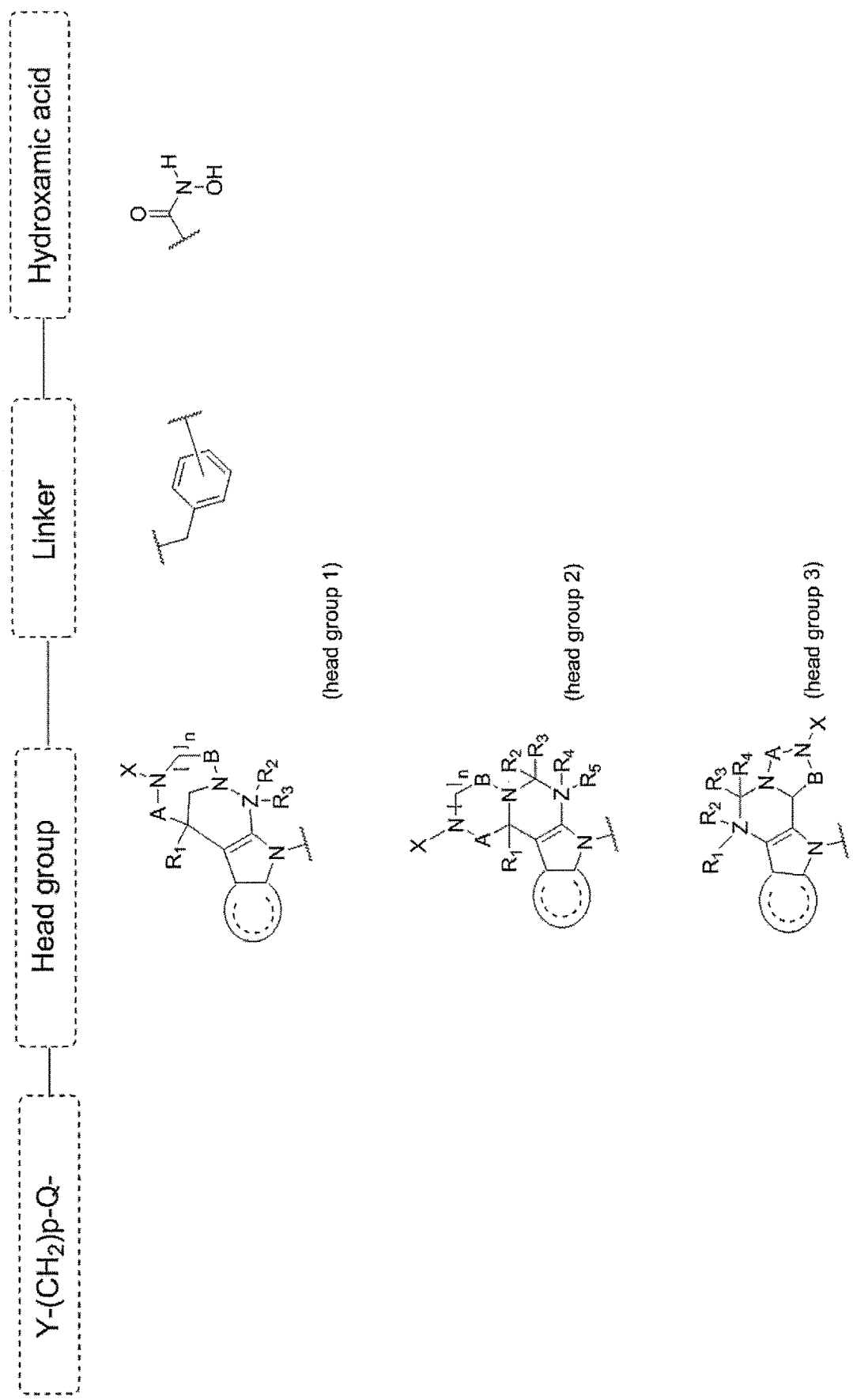
Figure 1C:
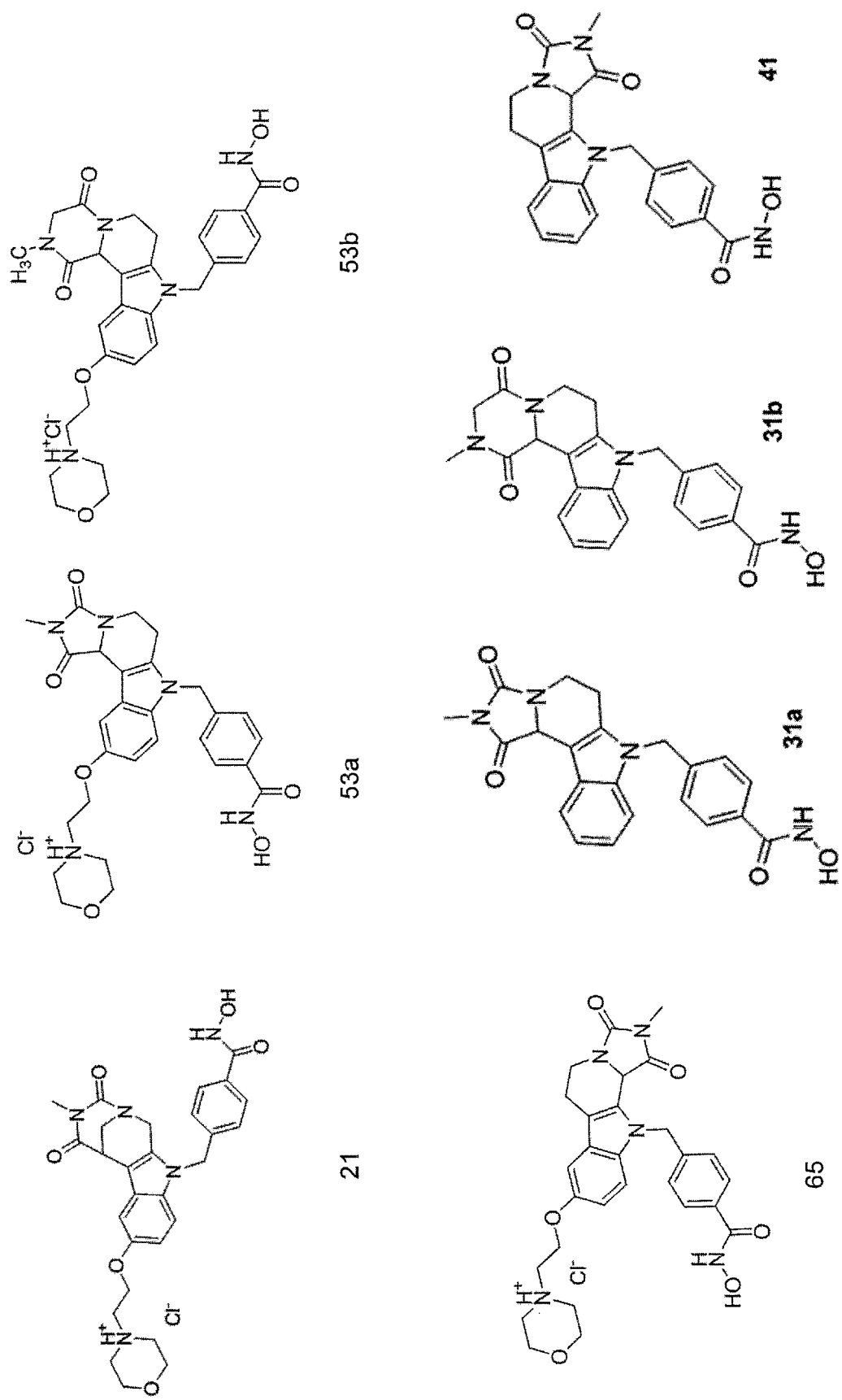
Figure 2:
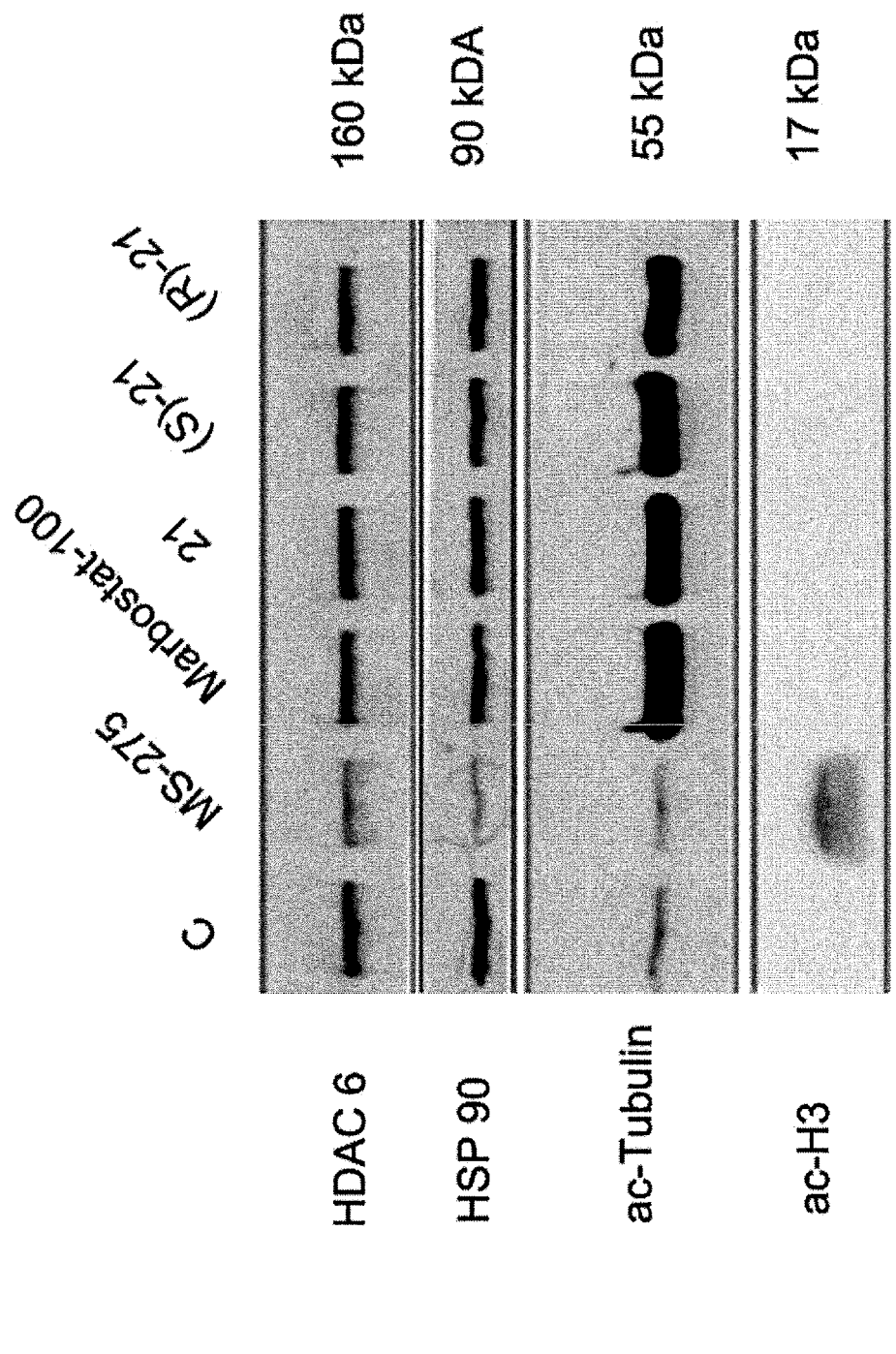

FIG. 2: MV4-11 cells were treated for 24 h with 200 nM Marbostat-100 or MS-275 (5 μM) and compared with different new HDAC6is. The cells were analysed by Western blot. The results shown are obtained from at least two independent experiments.

EXAMPLES

Materials and Methods:
Fluorescence HDAC Assay
The IC$_{50}$ values for the various inhibitors against the isoenzymes of HDAC were measured by Reaction Biology Corporation (Malvern, Pa., USA) (Buffer, Kalin et al. 2010): For the enzyme inhibition assay, human recombinant protein material was used (human HDAC2 (CAT #: HDAC2), human HDAC6 (CAT #: HDAC6) or human HDAC8 (CAT #: HDAC8)). A 10-point dose response curve was prepared using a 3-fold dilution series (1:3), started at a concentration of 1 μM in DMSO for the synthesized drugs and 10 μM in DMSO for the reference substance Trichostatin A231 (TSA, for HDAC 2, 6 and 8). Reaction time was 90 minutes at 37° C. in a volume of 50 μL in a 96 well plate. Reaction buffer: 50 mM Tris-HCl, pH=8.0, 137 mM NaCl, 2.7 mM KCl, and 1 mM MgCl$_2$ freshly added: 1 mg/ml bovine serum albumin. The fluorescence was measured using a fluoroscope Ascent™ FL fluorometer. The percent enzyme activity was calculated relative to the DMSO control. IC$_{50}$ values were calculated using GraphPad Prism (GraphPad Prism 4.0 Software, San Diego, USA) based on a sigmoidal dose-response equation.

Purity Controls and Determination of the Enantiomeric Excess by Analytical HPLC were performed with a Waters GmbH (Eschborn, Germany) system, equipped with a Waters 1525 Binary HPLC pump, a Waters 2707 autosampler and a Waters 2998 UV-Vis detector. The column used was a Hibar 125-4, Purospher rp 18e, 3 μm from Merck KGaA, the evaluation was carried out with the software Empower 3, 2010 (Waters GmbH, Eschborn, Germany).

By determining the percentage of area peaks at 220 nm, the purity of the samples could be determined. The column temperature was always 10° C. for compounds measured with this instrument.

Method A

|    | Time [min] | Flow rate [mL/min] | % A  | % B  |
|----|-----------|--------------------|------|------|
| 1. | —         | 0.80               | 80.0 | 20.0 |
| 2. | 30.0      | 0.80               | 20.0 | 80.0 |
| 3. | 31.0      | 0.80               | 5.0  | 95.0 |
| 4. | 40.0      | 0.80               | 5.0  | 95.0 |
| 5. | 41.0      | 0.80               | 80.0 | 20.0 |
| 6. | 50.0      | 0.80               | 80.0 | 20.0 |

Method B

|    | Time [min] | Flow rate [mL/min] | % A  | % B  |
|----|-----------|--------------------|------|------|
| 1. | —         | 0.80               | 95.0 | 5.0  |
| 2. | 30.0      | 0.80               | 20.0 | 80.0 |
| 3. | 31.0      | 0.80               | 2.0  | 98.0 |
| 4. | 40.0      | 0.80               | 2.0  | 98.0 |
| 5. | 41.0      | 0.80               | 95.0 | 5.0  |
| 6. | 50.0      | 0.80               | 95.0 | 5.0  |

Eluent A: 0.1% formic acid+water, eluent B: 0.1% formic acid+acetonitrile. Injection volume: 10 [μL]. The detection was carried out at a wavelength of 220 nm.

Example 1: Synthesis of Compound 21 According to Scheme 1A

Scheme 1A: Synthesis of compound 21 with 15, 17, 18, 20 as examples.

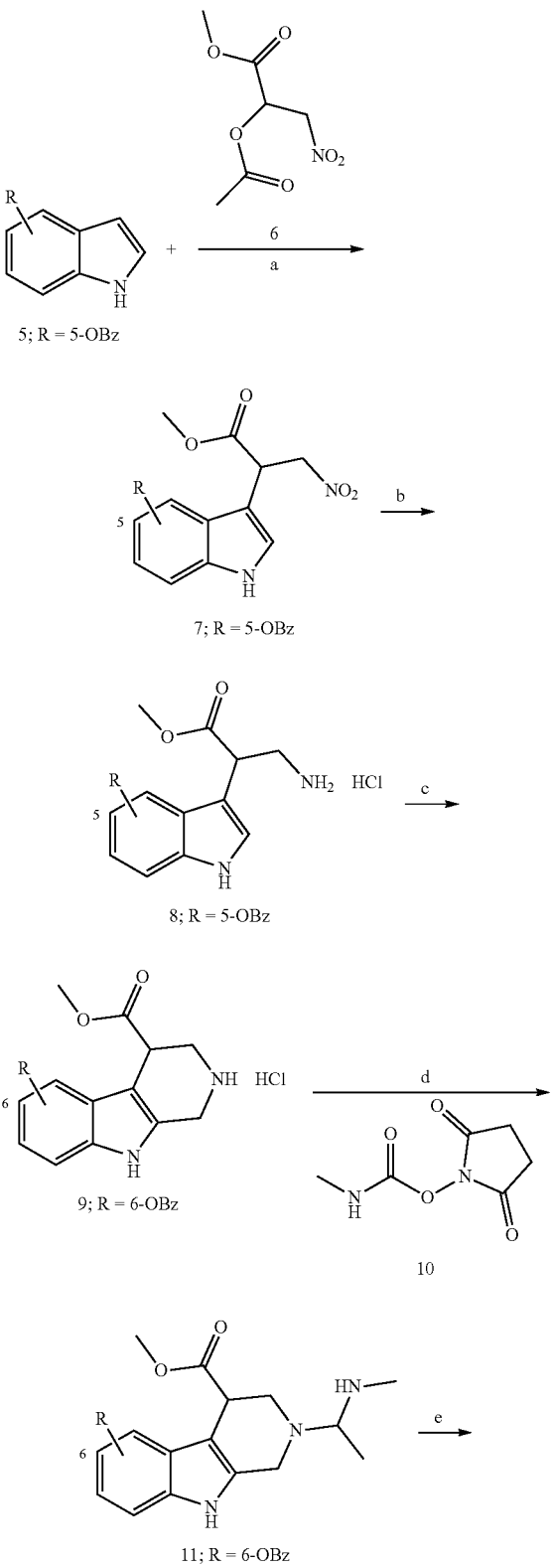

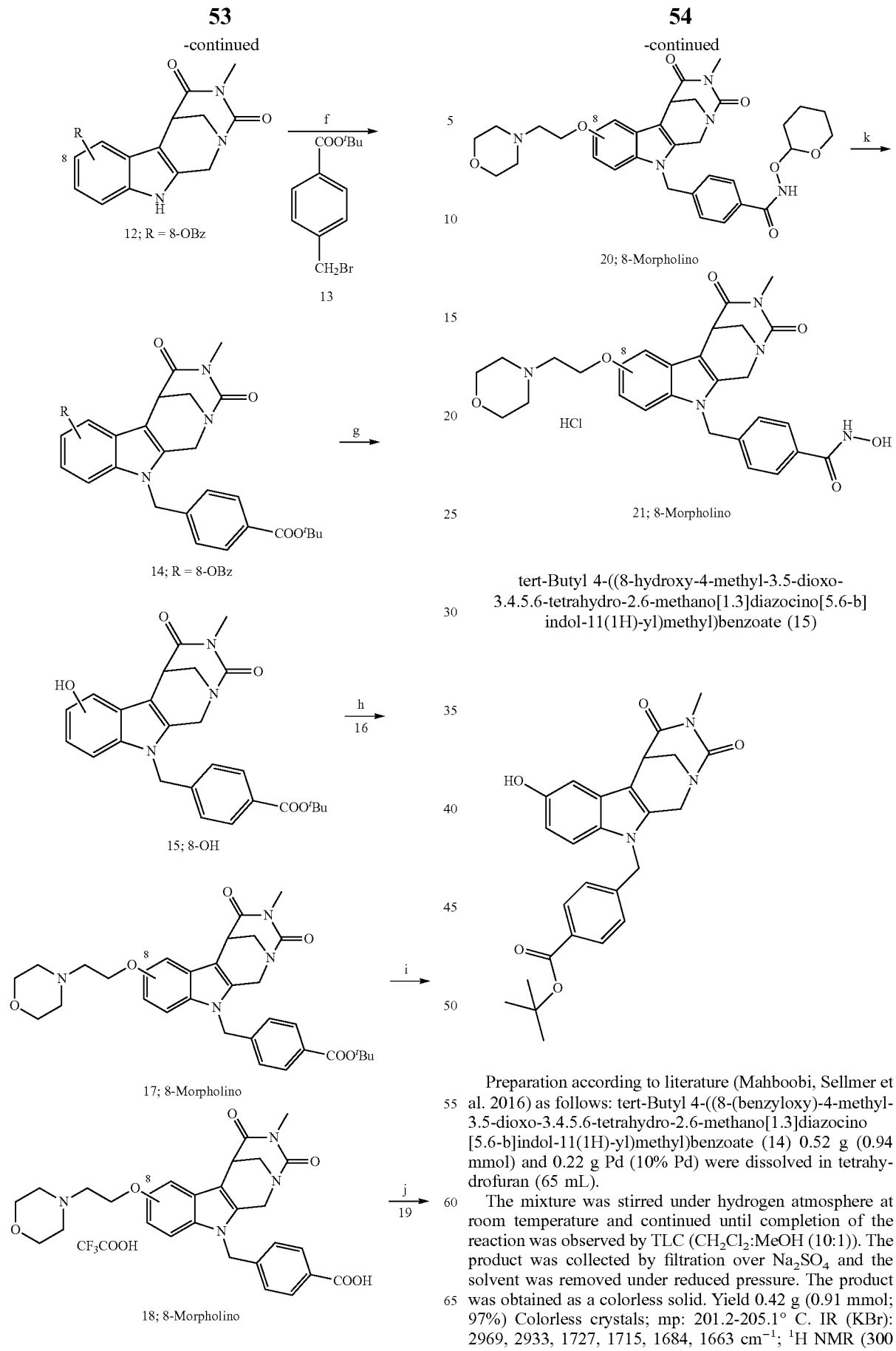

tert-Butyl 4-((8-hydroxy-4-methyl-3.5-dioxo-3.4.5.6-tetrahydro-2.6-methano[1.3]diazocino[5.6-b]indol-11(1H)-yl)methyl)benzoate (15)

Preparation according to literature (Mahboobi, Sellmer et al. 2016) as follows: tert-Butyl 4-((8-(benzyloxy)-4-methyl-3.5-dioxo-3.4.5.6-tetrahydro-2.6-methano[1.3]diazocino [5.6-b]indol-11(1H)-yl)methyl)benzoate (14) 0.52 g (0.94 mmol) and 0.22 g Pd (10% Pd) were dissolved in tetrahydrofuran (65 mL).

The mixture was stirred under hydrogen atmosphere at room temperature and continued until completion of the reaction was observed by TLC ($CH_2Cl_2$:MeOH (10:1)). The product was collected by filtration over $Na_2SO_4$ and the solvent was removed under reduced pressure. The product was obtained as a colorless solid. Yield 0.42 g (0.91 mmol; 97%) Colorless crystals; mp: 201.2-205.1° C. IR (KBr): 2969, 2933, 1727, 1715, 1684, 1663 cm$^{-1}$; $^1$H NMR (300

MHz, DMSO): δ 8.89 (s, 1H), 7.81 (d, J=8.3 Hz, 2H), 7.16 (t, J=8.2 Hz, 3H), 6.86 (d, J=2.3 Hz, 1H), 6.58 (dd, J=8.8, 2.3 Hz, 1H), 5.34 (s, 2H), 4.78 (d, J=16.5 Hz, 1H), 4.49 (d, J=16.4 Hz, 1H), 3.86 (d, J=12.9 Hz, 1H), 3.75 (s, 1H), 3.42 (dd, 1H), 2.89 (s, 3H), 1.51 (s, 9H). ESI-MS m/z (%): 406.14 [MH$^+$-C$_4$H$_8$] (100), 462.20 [MH$^+$] (16.77), 479.23 [MNH$_4$+] (39.69), 945.38 [MNa$^+$] (4.89). Anal. calcd for C$_{26}$H$_{27}$N$_3$O$_5$: C, 67.66; H, 5.90; N, 9.10; found: C, 67.41; H, 5.98; N, 8.84.

tert-Butyl 4-((4-methyl-8-(2-morpholinoethoxy)-3,5-dioxo-3,4,5,6 tetrahydro-2,6-methano[1,3]diazocino[5,6-b]indol-11(1H)-yl)methyl)benzoate (17)

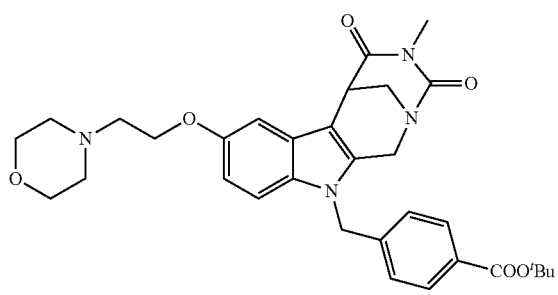

A stirred mixture of 15 (0.28 g, 0.61 mmol), 4-(2-chloroethyl)morpholine hydrochloride (16) (0.15 g, 0.81 mmol) and K$_2$CO$_3$ (0.42 g, 3.0 mmol) in 2-butanone (30.0 mL) was heated till reflux for 4 d.
The mixture was cooled to room temperature, the solid filtered off and the solvent removed under reduced pressure. After purification by cc (SiO$_2$; CH$_2$Cl$_2$, MeOH 10:1) and removal of the solvent under reduced pressure the product (0.24 g, 0.42 mmol, 68%) was obtained as a colorless solid. mp.: 204.7-208.0° C.; IR (KBr): 2857, 1714, 1687 cm$^{-1}$; $^1$H NMR (300 MHz, CDCl$_3$) δ 7.91 (d, J=8.3 Hz, 2H), 7.15 (d, J=2.3 Hz, 1H), 7.09 (d, J=9.0 Hz, 1H), 7.03 (d, J=8.3 Hz, 2H), 6.83 (dd, J=8.9, 2.4 Hz, 1H), 5.34-5.22 (m, 1H), 5.09 (d, J=17.0 Hz, 1H), 4.84 (d, J=16.4 Hz, 1H), 4.25 (d, J=15.7 Hz, 3H), 3.89 (d, J=13.3 Hz, 1H), 3.83 (d, J=8.0 Hz, 5H), 3.32 (dd, J=13.1, 2.1 Hz, 1H), 3.06 (s, 3H), 2.93 (s, 2H), 2.72 (s, 4H), 1.56 (s, 9H). ESI-MS m/z (%): 575.29 [MH$^+$] (100), 1171.55 [2MNa$^+$] (0.3). Anal. calcd for C$_{32}$H$_{38}$N$_4$O$_6$×0.25 H$_2$O: C, 66.36; H, 6.70; N, 9.67; found: C, 65.98; H, 6.58; N, 9.43.

4-(2-((11-(4-Carboxybenzyl)-4-methyl-3,5-dioxo-1,3,4,5,6,11-hexahydro-2,6-methano[1,3]diazocino[5,6-b]indol-8-yl)oxy)ethyl)morpholin-4-ium 2,2,2-trifluoroacetate (18)

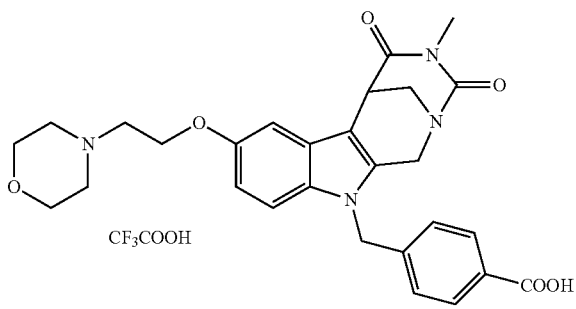

tert-Butyl 4-((4-methyl-8-(2-morpholinoethoxy)-3,5-dioxo-3,4,5,6-tetrahydro-2,6-methano[1,3]diazocino[5,6-b]indol-11(1H)-yl)methyl)benzoate (17) (0.82 g, 1.43 mmol) was dissolved in CH$_2$Cl$_2$ (25 mL) and trifluoro acetic acid (10.0 mL) was added. The mixture was stirred at room temperature (2 h) and the solvent and excess of trifluoro acetic acid removed under reduced pressure.
Yield 0.90 g (1.42 mmol, 99%) slightly yellow crystals; mp: 182.9-184.0° C. IR (KBr): 3441, 1642 cm$^{-1}$; $^1$H NMR (300 MHz, DMSO) δ 12.98 (s, 1H), 9.95 (s, 1H), 7.85 (d, J=8.3 Hz, 2H), 7.36 (d, J=8.9 Hz, 1H), 7.13 (d, J=8.3 Hz, 2H), 7.10 (d, J=2.4 Hz, 1H), 6.85 (dd, J=8.9, 2.4 Hz, 1H), 5.43 (s, 2H), 4.82 (d, J=16.6 Hz, 1H), 4.54 (d, J=16.5 Hz, 1H), 4.34 (s, 2H), 3.99 (d, J=11.3 Hz, 2H), 3.91 (d, J=12.7 Hz, 1H), 3.83 (s, 1H), 3.71 (t, J=11.9 Hz, 2H), 3.64-3.49 (m, 4H), 3.45 (d, J=11.3 Hz, 1H), 3.23 (s, 2H), 2.90 (s, 3H). ESI-MS m/z (%): 519.23 [MH$^+$] (100), 1059.42 [2MNa$^+$] (0.03). Anal. calcd for C$_{30}$H$_{31}$F$_3$N$_4$O$_8$: C, 56.96; H, 4.94; N, 8.86; found: C, 56.88; H, 5.05; N, 8.56.

4-((4-Methyl-8-(2-morpholinoethoxy)-3,5-dioxo-3,4,5,6-tetrahydro-2,6-methano[1,3]diazocino[5,6-b]indol-11(1B)-yl)methyl)-N—((tetrahydro-2H-pyran-2-yl)oxy)benzamide (20)

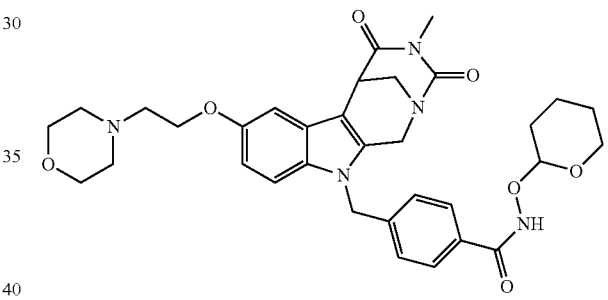

A mixture of 4-(2-((11-(4-carboxybenzyl)-4-methyl-3,5-dioxo-1,3,4,5,6,11-hexahydro-2,6-methano[1,3]diazocino [5,6-b]indol-8-yl)oxy)ethyl)morpholin-4-ium 2,2,2-trifluoroacetate (18) (0.63 g; 1.00 mmol), BOP (0.53 g, 1.20 mmol) diisopropylethylamine (0.52 mL, 3.00 mmol) and O-(tetrahydro-2H-pyran-2-yl)hydroxylamine (19) in THF was stirred at room temperature overnight. The mixture was poured into water, extracted with ethyl acetate (3×50 mL), the combined organic layers dried (Na$_2$SO$_4$), the solvent removed and the product purified by cc (SiO$_2$, CH$_2$Cl$_2$, MeOH 20:1). Yield 0.66 g (1.00 mmol, 99%) colorless foam. mp.: 135.7-138.0° C.; IR (KBr): 3433, 1729, 1684 cm$^{-1}$; $^1$H NMR (300 MHz, DMSO) δ 11.60 (s, 1H), 7.67 (d, J=8.3 Hz, 2H), 7.29 (d, J=8.9 Hz, 1H), 7.12 (d, J=8.3 Hz, 2H), 7.00 (d, J=2.4 Hz, 1H), 6.75 (dd, J=8.9, 2.4 Hz, 1H), 5.37 (s, 2H), 4.95 (s, 1H), 4.82 (d, J=16.6 Hz, 1H), 4.53 (d, J=16.4 Hz, 1H), 4.13-3.98 (m, 3H), 3.89 (d, J=12.8 Hz, 1H), 3.84 (s, 1H), 3.59 (d, J=4.6 Hz, 3H), 3.57 (s, 2H), 3.53-3.39 (m, 2H), 2.89 (s, 3H), 2.70 (t, J=5.7 Hz, 2H), 2.54 (s, 2H), 1.61 (d, J=49.1 Hz, 6H), 1.17 (t, J=7.1 Hz, 1H); ESI-MS m/z (%): 618.29 [MH$^+$] (100).

4-(2-((11-(4-(Hydroxycarbamoyl)benzyl)-4-methyl-3,5-dioxo-1,3,4,5,6,11-hexahydro-2,6-methano[1,3]diazocino[5,6-b]indol-8-yl)oxy)ethyl)morpholin-4-ium chloride (21)

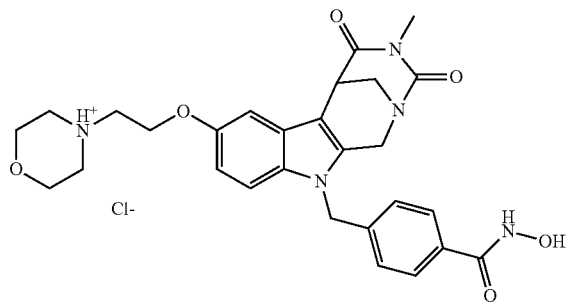

To a stirred solution of 4-((4-methyl-8-(2-morpholinoethoxy)-3,5-dioxo-3,4,5,6-tetrahydro-2,6-methano[1,3]diazocino[5,6-b]indol-11(1H)-yl)methyl)-N—((tetrahydro-2H-pyran-2-yl)oxy)benzamide (20) (1.15 g, 1.86 mmol) in $CH_2Cl_2$ (40.0 mL) HCl in iso-propanol (1.50 mL, 5-6N) was added dropwise. After 2 h the resulting solid was allowed to precipitate, the solvent decanted and the solid dissolved in the necessary amount of MeOH. The solution obtained was added dropwise to a mixture of light petrol/$Et_2O$ whilst stirring, the precipitating solid removed by filtration and the slightly wet solid died in vacuo. Yield 0.80 g (1.40 mmol, 75%) pale yellow solid. mp: 158.4-162.0° C. IR (KBr): 3433, 1671, 1468 $cm^{-1}$; $^1H$ NMR (300 MHz, DMSO) δ 11.19 (s, 1H), 10.96 (s, 1H), 9.53-8.49 (m, 1H), 7.66 (d, J=8.3 Hz, 2H), 7.35 (d, J=8.9 Hz, 1H), 7.10 (d, J=8.3 Hz, 2H), 7.07 (d, J=2.4 Hz, 1H), 6.83 (dd, J=8.9, 2.4 Hz, 1H), 5.41 (d, J=18.6 Hz, 2H), 4.84 (d, J=16.6 Hz, 1H), 4.56 (d, J=16.6 Hz, 1H), 4.39 (d, J=4.6 Hz, 2H), 3.97 (d, J=12.4 Hz, 2H), 3.90 (d, J=12.9 Hz, 1H), 3.78 (d, J=11.4 Hz, 1H), 3.54 (d, J=8.0 Hz, 3H), 3.48 (s, 2H), 3.41 (d, J=3.1 Hz, 4H), 2.90 (s, 3H). ESI-MS m/z (%): 534.24 [$MH^+$] (100). Anal. calcd for $C_{28}H_{32}ClN_5O_6$+1.75 $H_2O$: C, 55.90; H, 5.95; N, 11.64; found: C, 55.99; H, 5.84; N, 11.26.

Scheme 1B: Enantioselective synthesis of (R)-21 and (S)-21

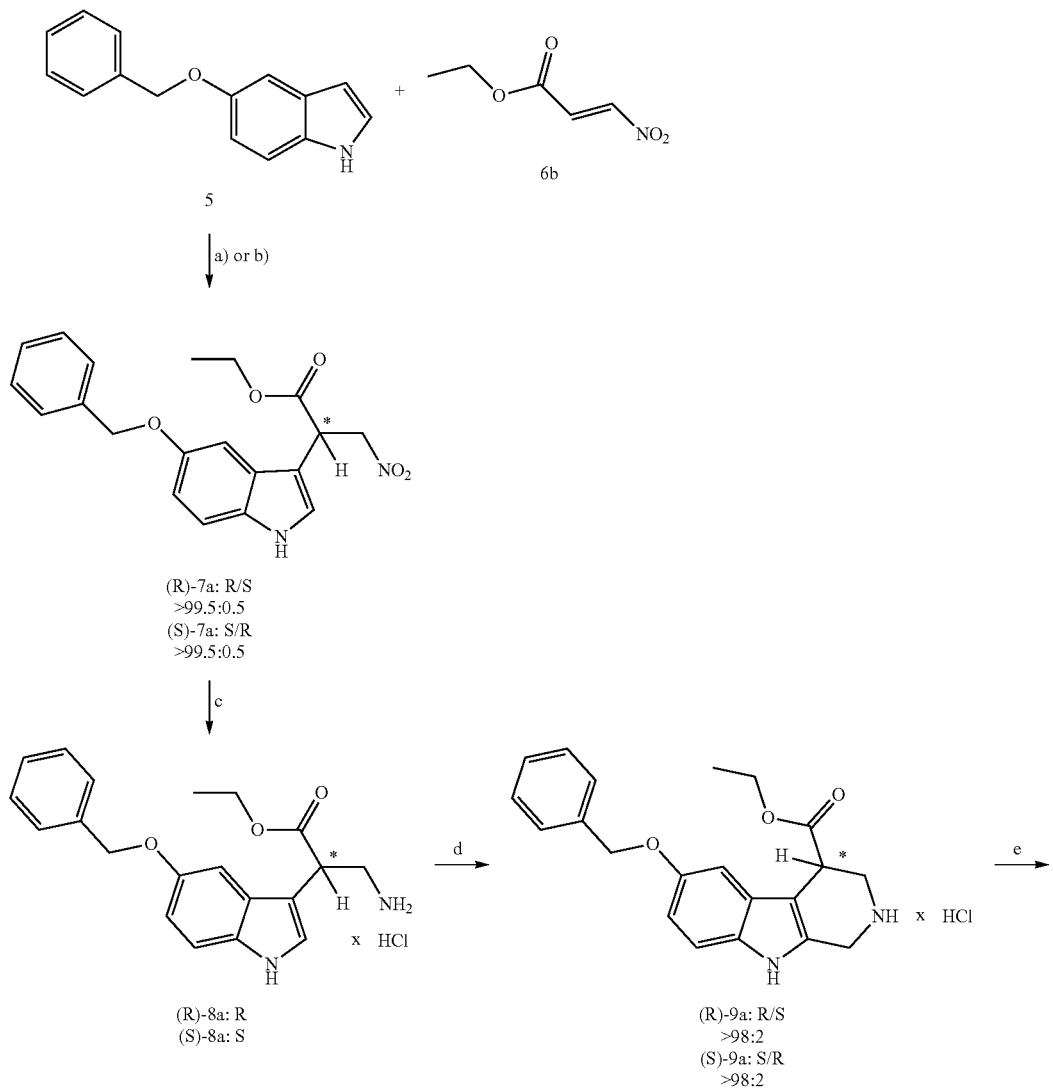

-continued
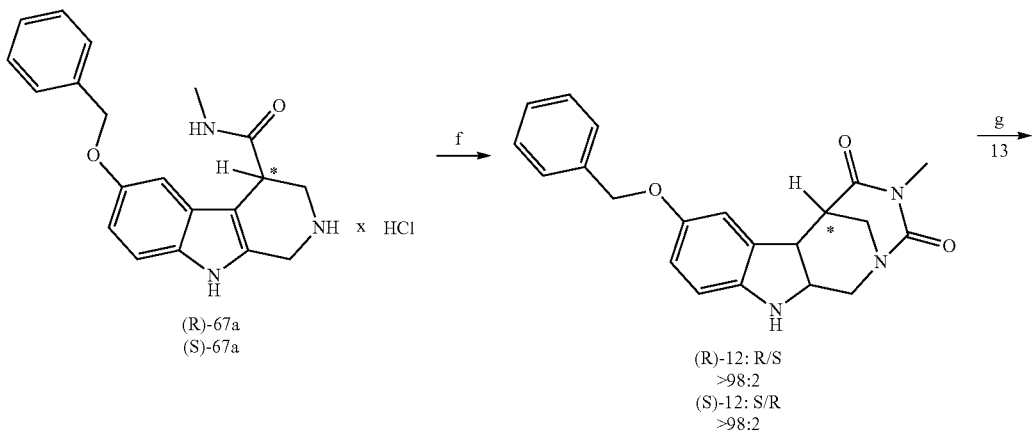
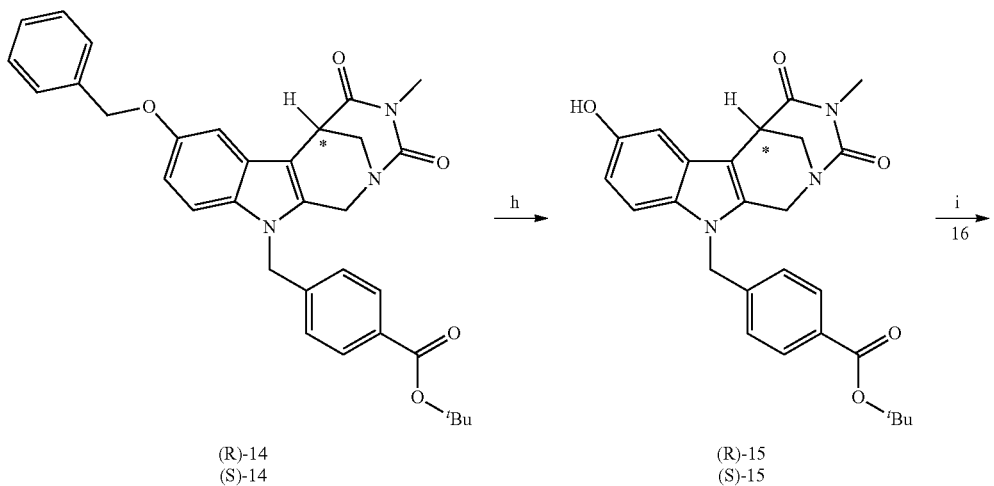
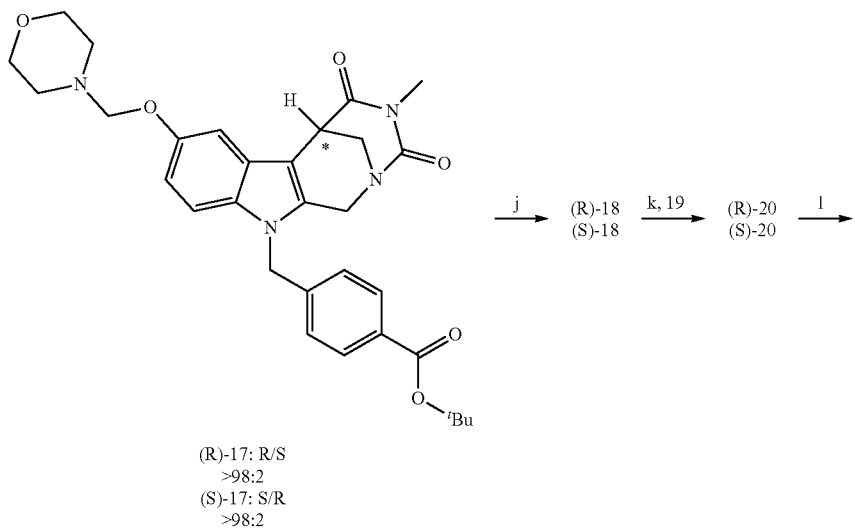

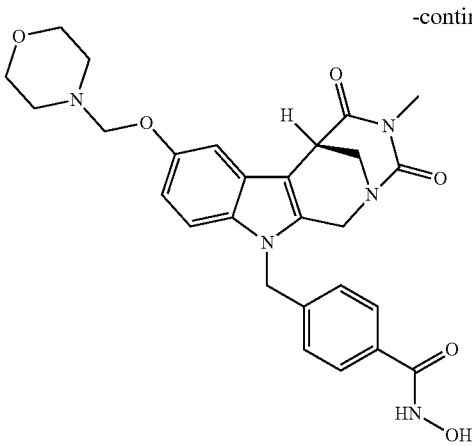

(R)-21

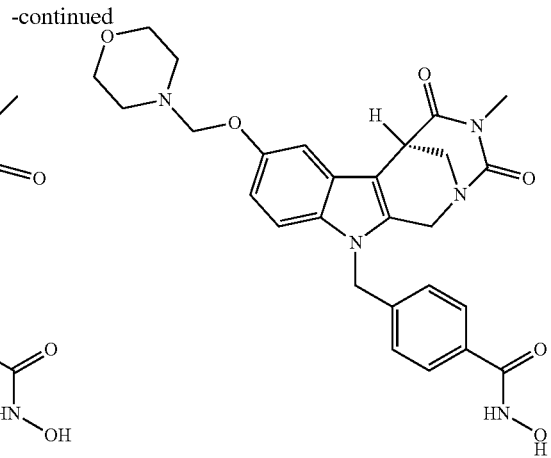

(S)-21

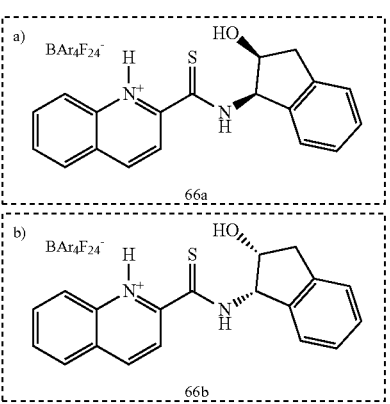

BAr₄F₂₄⁻ = tetrakis[3,5-bis(trifluoromethyl)phenyl]borate

Synthesis of the S-Enantiomer:

Ethyl (S)-2-(5-(benzyloxy)-1H-indole-3-yl)-3-nitropropanoate ((S)-7a)

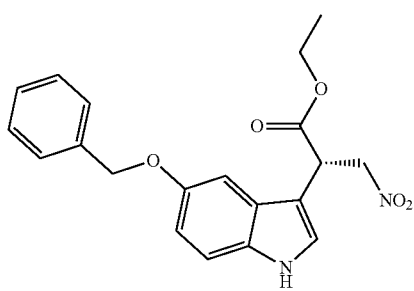 [SMILES: CCOC(=O)[C@H](C[N+](=O)[O-])c1c[nH]c2ccc(OCc3ccccc3)cc12]

From 5-(benzyloxy)-1H-indol (6) (2.79 g, 12.50 mmol) as described by Sellmer et al. (Sellmer, Stangl et al. 2018). The product was purified by cc (SiO$_2$; CH$_2$Cl$_2$, n-hexane, EtOAc 1:5:1). Yield 3.00 g (8.15 mmol, 65%) yellow oil. IR (ATR, attenuated total reflection): 1726; 1552 cm$^{-1}$. $^1$H NMR (300 MHz, DMSO-d$_6$) δ 11.07 (s, 1H), 7.49 (d, J=6.9 Hz, 2H), 7.44-7.32 (m, 3H), 7.28 (m, 3H), 6.85 (dd, J=8.8, 2.4 Hz, 1H), 5.24 (dd, J=15.0, 10.7 Hz, 1H), 5.11 (s, 2H), 4.90 (dd, J=15.1, 4.8 Hz, 1H), 4.67 (dd, J=10.6, 4.7 Hz, 1H), 4.21-3.95 (m, 2H), 1.12 (t, J=7.1 Hz, 3H). ee determination: HPLC with a Chiralcel OD-H column, hexane/2-propanol (90:10), flow rate=0.6 mL/min, 220 fn. t$_R$=134.5 min(major), 152.5, min (minor), ≥99% ee, [α]$^{20}_{259}$ +134.093 (c 0.1; MeOH). HRMS (ESI-MS) m/z: calcd: 369.1445 [MH$^+$], found: 369.1445 [MH$^+$]. RP (reversed phase)-HPLC (220 nm, Method A): 100.0%, t$_R$=21.6 min.

Ethyl (S)-3-amino-2-(5-(benzyloxy)-1H-indole-3-yl)propanoate hydrochloride ((S)-8a)

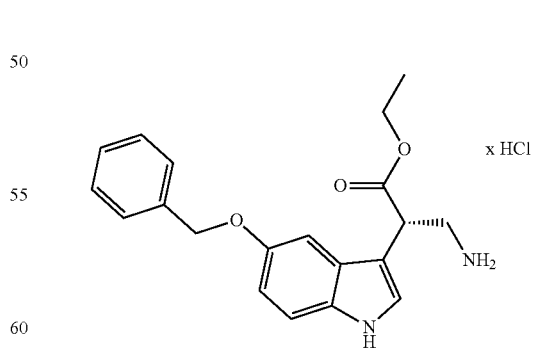

From ethyl (S)-2-(5-(benzyl oxy)-1H-indole-3-yl)-3-nitropropanoate ((S)-7a) (4.90 g, 13.31 mmol) as described by Sellmer et al. (Sellmer, Stangl et al. 2018). Yield 4.12 g (10.99 mmol; 83%) colorless foam. IR (ATR): 3400; 2908; 1721 cm$^{-1}$. $^1$H NMR (300 MHz, DMSO-d$_6$) δ 11.10 (d, J=2.1 Hz, 1H), 8.11 (m, 3H), 7.48 (d, J=6.9 Hz, 2H), 7.44-7.28 (m, 4H), 7.24 (dd, J=14.5, 2.4 Hz, 2H), 6.86 (dd, J=8.8, 2.3 Hz, 1H), 5.10 (s, 2H), 4.25 (t, 0.1=7.2 Hz, 1H), 4.09 (q, J=10.8, 7.1 Hz, 2H), 3.52-3.40 (m, 1H), 3.19-3.06 (m, 1H), 1.13 (t, J=7.1 Hz, 3H). $[\alpha]^{20}_{589}$ −69.3 (c 0.1; MeOH). HRMS ($C_{20}H_{22}N_2O_3$, ESI-MS) m/z: calcd.: 339.1703 [MH$^+$], found.: 339.1703 [MH$^+$]. RP-HPLC (220 nm, Method A): 99.3%, $t_R$=7.2 min.

Ethyl (S)-6-(benzyloxy)-2,3,4,9-tetrahydro-1H-pyrido[3,4-b]indole-4-carboxylate hydrochloride ((S)-9a)

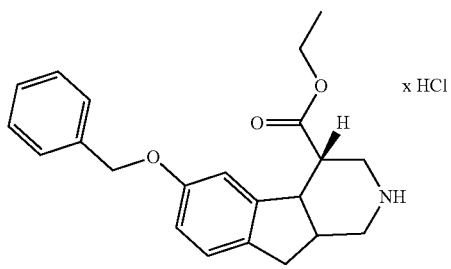 [SMILES: CCOC(=O)[C@@H]1CNCC2Cc3ccc(OCc4ccccc4)cc3C21]

From ethyl (S)-3-amino-2-(5-(benzyloxy)-1H-indol-3-yl)propanoate hydrochlorid ((S)-8a) (4.12 g, 10.99 mmol) as by Sellmer et al. (Sellmer, Stangl et al. 2018). Yield 2.82 g (7.29 mmol, 66%). mp.: 262.7° C. IR (KBr): 2922; 2797; 1719 cm$^{-1}$. $^1$H NMR (400 MHz, DMSO-d$_6$) δ 11.19 (s, 1H), 10.10 (s, 1H), 9.08 (s, 1H), 7.47-7.41 (m, 2H), 7.41-7.35 (m, 2H), 7.34-7.27 (m, 2H), 7.12 (d, J=2.3 Hz, 1H), 6.85 (dd, J=8.8, 2.4 Hz, 1H), 5.07 (q, J=12.0 Hz, 2H), 4.37-4.25 (m, 2H), 4.16 (d, J=2.6 Hz, 1H), 4.15-4.04 (m, 2H), 3.67 (d, J=9.7 Hz, 1H), 3.49 (d, J=12.0 Hz, 1H), 1.19 (t, J=7.1 Hz, 3H). ee was determination: HPLC with a Chiralcel OD-H column, hexane/2-propanol (90:10), flow rate=0.6 mL/min, 220 nm. $t_R$=83.3 min (major), 110.2 min (minor), ≥96% ee, $[\alpha]^{20}_{589}$ −126.5 (c 0.1; MeOH). HRMS ($C_{21}H_{22}N_2O_3$, ESI-MS) m/z: calcd.: 351,1703 [MH$^+$], found: 351.1705 [MH$^+$]. RP-HPLC (220 nm, Method A): 99.4%, $t_R$=8.0 min.

(S)-6-(Benzyloxy)-N-methyl-2,3,4,9-tetrahydro-1H-pyrido[3,4-b]indole-4-carboxamide hydrochloride ((S)-67a)

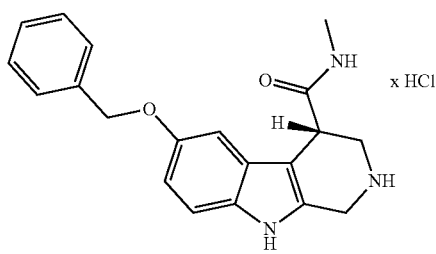 [SMILES: CNC(=O)[C@@H]1CNCc2[nH]c3ccc(OCc4ccccc4)cc3c21]

Ethyl (S)-6-(benzyloxy)-2,3,4,9-tetrahydro-1H-pyrido[3,4-b]indol-4-carboxylat hydrochlorid ((S)-9a) (0.40 g, 1.03 mmol) was dissolved in a mixture of DCM/MeOH (1:1; 10 mL), DMSO (8 drops), DMF (6.9 mL) and a methanolic methylamine solution (30%, 19 mL) at 0° C. After adding of a catalytic amount of NaCN (0.304 g) it was stirred for 6 d. Purification by cc (SiO$_2$; CH$_2$Cl$_2$, MeOH, NH$_3$ $_{conz}$ 50:10:0.1) (dry load technique) yielded 0.254 g (0.68 mmol; 66%) colorless crystals. mp.: 178.4° C. IR (KBr): 2940, 1637 cm$^{-1}$. $^1$H NMR (300 MHz, DMSO-d$_6$) δ 10.65 (s, 1H), 7.92 (m, 1H), 7.46 (d, J=7.0 Hz, 2H), 7.42-7.31 (m, 3H), 7.17 (d, 0.1=8.7 Hz, 1H), 6.99 (d, J=2.3 Hz, 1H), 6.73 (dd, J=8.7, 2.4 Hz, 1H), 5.04 (s, 2H), 3.91-3.75 (m, 2H), 3.44 (d, J=4.2 Hz, 1H), 3.11 (dd, J=13.0, 4.1 Hz, 1H), 2.94 (dd, J=12.9, 4.8 Hz, 1H), 2.58 (d, J=4.5 Hz, 3H). $[\alpha]^{20}_{589}$ −35.6 (c 0.1; MeOH). HRMS ($C_{20}H_{21}N_3O_2$, ESI-MS) m/z: calcd.: 336.1707 [MH$^+$], found: 336.1705 [MH$^+$]. RP-HPLC (220 nm, Method A): 98.7%, $t_R$=6.2 min.

(6S)-8-(Benzyloxy)-4-methyl-6,11-dihydro-2,6-methano[1,3]diazocino[5,6-b]indole-3,5(1H,4H)-dione ((S)-12)

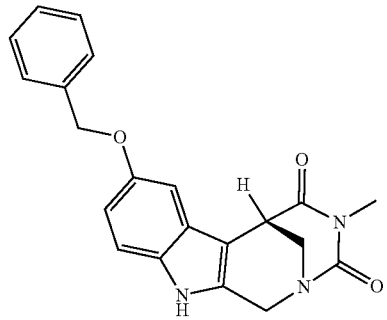 [SMILES: CN1C(=O)[C@@H]2CN(Cc3[nH]c4ccc(OCc5ccccc5)cc4c32)C1=O]

From 6-(benzyloxy)-N-methyl-2,3,4,9-tetrahydro-1H-pyrido[3,4-b]indole-4-carboxamide ((S)-67a) after release of the base with dilut. NH$_3$-Lösung (0.163 g, 0.44 mmol) following Sellmer et al. (Sellmer, Stangl et al. 2018). Purification by cc (SiO$_2$; EE) (dry load technique) yielded 0.128 g (0.35 mmol; 80%) colorless crystals. mp.: 273.6° C. IR (KBr): 3281; 1730; 1673 cm$^{-1}$. $^1$H NMR (400 MHz, CDCl$_3$) δ 8.03 (s, 1H, N<u>H</u> (Indole)), 7.50-7.45 (m, 2H, Ar—<u>H</u>), 7.42-7.30 (m, 3H, Ar—<u>H</u>), 7.23-7.19 (m, 2H, Ar—<u>H</u>), 6.92 (dd, J=8.8, 2.4 Hz, 1H, Ar—<u>H</u>), 5.10 (d, J=3.2 Hz, 2H, OC<u>H</u>$_2$), 4.87 (d, J=16.3 Hz, 1H, NC<u>H</u>$_A$H$_B$C), 4.50 (d, J=16.3 Hz, 1H, NC<u>H</u>$_A$H$_B$C), 3.90 (d, J=13.1 Hz, 1H, NC<u>H</u>$_A$H$_B$CH), 3.83 (br s, 1H, NCH$_2$C<u>H</u>), 3.37 (dd, J=13.1, 2.2 Hz, 1H, NCH$_A$<u>H</u>$_B$CH), 3.07 (s, 3H, NC<u>H</u>$_3$).

$^{13}$C NMR (101 MHz, CDCl$_3$) δ 173.23 (quart.<u>C</u>O), 161.49 (quart.<u>C</u>O), 154.03 (quart. Ar—<u>C</u>), 137.40 (quart. Ar—<u>C</u>), 132.48 (quart. Ar-<u>C</u>), 130.90 (quart. Ar—<u>C</u>), 128.53 (+, Ar—<u>C</u>H), 127.85 (+, Ar—<u>C</u>H), 127.69 (+, (Ar—<u>C</u>H)$_2$), 126.61 (quart. Ar—<u>C</u>), 113.63 (+, Ar—<u>C</u>H), 112.04 (+, Ar—<u>C</u>H), 106.47 (quart. Ar—<u>C</u>), 101.44 (+, Ar—<u>C</u>H), 70.83 (−, O<u>C</u>H$_2$), 50.23 (−, N<u>C</u>H$_2$C), 47.58 (−, N<u>C</u>H$_2$CH), 36.82 (+, Ar—<u>C</u>H), 30.95 (+, N<u>C</u>H$_2$CH), 27.89 (+, N<u>C</u>H$_3$). $[\alpha]^{20}_{589}$ −27.4 (c 0.1; MeOH). HRMS ($C_{21}H_{19}N_3O_3$, ESI-MS) m/z: calcd.: 362.1499 [MH$^+$], found: 362.1498 [MH$^+$]. RP-HPLC (220 nm, Method A): 99.5%, $t_R$=18.2 min.

tert-Butyl 4-(((6S)-8-(benzyloxy)-4-methyl-3,5-dioxo-3,4,5,6-tetrahydro-2,6-methano[1,3]diazocino[5,6-b]indole-11(1H)-yl)methyl)benzoate ((S)-14)

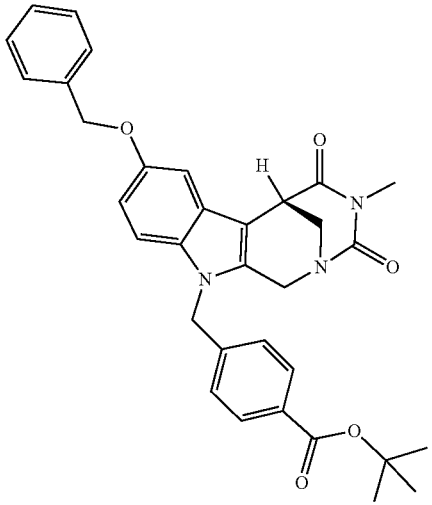 [SMILES: CN1C(=O)[C@@H]2CN(Cc3c2c2cc(OCc4ccccc4)ccc2n3Cc2ccc(C(=O)OC(C)(C)C)cc2)C1=O]

A stirred mixture of 8-(benzyloxy)-4-methyl-6,11-dihydro-2,6-methano[1,3]diazocino[5,6-b]indole-3,5(1H, 4H)-dione ((S)-12) (0.127 g; 0.35 mmol), tert-butyl 4-(bromomethyl)benzoate (13) (0.103 g, 0.38 mmol) und $K_2CO_3$ (0.243 g, 1.76 mmol) in 2-butanone (5.20 mL), was heated to 80° C. for 16 h. The mixture was cooled to rt, the solid filtered off and the solvent removed i.vac. After purification by cc ($SiO_2$; $CH_2Cl_2$, EtOAc 3:1) and removal of the solvent i.vac. the product (0.16 g, 0.29 mmol, 83%), yellow oil. IR (ATR): 1710, 1685 cm$^{-1}$. $^1$H NMR (300 MHz, CDCl$_3$) δ 7.99 (dd, J=8.5, 2.3 Hz, 1H), 7.92 (d, J=8.3 Hz, 1H), 7.51-7.46 (m, 2H), 7.43-7.32 (m, 4H), 7.07 (m, 3H), 6.91 (dd, J=8.9, 2.4 Hz, 1H), 5.30 (d, J=17.0 Hz, 1H), 5.15 (m, 1H), 5.11 (d, J=2.7 Hz, 2H), 4.85 (d, J=16.4 Hz, 1H), 4.26 (d, J=16.4 Hz, 1H), 3.90 (d, J=13.0 Hz, 2H), 3.40-3.27 (m, 1H), 3.07 (s, 3H), 1.57 (s, 9H). [α]$^{20}_{589}$ −24.0 (c 0.1; MeOH). HRMS ($C_{33}H_{33}N_3O_5$, ESI-MS) m/z: calcd.: 574.2312 [MNa$^+$], found: 574.2317 [MNa$^+$]. RP-HPLC (220 nm, Method A): 99.0%, $t_R$=7.0 min.

tert-Butyl 4-(((6S)-8-hydroxy-4-methyl-3,5-dioxo-3,4,5,6-tetrahydro-2,6-methano[1,3]diazocino[5,6-b]indole-11(1H)-yl)methyl)benzoate ((S)-15)

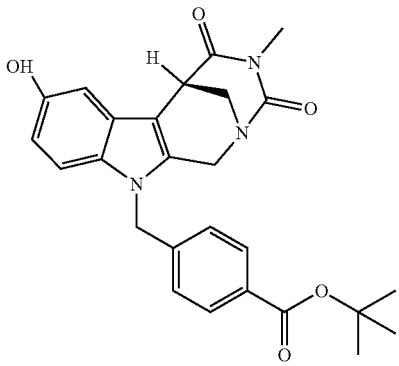 [SMILES: CN1C(=O)[C@@H]2CN(Cc3c2c2cc(O)ccc2n3Cc2ccc(C(=O)OC(C)(C)C)cc2)C1=O]

As described by Mahboobi et al. (Mahboobi, Teller et al. 2002) to a solution of tert-butyl 4-((8-(benzyloxy)-4-methyl-3,5-dioxo-3,4,5,6-tetrahydro-2,6-methano[1,3]diazocino[5,6-b]indole-11(1H)-yl)methyl) benzoate ((S)-14) (0.155 g, 0.28 mmol) in THF/MeOH (2:1) Pd/C 10% (0.049 g) and ammonium formiate (0.29 g, 4.6 mmol) were added, and the mixture was stirred for 20 min at 75° C. After filtration of Pd/C, purification cc ($CH_2Cl_2$, EtOAc (3:1)) yielded (0.100 g, 0.22 mmol, 79%) colorless crystals. mp.: 206.3° C. IR (KBr): 3416, 1715, 1663 cm$^{-1}$. $^1$H NMR (400 MHz, DMSO-d$_6$) δ 8.86 (s, 1H), 7.79 (d, J=8.3 Hz, 2H), 7.14 (m, 3H), 6.85 (d, J=2.3 Hz, 1H), 6.57 (dd, J=8.8, 2.3 Hz, 1H), 5.33 (s, 2H), 4.76 (d, J=16.5 Hz, 1H), 4.48 (d, J=16.4 Hz, 1H), 3.85 (d, J=12.6 Hz, 1H), 3.74 (br s, 1H), 3.40 (dd, J=13.2, 2.2 Hz, 1H), 2.88 (s, 3H), 1.50 (s, 9H). [α]$^{20}_{589}$ 89.5 (c 0.1; MeOH). HRMS ($C_{26}H_{27}N_3O_5$, ESI-MS) m/z: calcd.: 484.1843 [MNa$^+$], found:484.1841 [MNa$^+$]. Anal. ($C_{26}H_{27}N_3O_5$) calcd: C, 67.66; H, 5.90; N, 9.10; found: C, 67.48; H, 6.06; N, 8.88.

tert-Butyl 4-(((6S)-4-methyl-8-(2-morpholinoethoxy)-3,5-dioxo-3,4,5,6-tetrahydro-2,6-methano[1,3]diazocino[5,6-b]indole-11(1H)-yl)methyl)benzoate $C_{32}H_3N_4O_6$ (MW=574.68 g/mol) ((S)-17)

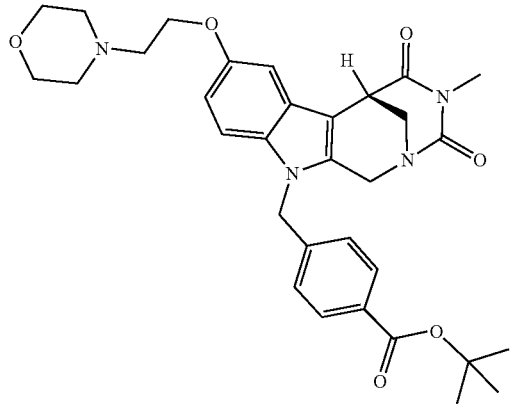 [SMILES: CN1C(=O)[C@@H]2CN(Cc3c2c2cc(OCCN4CCOCC4)ccc2n3Cc2ccc(C(=O)OC(C)(C)C)cc2)C1=O]

A mixture of (S)-15 (0.082 g, 0.18 mmol), 4-(2-chloroethyl)morpholine hydrochloride (16) (0.044 g, 0.24 mmol) und $K_2CO_3$ (0.123 g, 0.89 mmol) in 2-butanone (8.8 mL) was heated to 70° C. for 16 h. Purification by cc ($SiO_2$; $CH_2Cl_2$, EtOAc, 3.1) (dry load technique) yielded 0.067 g (0.12 mmol; 67%) colorless yellow oil. IR (ATR): 1712, 1688 cm$^{-1}$. $^1$H NMR (400 MHz, CDCl$_3$) δ 7.91 (d, J=8.3 Hz, 2H, Ar—H), 7.15 (d, J=2.4 Hz, 1H, Ar—H),7.09 (d, J=8.9 Hz, 1H, Ar—H), 7.03 (d, J=8.3 Hz, 2H, Ar—H), 6.83 (dd, J=8.9, 2.4 Hz, 1H, Ar—H), 5.33-5.24 (m, 1H, NCH$_A$H$_B$Ar), 5.09 (d, J=17.0 Hz, 1H, NCH$_A$H$_B$Ar), 4.84 (d, J=16.4 Hz, 1H, NCH$_A$H$_B$C), 4.29-4.21 (m, 3H, NCH$_A$H$_B$C, OCH$_2$CH$_2$), 3.89 (d, J=13.1 Hz, 1H, NCH$_A$H$_B$CH), 3.85 (br s, 1H, NCH$_2$CH), 3.82 (s, J=32.6 Hz, 4H, O(CH$_2$)$_2$CH$_2$N-morpholine), 3.32 (dd, J=13.1, 2.2 Hz, 1H, NCH$_A$H$_B$CH), 3.06 (s, 3H, NCH$_3$), 2.95 (m, 2H, OCH$_2$CH$_2$), 2.75 (s, 4H, O(CH$_2$)$_2$(CH$_2$)$_2$N-morpholine), 1.56 (s, 9H, OC(CH$_3$)$_3$.

$^{13}$C NMR (101 MHz, CDCl$_3$) δ 173.13 (quart.CO), 165.17 (quart.CO), 161.26 (quart.CO), 152.68 (quart.O—Ar—C), 141.02 (quart. Ar—C), 133.80 (quart. Ar—C), 131.90 (quart. Ar—C), 131.77 (quart. Ar—C), 130.20 (+, (Ar—CH)$_2$), 126.49 (quart. Ar—C), 126.07 (+, (Ar—CH)$_2$), 113.22 (+, Ar—CH), 110.44 (+, Ar—CH), 105.97 (quart. Ar—C), 101.48 (+, Ar—CH), 81.27 (quart.OC(CH$_3$)$_3$), 72.83 (−, O(CH$_2$)$_2$CH$_2$N-morpholine), 65.46 (−, OCH$_2$CH$_2$), 57.68 (−, OCH$_2$CH$_2$), 53.91 (−, O(CH$_2$)$_2$ (CH$_2$)$_2$N-morpholine), 49.46 (–, NCH$_2$C), 47.37 (–, NCH$_2$CH), 47.12 (–, NCH$_2$Ar), 36.87 (+, NCH$_2$CH), 28.36 (+, OC(CH$_3$)$_3$), 27.91 (+, NCH$_3$). [α]$^{20}_{589}$ 42.1 (c 0.1; MeOH). HRMS (C$_{32}$H$_{38}$N$_4$O$_6$, ESI-MS) m/z: calcd.: 575.2864 [MH$^+$], found: 575.2874 [MH$^+$]. RP-HPLC (220 nm, Method A): 99.7%, $t_R$=11.4 min.

4-(2-(((6S S)-11-(4-carboxybenzyl)-4-methyl-3,5-dioxo-1,3,4,5,6,11-hexahydro-2,6-methano[1,3]diazocino[5,6-b]indole-8-yl)oxy)ethyl)morpholin-4-ium 2,2,2-trifluoroacetate ((S)-18)

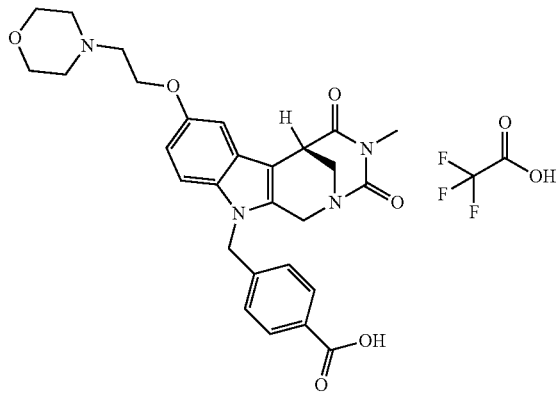

To a solution of tert-butyl 4-((4-methyl-8-(2-morpholinoethoxy)-3,5-dioxo-3,4,5,6-tetrahydro-2,6-methano[1,3]diazocino[5,6-b]indole-11(1H)-yl)methyl)benzoate ((S)-17) (0.161 g; 0.28 mmol) in CH$_2$Cl$_2$ (4.90 mL), CF$_3$COOH (1.97 mL) was added and the mixture was stirred for 20 min. at r.t. After solvent removal a slight brown oil was obtained (0.237 g, 0.37 mmol; 99%). IR (ATR): 1671; 1167 cm$^{-1}$. $^1$H NMR (400 MHz, DMSO-d$_6$) δ 9.99 (s, 1H), 7.85 (d, J=8.3 Hz, 2H), 7.36 (d, J=8.9 Hz, 1H), 7.13 (d, J=8.3 Hz, 2H), 7.10 (d, J=2.3 Hz, 1H), 6.85 (dd, J=8.9, 2.4 Hz, 1H), 5.42 (s, 2H), 4.82 (d, J=16.6 Hz, 1H), 4.54 (d, J=16.6 Hz, 1H), 4.38-4.27 (m, 4H), 4.04-3.94 (m, 3H), 3.91 (d, J=12.8 Hz, 2H), 3.83 (s, 2H), 3.47-3.42 (m, 4H), 2.90 (s, 3H). $^{19}$F NMR (377 MHz, DMSO-d$_6$) δ –73.70 (s). [α]$^{20}_{589}$ 10.7 (c 0.1; MeOH). HRMS (C$_{28}$H$_{30}$N$_4$O$_6$, ESI-MS) m/z: calcd.: 519.2238 [MH$^+$], found: 519.2238 [MH$^+$]. RP-HPLC (220 nm, Method B): 100.0%, $t_R$=10.5 min.

4-(((6S)-4-Methyl-8-(2-morpholinoethoxy)-3,5-dioxo-3,4,5,6-tetrahydro-2,6-methano[1,3]diazocino[5,6-b]indole-11(1H)-yl)methyl)-N—((tetrahydro-2H-pyran-2-yl)oxy)benzamide ((S)-20)

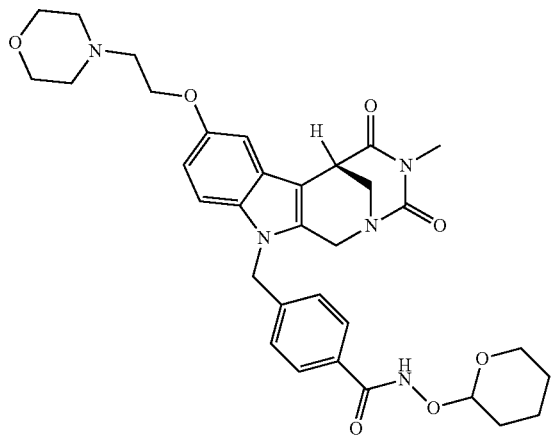 [SMILES: CN1C(=O)[C@@H]2CN(Cc3c2c2cc(OCCN4CCOCC4)ccc2n3Cc2ccc(C(=O)NOC3CCCCO3)cc2)C1=O]

From 4-((4-methyl-8-(2-morpholinoethoxy)-3,5-dioxo-3,4,5,6-tetrahydro-2,6-methano[1,3]diazocino[5,6-b]indole-1(1H)-yl)methyl)benzoic acid ((S)-18) (0.237 g, 0.46 mmol) as described by Sellmer et al. (Sellmer, Stangl et al. 2018). Purification by cc (SiO$_2$; CH$_2$Cl$_2$, MeOH, 10:1) (dry load technique) yielded 0.131 g (0.21 mmol; 77%) yellow oil. IR (ATR): 1728; 1638 cm$^{-1}$. $^1$H NMR (400 MHz, DMSO-d$_6$) δ 11.57 (s, 1H), 7.66 (d, J=8.2 Hz, 2H), 7.27 (d, J=8.9 Hz, 1H), 7.11 (d, J=8.2 Hz, 2H), 7.00 (d, J=2.3 Hz, 1H), 6.74 (dd, J=8.9, 2.4 Hz, 1H), 5.36 (s, 2H), 5.11-5.07 (m, 1H), 4.98-4.93 (m, 1H), 4.81 (d, J=16.6 Hz, 1H), 4.52 (d, J=16.6 Hz, 1H), 4.11-4.06 (m, 2H), 3.88 (d, J=12.6 Hz, 1H), 3.82 (br s, 1H), 3.60-3.57 (m, 4H), 3.56-3.52 (m, 2H), 2.88 (s, 3H), 2.77-2.71 (m, 2H), 2.40 (m, 2H), 2.32 (m, 1H), 1.70-1.55 (m, 6H). ee determination by HPLC with a Phenomenex Lux Cellulose-2 column, methanol/2-propanol (90:10), flow rate=1.0 ml/min, 220 nm. $t_R$=21.4-26.8 min (major), 38.7-43.6 min (minor), 94% ee, [α]$^{20}_{589}$ 32.0 (c 0.1; MeOH). HRMS (C$_{33}$H$_{39}$N$_5$O$_7$, ESI-MS) m/z: calcd: 618.2922[MH$^+$], found: 618.2928 [MH$^+$]. RP-HPLC (220 nm, Method B): 97.7%, $t_R$=11.2 min.

N-Hydroxy-4-(((6S)-4-methyl-8-(2-morpholinoethoxy)-3,5-dioxo-3,4,5,6-tetrahydro-2,6-methano[1,3]diazocino[5,6-b]indole-11(1H)-yl)methyl)benzamide ((S)-21)

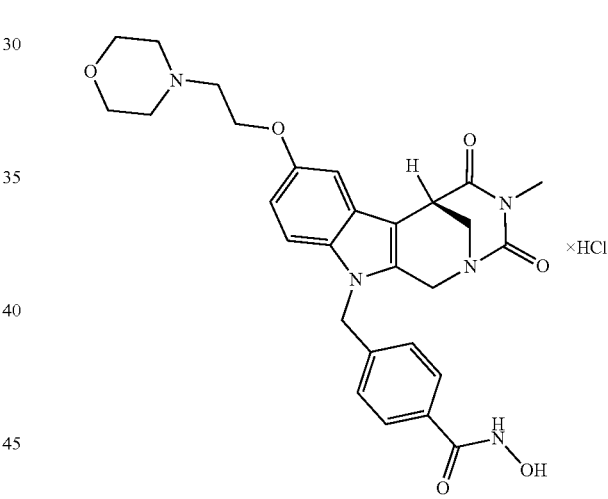

4-((4-Methyl-8-(2-morpholinoethoxy)-3,5-dioxo-3,4,5,6-tetrahydro-2,6-methano[1,3]diazocino[5,6-b]indol-11(1H)-yl)-N—((tetrahydro-2H-pyran-2-yl)oxy)benzamid ((S)-20) (0.060 g, 0.10 mmol) was dissolved in CH$_2$Cl$_2$ (2.09 mL), 6N HCl$_{iprop}$ (0.08 mL) (pH=1) was added and stirred for 2 h at r.t. (dc-control: CH$_2$Cl$_2$/MeOH (10:1)). The solvent was removed i.vac., the remaining solid washed with CH$_2$Cl$_2$ and dissolved again in MeOH (1.0 mL). The desired product was obtained by crystallization from PE/EE (1:1; 30 mL). Yield (0.048 g, 0.08 mmol, 80%). mp.: 175.7° C. IR (KBr): 3416, 1671, 1614 cm$^{-1}$. 1H NMR (400 MHz, DMSO-d$_6$) δ 11.18 (s, 1H, NHOH), 9.01 (s, 1H, NHOH), 7.65 (d, J=8.3 Hz, 2H, Ar—H), 7.33 (d, J=8.9 Hz, 1H, Ar—H), 7.09 (d, J=8.3 Hz, 2H, Ar—H), 7.05 (d, J=2.4 Hz, 1H, Ar—H), 6.82 (dd, J=8.9, 2.4 Hz, 1H, Ar—H), 5.36 (s, 2H, NCH$_2$Ar), 4.82 (d, J=16.6 Hz, 1H, NCH$_A$H$_B$C), 4.55 (d, J=16.5 Hz, 1H, NCH$_A$H$_B$C), 4.45-4.33 (m, 2H, OCH$_2$CH$_2$), 3.95-3.80 (m, 6H, OCH$_2$CH$_2$N-morpholine, NCH$_A$H$_B$CH, OCH$_2$CH$_2$N-morpholine, NCH$_2$CH), 3.55-3.42 (m, 5H, OCH$_2$C$\underline{H}_2$N, OCH$_2$C$\underline{H}_2$N-morpholine, NC$\underline{H}_A$H$_B$CH), 3.20 (s, 2H, OCH$_2$C$\underline{H}_2$N- morpholine), 2.89 (s, 3H, NC$\underline{H}_3$). $^{13}$C NMR (101 MHz, DMSO) δ 173.58 (quart.$\underline{C}$O), 164.26 (quart.$\underline{C}$O), 161.31 (quart.$\underline{C}$O), 152.68 (quart.$\underline{C}$—Ar—$\underline{C}$), 141.20 (quart. Ar—$\underline{C}$), 135.49 (quart. Ar—$\underline{C}$), 132.37 (quart. Ar—$\underline{C}$), 131.99 (quart. Ar—$\underline{C}$), 127.72 (-, Ar—$\underline{C}$H)$_2$), 127.02 (-, (Ar—$\underline{C}$H)$_2$), 126.61 (quart. Ar—$\underline{C}$), 112.22 (-, Ar—$\underline{C}$H), 111.75 (-, Ar—$\underline{C}$H), 105.50 (quart. Ar—$\underline{C}$), 102.20 (-, Ar—$\underline{C}$H), 63.63 (+, O($\underline{C}$H$_2$)$_2$CH$_2$N-morpholine), 63.38 (+, O$\underline{C}$H$_2$CH$_2$), 55.58 (+, O$\underline{C}$H$_2$$\underline{C}$H$_2$), 52.14 (+, O(CH$_2$)$_2$($\underline{C}$H$_2$)$_2$N-morpholine), 49.44 (+, N$\underline{C}$H$_2$C), 46.69 (+, N$\underline{C}$H$_2$CH), 46.56 (+, N$\underline{C}$H$_2$Ar), 36.49 (-, N$\underline{C}$H$_2$CH), 27.88 (-, N$\underline{C}$H$_3$). [α]$^{20}_{589}$ 14.3 (c 0.1; H$_2$O). HRMS (C$_{28}$H$_{31}$N$_5$O$_6$, ESI-MS) m/z: calcd.: 534.2347 [MH$^+$], found: 534.2350 [MH$^+$]. RP-HPLC (220 nm, Method B): 96.0%, $t_R$=8.5 min.

Synthesis of the R-Enantiomer

Ethyl (R)-2-(5-(benzyloxy)-1H-indol-3-yl)-3-nitropropanoate ((R)-7a)

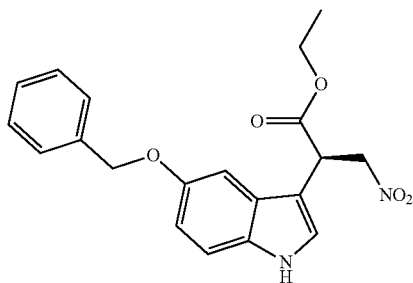 [SMILES: CCOC(=O)[C@@H](C[N+](=O)[O-])c1c[nH]c2ccc(OCc3ccccc3)cc12]

Preparation as described for the S-enantiomer (S)-7a by use of 5-(benzyloxy)-1H-indole (2.90 g, 12.99 mmol). Purification by cc (SiO$_2$; CH$_2$Cl$_2$, n-hexane, EtOAc 1:5:1). Yield 3.30 g (8.96 mmol, 69%) brown oil. IR (ATR): 1726; 1552 cm$^{-1}$. $^1$H NMR (300 MHz, CDCl$_3$) δ 8.14 (s, 1H), 7.52-7.47 (m, 2H), 7.44-7.27 (m, 4H), 7.17 (d, J=2.3 Hz, 1H), 7.11 (d, J=2.6 Hz, 1H), 6.98 (dd, J=8.8, 2.4 Hz, 1H), 5.21-5.15 (m, 1H), 5.12 (s, 2H), 4.67 (dd, J=9.7, 4.9 Hz, 1H), 4.59 (dd, J=14.1, 4.9 Hz, 1H), 4.31-4.06 (m, 2H), 1.23 (t, J=9.8, 4.5 Hz, 3H). ee determination by HPLC with a Chiralcel OD-H column, hexane/2-propanol (90:10), flow rate=0.6 mL/min, 220 nm. $t_R$=145.6 min (major), 139.2 min (minor), ≥99% ee, [α]$^{20}_{589}$ −89.5 (c 0.1; MeOH). HRMS (ESI-MS) m/z: calcd: 369.1445 [MH$^+$], found: 369.1445 [MH$^+$]. RP-HPLC (220 nm, Method A): 100.0%, $t_R$=21.7 min.

Ethyl (R)-3-amino-2-(5-(benzyloxy)-1H-indol-3-yl)propanoate hydrochloride ((R)-8a)

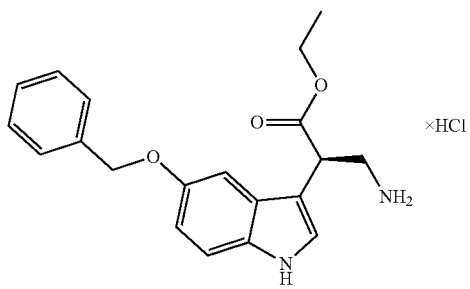 [SMILES: CCOC(=O)[C@@H](CN)c1c[nH]c2ccc(OCc3ccccc3)cc12]

Preparation as described for the S-enantiomer (S)-8a by use of (R)-ethyl 2-(1H-indol-3-yl)-3-nitropropanoate ((R)-7a) (4.71 g, 12.79 mmol). Yield (3.66 g, 9.76 mmol; 76%) colorless crystals. mp.: 46.7° C. IR (KBr): 3414, 2906, 1720, 1484 cm$^{-1}$. $^1$H NMR (300 MHz, DMSO-d$_6$) δ 11.10 (d, J=2.2 Hz, 1H), 8.12 (s, 2H), 7.52-7.29 (m, J=12.7, 9.7, 7.8, 2.5 Hz, 6H), 7.26 (d, J=2.5 Hz, 1H), 7.22 (d, J=2.3 Hz, 1H), 6.86 (dd, J=8.8, 2.4 Hz, 1H), 5.10 (s, 2H), 4.29-4.21 (m, 1H), 4.09 (q, J=10.8, 7.1 Hz, 2H), 3.60 (dd, J=8.7, 4.6 Hz, 1H), 3.19-3.07 (m, 1H), 1.13 (t, J=7.1 Hz, 3H). [α]$^2_{589}$ 77.5 (c 0.1; MeOH). HRMS (C$_{20}$H$_{22}$N$_2$O$_3$. ESI-MS) m/z: calcd.: 361.1523 [MNa$^+$], found: 361.1519 [MNa$^+$]. RP-HPLC (220 nm, Method A): 100.0%, $t_R$=21.7 min.

Ethyl (R)-6-(benzyloxy)-2,3,4,9-tetrahydro-1H-pyrido[3,4-b]indole-4-carboxylate hydrochloride ((R)-9a)

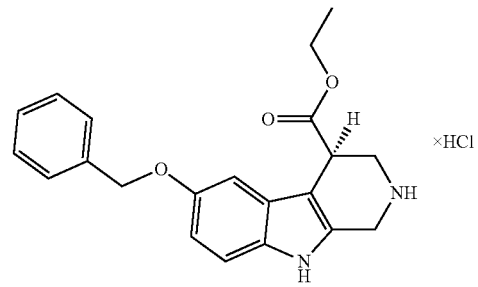 [SMILES: CCOC(=O)[C@H]1CNCc2[nH]c3ccc(OCc4ccccc4)cc3c21]

Preparation as described for the S-enantiomer (S)-9a by use of ethyl (R)-3-amino-2-(5-(benzyloxy)-1H-indol-3-yl)propanoate hydrochloride ((R)-8a) (3.06 g, 8.16 mmol). Yield (2.20 g, 5.69 mmol, 70%) colorless crystals. mp.: 266.4-267.0° C. IR (KBr): 2921; 2793; 1719 cm$^{-1}$. $^1$H NMR (400 MHz, DMSO-d$_6$) δ 11.20 (s, 1H), 10.20 (s, 1H), 9.12 (s, J=430.8 Hz, 1H), 7.47-7.26 (m, 6H), 7.12 (d, J=2.4 Hz, 1H), 6.85 (dd, J=8.8, 2.4 Hz, 1H), 5.07 (q, J=12.1 Hz, 2H), 4.38-4.21 (m, 2H), 4.19-4.15 (m, 1H), 4.15-4.03 (m, 2H), 3.58 (m, 2H), 1.20 (t, J=7.1 Hz, 3H). ee determination by HPLC with a Chiralcel OD-H column, hexane/2-propanol (90:10), flow rate=0.6 mL/min, 220 nm. $t_R$=107.9 min (major), 87.4 min (minor), ≥99% ee, [α]$^{20}_{589}$ 128.8 (c 0.1; MeOH). HRMS (C$_{21}$H$_{22}$N$_2$O$_3$, ESI-MS) m/z: calcd: 351.1703[MH$^+$], found: 351.1704 [MH$^+$]. RP-HPLC (220 nm, Method A): 99.7%, $t_R$=8.0 min.

(R)-6-(Benzyloxy)-N-methyl-2,3,4,9-tetrahydro-1H-pyrido[3,4-b]indole-4-carboxamide hydrochloride ((R)-67a)

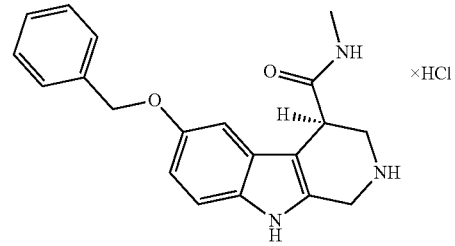 [SMILES: CNC(=O)[C@H]1CNCc2[nH]c3ccc(OCc4ccccc4)cc3c21]

Preparation as described for the S-enantiomer (S)-67a by use of ethyl (R)-6-(benzyloxy)-2,3,4,9-tetrahydro-1H-pyrido[3,4-b]indol-4-carboxylat hydrochlorid ((R)-9a) (0.40 g, 1.03 mmol. Yield (0.135 g, 0.36 mmol; 35%) colorless crystals. mp.: 156.7° C. IR (KBr): 2933; 1643 cm$^{-1}$. $^1$H NMR (400 MHz, DMSO-d$_6$) δ 10.65 (s, 1H), 7.92 (m, 1H), 7.46-7.27 (m, 5H), 7.16 (d, J=8.7 Hz, 1H), 7.00 (d, J=2.3 Hz, 1H), 6.73 (dd, J=8.7, 2.4 Hz, 1H), 5.03 (d, J=4.2 Hz, 2H), 3.91-3.78 (m, 2H), 3.49-3.42 (m, 1H), 3.13 (dd, J=12.9, 4.1 Hz, 1H), 2.96 (dd, J=12.9, 4.8 Hz, 1H), 2.57 (d, J=4.6 Hz, 3H). [ ]$^{20}_{589}$ 36.9 (c 0.1; MeOH). HRMS (C$_{20}$H$_{21}$N$_3$O$_2$, ESI-MS) m/z: calcd.: 336.1707 [MH$^+$], found: 336.1706 [MH$^+$]. RP-HPLC (220 nm, Method A): 99.2%, t$_R$=6.2 min.

(6R)-8-(Benzyloxy)-4-methyl-6,11-dihydro-2,6-methano[1,3]diazocino[5,6-b]indole-3,5(1H,4H)-dione ((R)-12)

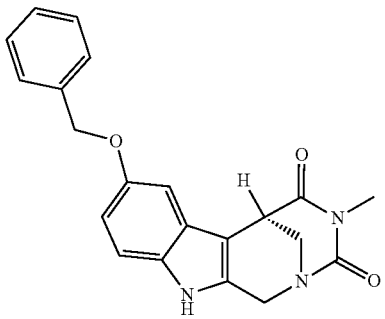 [SMILES: CN1C(=O)[C@H]2CN(Cc3[nH]c4ccc(OCc5ccccc5)cc4c32)C1=O]

Preparation as described for the S-enantiomer (S)-12 by use of (R)-6-(Benzyloxy)-N-methyl-2,3,4,9-tetrahydro-1H-pyrido[3,4-b]indole-4-carboxamide hydrochloride ((R)-67a) (0.136 g, 0.37 mmol). Yield (0.094 g; 0.26 mmol, 70%) beige crystals. mp.: 236.1-236.4° C. IR (KBr): 2926, 1729, 1672 cm$^{-1}$. $^1$H NMR (400 MHz, CDCl$_3$) δ 8.03 (s, 1H, NH (Indol)), 7.51-7.47 (m, 2H, Ar—H), 7.42-7.29 (m, 3H, Ar—H), 7.23-7.19 (m, 2H, Ar—H), 6.92 (dd, J=8.8, 2.4 Hz, 1H, Ar—H), 5.14-5.05 (m, 2H, NCH$_2$Ar (Benzyl)), 4.87 (d, J=16.3 Hz, 1H, NCH$_A$H$_B$C), 4.50 (d, J=16.3 Hz, 1H, NCH$_A$H$_B$C), 3.90 (d, J=13.1 Hz, 1H, NCH$_A$H$_B$CH), 3.83 (s, 1H, NCH$_A$H$_B$CH), 3.37 (dd, J=13.1, 2.2 Hz, 1H, NCH$_A$H$_B$CH), 3.07 (s, 3H, NCH$_3$).

$^{13}$C NMR (101 MHz, CDCl$_3$) δ 173.25 (quart.CO), 160.96 (quart.CO), 154.05 (quart. Ar—C), 137.42 (quart. Ar—C), 132.49 (quart. Ar—C), 130.92 (quart. Ar—C), 128.55 (+, (Ar—CH)$_2$), 127.87 (+, (Ar—CH)$_2$), 127.71 (+, Ar—CH), 126.62 (quart. Ar—C), 113.65 (+, Ar—CH), 112.06 (+, Ar—CH), 106.49 (quart. Ar—C), 101.46 (+, Ar—CH), 70.85 (-, NCH$_2$Ar (Benzyl)), 50.25 (-, NCH$_2$C), 47.60 (-, NCH$_2$CH), 36.84 (+, NCH$_2$CH), 27.91 (+, NCH$_3$). [α]$^{20}_{589}$ 30.4 (c 0.1; MeOH). HRMS (C$_{21}$H$_{19}$N$_3$O$_3$, ESI-MS) m/z: calcd: 362.1499 [MH$^+$], found: 362.1500 [MH$^+$]. RP-HPLC (220 nm, Method A): 99.5%, t$_R$=18.2 min.

tert-Butyl 4-(((6R)-8-(benzyloxy)-4-methyl-3,5-dioxo-3,4,5,6-tetrahydro-2,6-methano[1,3]diazocino [5,6-b]indole-11(1H)-yl)methyl)benzoate ((R)-14)

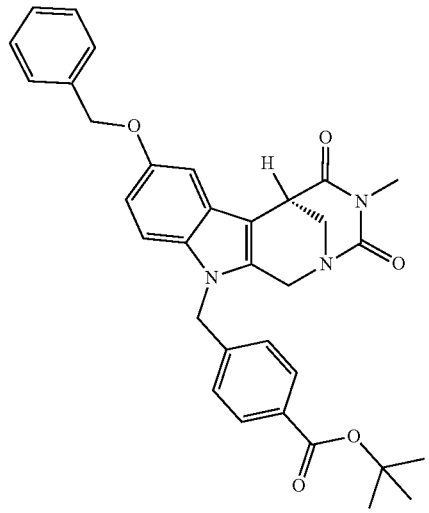 [SMILES: CN1C(=O)[C@H]2CN(Cc3c2c2cc(OCc4ccccc4)ccc2n3Cc2ccc(C(=O)OC(C)(C)C)cc2)C1=O]

Preparation as described for the S-enantiomer (S)-14 by use of (6R)-8-(benzyloxy)-4-methyl-6,11-dihydro-2,6-methano[1,3]diazocino[5,6-b]indole-3,5(1H,4H)-dione ((R)-12) (0.071 g, 0.20 mmol). Yield (0.128 g, 0.23 mmol, 87%) yellow oil. IR (KBr): 1710; 1684 cm$^{-1}$. $^1$H NMR (400 MHz, DMSO-d$_6$) δ 7.88 (d, J=8.3 Hz, 1H), 7.80 (d, J=8.3 Hz, 2H), 7.46 (d, J=7.6 Hz, 3H), 7.37 (d, J=7.6 Hz, 1H), 7.30-7.28 (m, 1H), 7.13 (d, J=8.3 Hz, 2H), 7.09 (d, J=2.4 Hz, 1H), 6.82 (dd, J=8.9, 2.4 Hz, 1H), 5.39 (s, 2H), 5.11-5.03 (m, 2H), 4.79 (d, J=16.6 Hz, 1H), 4.50 (d, J=16.5 Hz, 1H), 3.87 (d, J=12.8 Hz, 1H), 3.81 (br s, 1H), 3.42 (dd, J=13.1, 2.0 Hz, 1H), 2.89 (s, 3H), 1.50 (s, 9H). [α]$^{20}_{589}$ 25.0 (c 0.1; MeOH). HRMS (C$_{33}$H$_{33}$N$_3$O$_5$, ESI-MS) m/z: calcd: 552.2493 [MH$^+$], found: 5522491 [MH$^+$]. RP-HPLC (220 nm, Method A): 98.7%, t$_R$=7.0 min.

tert-Butyl 4-(((6R)-8-hydroxy-4-methyl-3,5-dioxo-3,4,5,6-tetrahydro-2,6-methano[1,3]diazocino[5,6-b] indole-11(1B)-yl)methyl)benzoate ((R)-15)

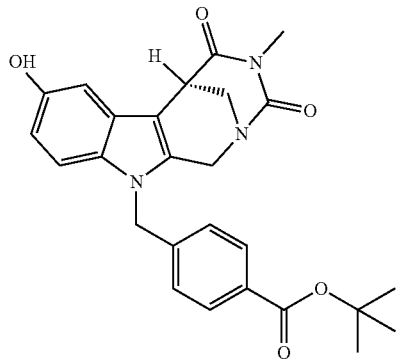 [SMILES: CN1C(=O)[C@H]2CN(Cc3c2c2cc(O)ccc2n3Cc2ccc(C(=O)OC(C)(C)C)cc2)C1=O]

Preparation as described above for the S-Enantiomer (S)-15 by use of tert-Butyl 4-(((6R)-8-(benzyloxy)-4-methyl-3,5-dioxo-3,4,5,6-tetrahydro-2,6-methano[1,3]diazocino[5,6-b]indole-1(1H)-yl)methyl)benzoate ((R)-14) (0.138 g, 0.25 mmol). Yield (0.068 g, 0.15 mmol, 60%) colorless crystals. mp.: 105.9° C. IR (KBr): 2927, 1713, 1665 cm$^{-1}$. $^1$H NMR (400 MHz, DMSO-d$_6$) δ 8.86 (s, 1H), 7.80 (d, J=8.3 Hz, 2H), 7.21-7.10 (m, 3H), 6.85 (d, J=2.2 Hz, 1H), 6.57 (dd, J=8.8, 2.3 Hz, 1H), 5.35 (d, J=14.8 Hz, 2H), 4.76 (d, J=16.5 Hz, 1H), 4.48 (d, J=16.4 Hz, 1H), 3.85 (d, J=12.7 Hz, 1H), 3.75 (d, J=11.6 Hz, 1H), 3.46-3.34 (m, 1H), 2.88 (s, 3H), 1.50 (s, 9H). [α]$^{20}_{589}$ −96.8 (c 0.1; MeOH). MS(C$_{26}$H$_{27}$N$_3$O$_5$, LC-MS, ESI) m/z (%): 462 [MH$^+$] (26), 406 [MH$^+$—C$_4$H$_8$] (100), 479 [MNH$_4{^+}$](83). Anal. (C$_{26}$H$_{27}$N$_3$O$_5$) calcd.: C, 67.66; H, 5.90; N, 9.10; found: C, 67.26; H, 6.04; N, 8,74.

tert-Butyl 4-(((6R)-4-methyl-8-(2-morpholinoethoxy)-3,5-dioxo-3,4,5,6-tetrahydro-2,6-methano[1,3]diazocino[5,6-b]indole-11(1H)-yl)methyl)benzoate ((R)-17)

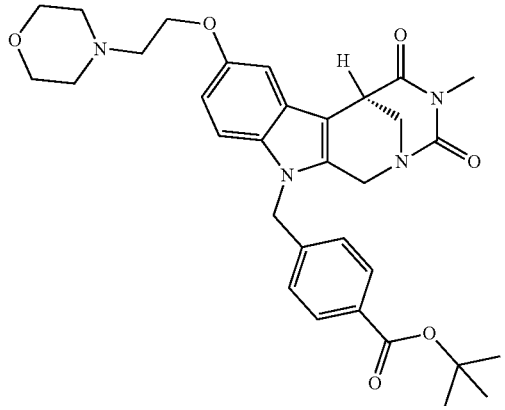 [SMILES: CN1C(=O)[C@H]2CN(Cc3c2c2cc(OCCN4CCOCC4)ccc2n3Cc2ccc(C(=O)OC(C)(C)C)cc2)C1=O]

Preparation as described for the S-enantiomer (S)-17 by use of tert Butyl 4-(((6R)-8-hydroxy-4-methyl-3,5-dioxo-3,4,5,6-tetrahydro-2,6 methano[1,3]diazocino[5,6-b]indole-11(1H)-yl)methyl)benzoate ((R)-15) (0.157 g, 0.34 mmol). The product was purified by cc (SiO$_2$; CH$_2$Cl$_2$, EtOAc 3:1) and (SiO$_2$; CH$_2$Cl$_2$, MeOH 10:1) (dry-load-technique). Yield 0.161 g (0.28 mmol, 82%) yellow oil. IR (KBr): 2927; 1712; 1688 cm$^{-1}$. $^1$H NMR (400 MHz, CDCl$_3$) δ 7.91 (d, J=8.3 Hz, 2H, Ar—H̲), 7.15 (d, J=2.4 Hz, 1H, Ar—H̲), 7.09 (d, J=8.9 Hz, 1H, Ar—H̲), 7.03 (d, J=8.3 Hz, 2H, Ar—H̲), 6.83 (dd, J=8.9, 2.4 Hz, 1H, Ar—H̲), 5.33-5.24 (m, 1H, NC H̲$_A$H$_B$Ar), 5.09 (d, J=17.0 Hz, 1H, NCH$_A$H̲$_B$Ar), 4.84 (d, J=16.4 Hz, 1H, NCH$_A$H̲$_B$C), 4.32-4.17 (m, 3H, NCH$_A$H̲$_B$C, OCH$_2$CH$_2$), 3.89 (d, J=13.1 Hz, 1H, NCH$_A$H̲$_B$CH), 3.85 (br s, 1H, NCH$_2$CH̲), 3.85-3.77 (m, 4H, O(C H̲$_2$)$_2$CH$_2$N-morpholine), 3.32 (dd, J=13.1, 2.2 Hz, 1H, NCH$_A$H̲$_B$CH), 3.06 (s, 3H, NCH̲$_3$), 2.95 (s, 2H, OCH$_2$CH̲$_2$), 2.75 (br s, 4H, O(CH$_2$)$_2$(CH̲$_2$)$_2$N-morpholine), 1.56 (s, 9H, OC(CH$_3$)$_3$).

$^{13}$C NMR (101 MHz, CDCl$_3$) δ 173.12 (quart.C̲O), 165.16 (quart.C̲O), 161.25 (quart.C̲O), 153.65 (quart.O—Ar—C̲), 141.01 (quart. Ar—C̲), 133.83 (quart. Ar—C̲), 131.93 (quart. Ar—C̲), 131.79 (quart. Ar—C̲), 130.20 (+, (Ar—C̲H)$_2$), 126.49 (quart. Ar—C̲), 126.07 (+, (Ar—C̲H)$_2$), 113.15 (+, Ar—C̲H), 110.46 (+, Ar—C̲H), 105.98 (quart. Ar—C̲), 101.53 (+, Ar—C̲H), 81.27 (quart.OC̲(CH$_3$)$_3$), 66.42 (−, O(C̲H$_2$)$_2$CH$_2$N-morpholine), 65.87 (−, O C̲H$_2$CH$_2$), 57.61 (−, OCH$_2$C̲H$_2$), 53.83 (−, O(CH$_2$)$_2$ (C̲H$_2$)$_2$N-morpholine), 49.46 (−, NC̲H$_2$C), 47.36 (−, N C̲H$_2$CH), 47.13 (−, NC̲H$_2$Ar), 36.86 (+, NCH$_2$C̲H), 28.16 (+, OC(C̲H$_3$)$_3$), 27.91 (+, NC̲H$_3$). [α]$^{20}_{589}$ −46.8 (c 0.1;

MeOH). HRMS (C$_{32}$H$_{38}$N$_4$O$_6$, ESI-MS) m/z: calcd.: 575.2864 [MH$^+$], found: 575.2866 [MH$^+$]. RP-HPLC (220 nm, Method A): 98.5%, t$_R$=11.4 min.

4-(2-(((6R)-11-(4-Carboxybenzyl)-4-methyl-3,5-dioxo-1,3,4,5,6,11-hexahydro-2,6-methano[1,3]diazocino[5,6-b]indole-8-yl)oxy)ethyl)morpholine-4-ium 2,2,2-trifluoroacetate ((R)-18)

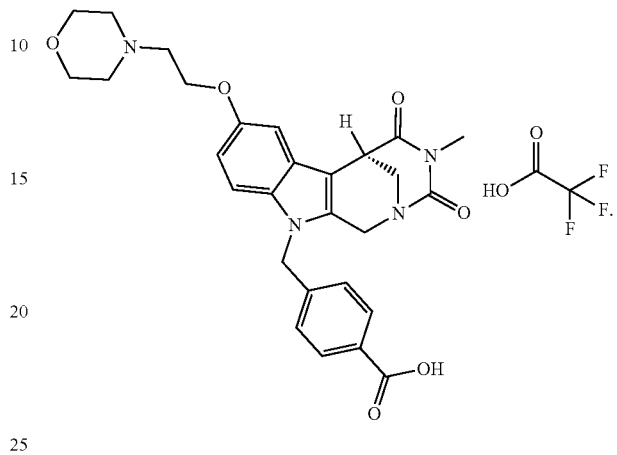

Preparation as described for the S-enantiomer (S)-18 by use of tert-butyl 4-(((6R)-4-methyl-8-(2-morpholinoethoxy)-3,5-dioxo-3,4,5,6-tetrahydro-2,6-methano[1,3]diazocino[5,6-b]indole-11(1H)-yl)methyl)benzoate ((R)-17) (0.033 g, 0.06 mmol). Yield (0.05 g, 0.08 mmol; 99%) brown oil. IR (ATR): 2925; 1723; 1684 cm$^{-1}$. $^1$H NMR (400 MHz, DMSO-d$_6$) δ 9.93 (s, 1H), 7.84 (d, J=8.3 Hz, 2H), 7.34 (d, J=8.9 Hz, 1H), 7.10 (m, 3H), 6.83 (dd, J=8.9, 2.4 Hz, 1H), 5.41 (s, 2H), 4.81 (d, J=16.6 Hz, 1H), 4.53 (d, J=16.6 Hz, 1H), 4.00-3.96 (m, 3H), 3.89 (d, J=12.6 Hz, 3H), 3.82 (s, 2H), 3.74-3.65 (m, 3H), 3.58 (m, 2H), 3.50 (m, 1H), 3.44 (d, J=11.1 Hz, 1H), 2.88 (s, 3H). $^{19}$F NMR (377 MHz, DMSO-d$_6$) δ −73.70 (s). [α]$^{20}_{589}$ −11.7 (c 0.1; MeOH). HRMS (C$_{28}$H$_{30}$N$_4$O$_6$. ESI-MS) m/z: calcd: 519.2238 [MH$^+$], found: 519.2244 [MH$^+$]. RP-HPLC (220 nm, Method B): 100.0%, t$_R$=10.5 min.

4-(((6R)-4-Methyl-8-(2-morpholinoethoxy)-3,5-dioxo-3,4,5,6-tetrahydro-2,6-methano[1,3]diazocino [5,6-b]indole-11(1B)-yl)methyl)-N—((tetrahydro-2H-pyran-2-yl)oxy)benzamide ((R)-20)

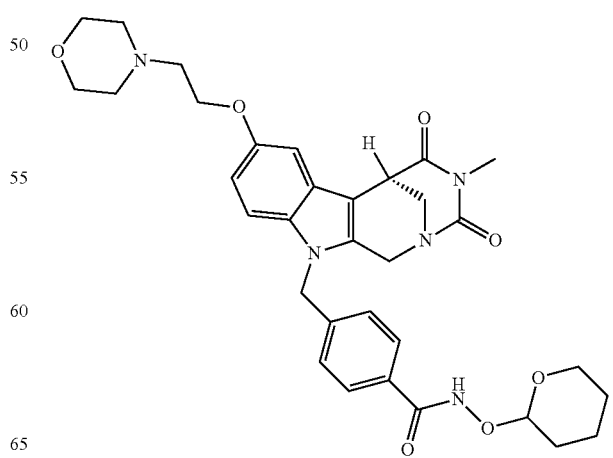

Preparation as described for the S-enantiomer (S)-20 by use of 4-(2-(((6R)-11-(4-carboxybenzyl)-4-methyl-3,5-dioxo-1,3,4,5,6,11-hexahydro-2,6-methano[1,3]diazocino[5,6-b]indole-8-yl)oxy)ethyl)morpholine-4-ium 2,2,2-trifluoroacetate ((R)-18) (0.063 g, 0.10 mmol). Yield (0.042 g, 0.07 mmol, 70%) yellow oil. IR(ATR): 1727; 1683 cm$^{-1}$. $^1$H NMR (400 MHz, DMSO-d$_6$) δ 11.56 (s, 1H), 8.15 (s, 1H), 7.65 (d, J=8.2 Hz, 2H), 7.28 (d, J=8.9 Hz, 1H), 7.10 (d, J=8.3 Hz, 2H), 7.01 (m, 1H), 6.76 (d, J=8.7 Hz, 1H), 5.37 (d, J=17.7 Hz, 2H), 4.93 (m, 1H), 4.80 (d, J=16.7 Hz, 1H), 4.51 (d, J=16.6 Hz, 1H), 4.13 (m, 2H), 4.00 (m, 1H), 3.87 (d, J=12.7 Hz, 1H), 3.81 (m, 1H), 3.63-3.56 (m, 4H), 3.49 (m, 1H), 3.42 (d, J=13.4 Hz, 1H), 3.16-3.08 (m, 4H), 2.87 (s, 3H), 2.77-2.66 (m, 2H), 1.67-1.51 (m, 6H). ee determination by HPLC with a Phenomenex Lux Cellulose-2 column, methanol/2-propanol (90:10), flow rate=1.0 mL/min, 220 nm. t$_R$=33.8-37.0 min (major), 18.7-23.4 min (minor), 94% ee, [α]$^{20}_{589}$ −32.0 (c 0.1; MeOH). HRMS (C$_{33}$H$_{39}$N$_5$O$_7$, ESI-MS) m/z: calcd: 618.2922 [MH$^+$], found: 618.2928 [MH$^+$]. RP-HPLC (220 nm, Method B): 97.8%, t$_R$=11.4 min.

N-Hydroxy-4-(((6R)-4-methyl-8-(2-morpholinoethoxy)-3,5-dioxo-3,4,5,6-tetrahydro-2,6-methano[1,3]diazocino[5,6-b]indole-11(1B)-yl)methyl)benzamide ((R)-21)

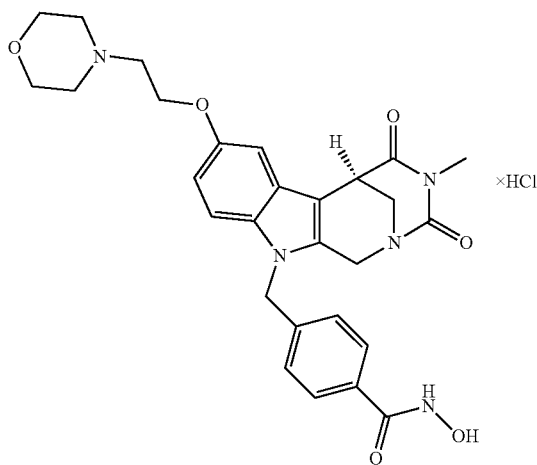 [SMILES: CN1C(=O)[C@H]2CN(Cc3c2c2cc(OCCN4CCOCC4)ccc2n3Cc2ccc(C(=O)NO)cc2)C1=O]

Preparation as described for the S-enantiomer (S)-21 by use of 4-(((6R)-4-Methyl-8-(2-morpholinoethoxy)-3,5-dioxo-3,4,5,6-tetrahydro-2,6-methano[1,3]diazocino[5,6-b]indol-11(1H)-yl)methyl)-N—((tetrahydro-2H-pyran-2-yl)oxy)benzamid ((R)-20) (0.044 g, 0.07 mmol). Yield (0.029 g, 0.05 mmol, 71%) colorless crystals. mp.: 280.8° C. IR (KBr): 3415; 1724; 1679 cm$^{-1}$. $^1$H NMR (400 MHz, DMSO-d$_6$) δ 11.18 (s, 1H, NHOH), 9.00 (s, 1H, NHOH), 7.65 (d, J=8.3 Hz, 2H, Ar-H), 7.33 (d, J=7.8 Hz, 1H, Ar—H), 7.09 (d, J=8.3 Hz, 2H, Ar—H), 7.05 (d, J=2.4 Hz, 1H, Ar—H), 6.82 (dd, J=8.9, 2.4 Hz, 1H, Ar—H), 5.36 (s, 2H, NCH$_2$Ar), 4.82 (d, J=16.6 Hz, 1H, NCH$_A$H$_B$C), 4.54 (dd, J=16.2, 8.7 Hz, 1H, NCH$_A$H$_B$C), 4.44-4.33 (m, 2H, OCH$_2$CH$_2$), 3.96-3.79 (m, 6H, OCH$_2$CH$_2$N-morpholine, NCH$_A$H$_B$CH, OCH$_2$CH$_2$N-morpholine, NCH$_2$CH), 3.55-3.42 (m, 5H, OCH$_2$CH$_2$N, OCH$_2$CH$_2$N-morpholine, NCH$_A$H$_B$CH), 3.20 (s, J=16.3 Hz, 2H, OCH$_2$CH$_2$N-morpholine), 2.89 (s, 3H, NCH$_3$). $^{13}$C NMR (101 MHz, DMSO) δ 173.58 (quart.CO), 164.16 (quart.CO), 161.31 (quart.CO), 152.68 (quart.O—Ar—C), 141.27 (quart. Ar—C), 135.62 (quart. Ar—C), 132.33 (quart. Ar—C) 131.99 (quart. Ar—C) 127.71 (-, Ar—CH)$_2$), 127.02 (-, Ar—CH)$_2$), 126.61 (quart. Ar—C), 112.22 (-, Ar—CH), 111.75 (-, Ar—CH), 105.50 (quart. Ar—C), 102.12 (-, Ar—CH), 63.63 (+, OCH$_2$)$_2$CH$_2$N-morpholine), 63.32 (+, OCH$_2$CH$_2$), 55.59 (+, OCH$_2$CH$_2$), 52.14 (+, O(CH$_2$)$_2$(CH$_2$)$_2$N-morpholine), 49.44 (+, NCH$_2$C), 46.67 (+, NCH$_2$CH), 46.57 (+, NCH$_2$Ar), 36.41 (-, NCH$_2$CH), 27.88 (-, NCH$_3$). [α]$^{20}_{589}$ −14.0 (c 0.1; H$_2$O). HRMS (C$_{28}$H$_{31}$N$_5$O$_6$, ESI-MS) m/z: calcd: 534.2347 [MH$^+$], found: 534.2354 [MH$^+$]. RP-HPLC (220 nm, Method B): 95.0%, t$_R$=8.5 min.

Example 2: Synthesis of Compounds 31a and 31b

Scheme 2a: Synthesis of compound 31a with 23, 24, 25, 26, 27, 28a, 29a, 30a as examples.

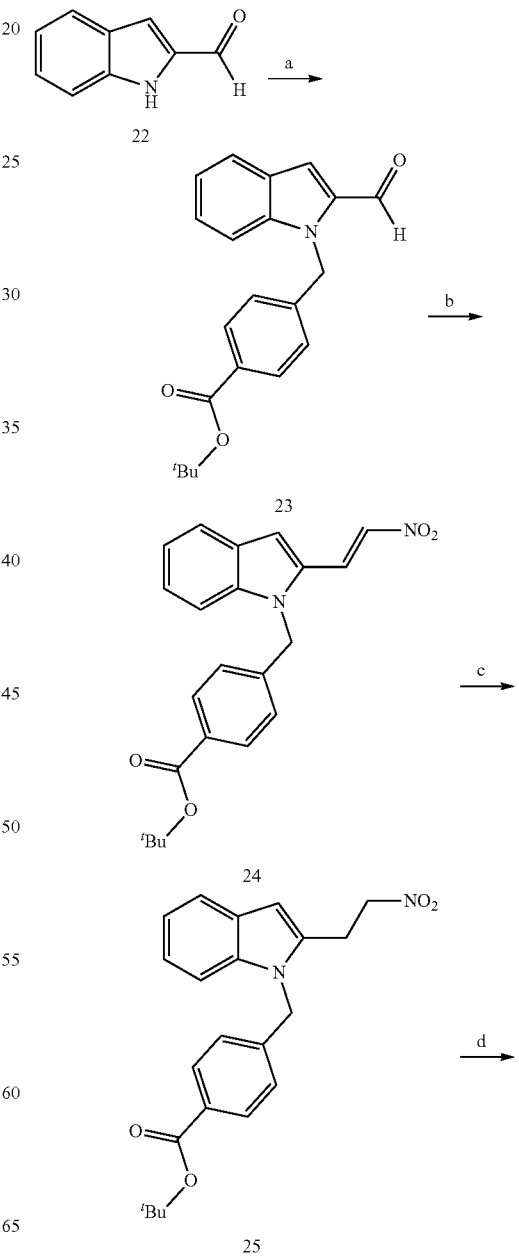

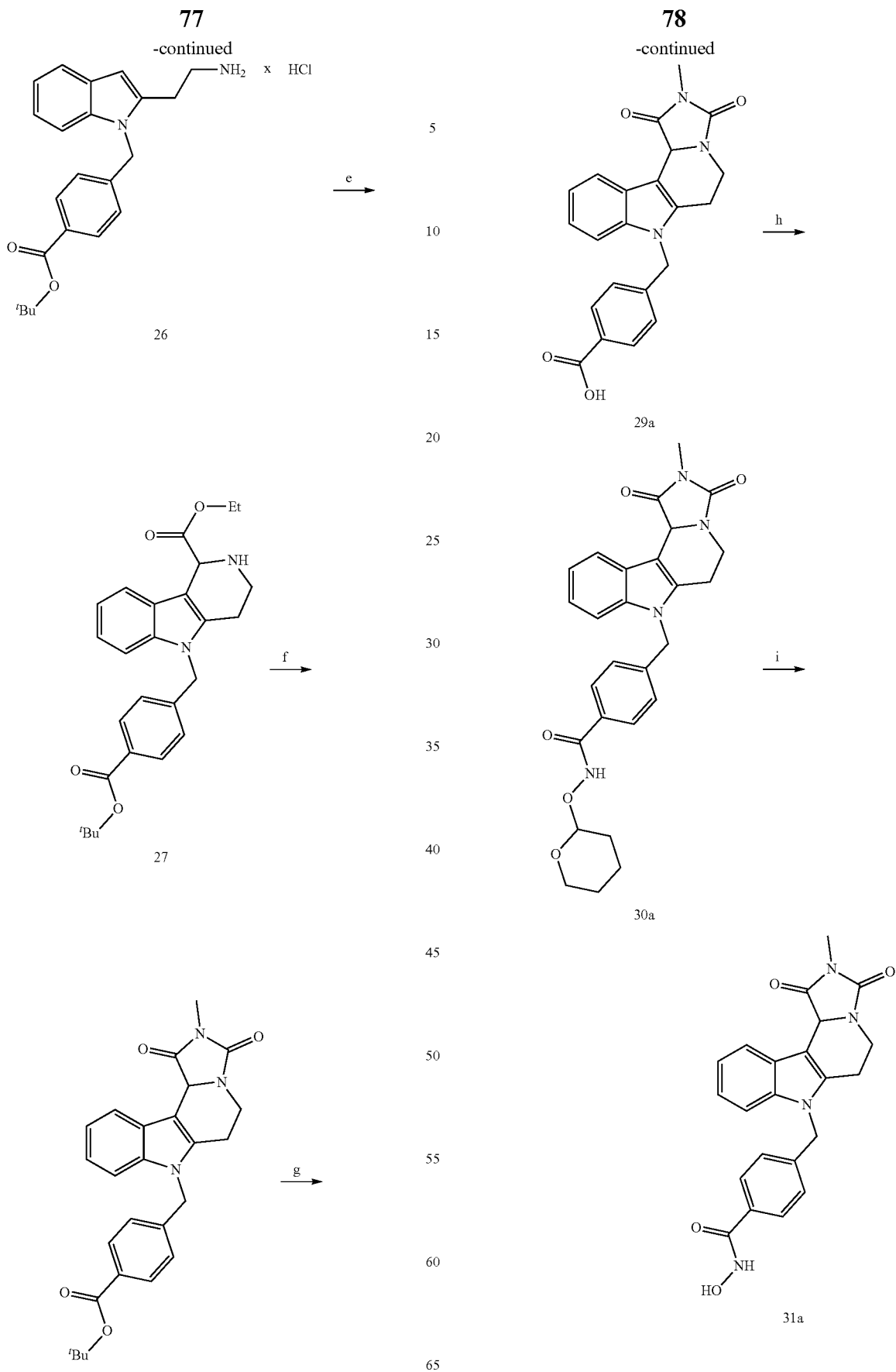
To obtain a compound 53a with core structure 31a, which possess an additional solubility enhancing substructure, this part can be introduced as shown in scheme 2b by use of 5-benzyloxy-indole-2-carbaldehyde 42 instead of 22.
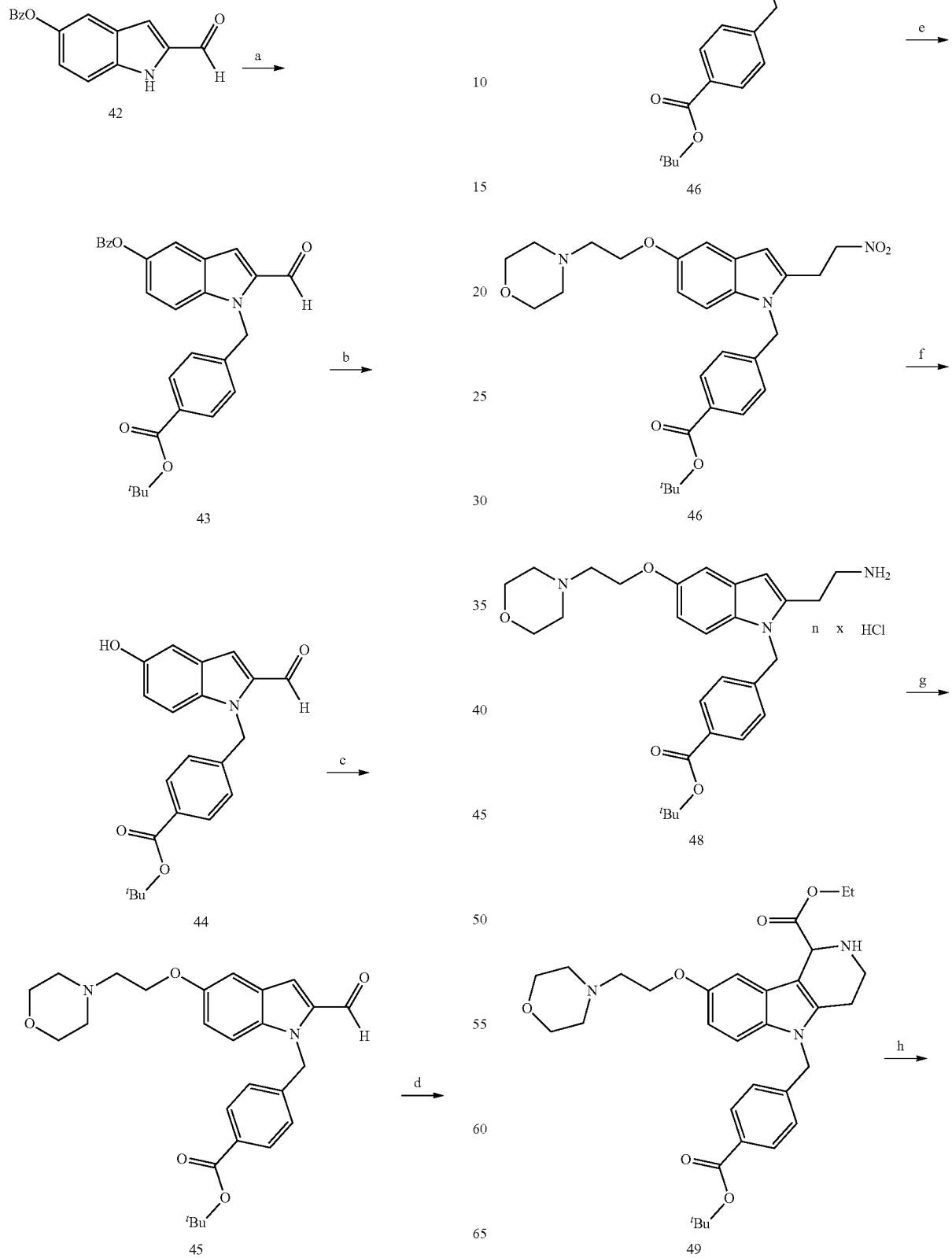
Scheme 2b: Synthesis of compound 53a as an example.

81
-continued
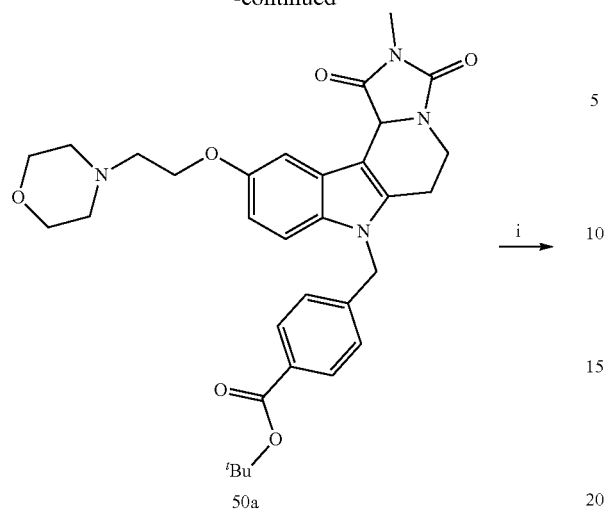
50a
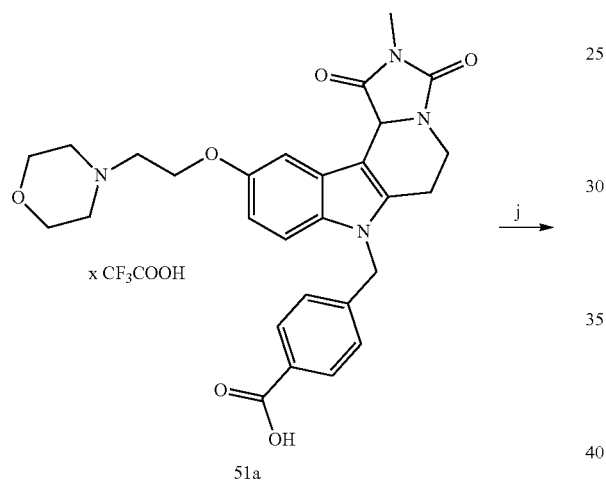
51a
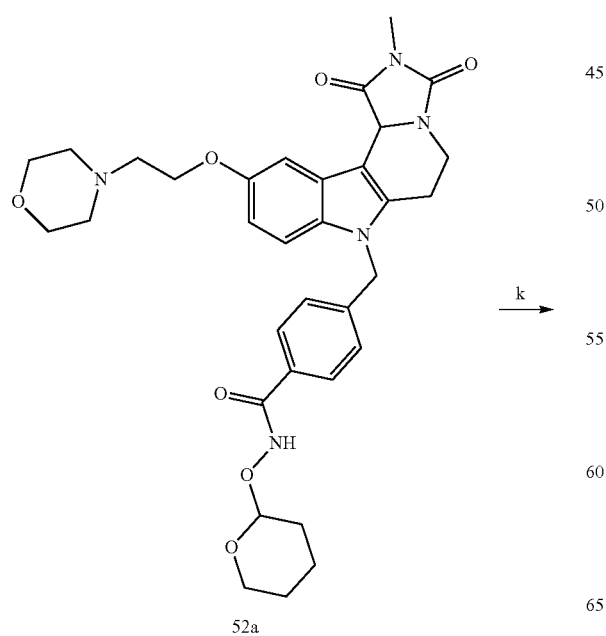
52a
82
-continued
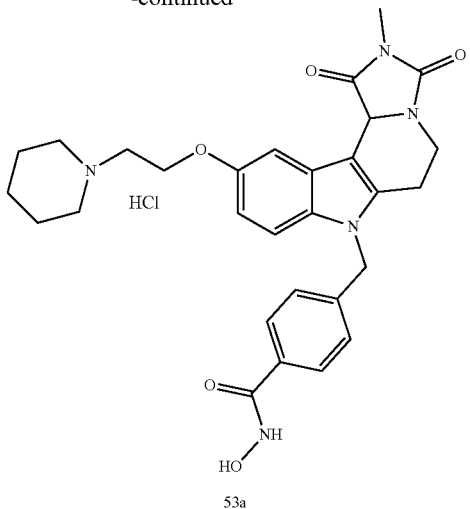
53a
Scheme 3a: Synthesis of compound 31b with 27, 28b, 29b, 30b as examples.
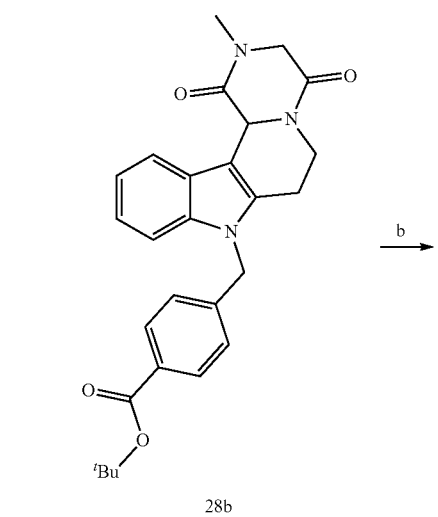

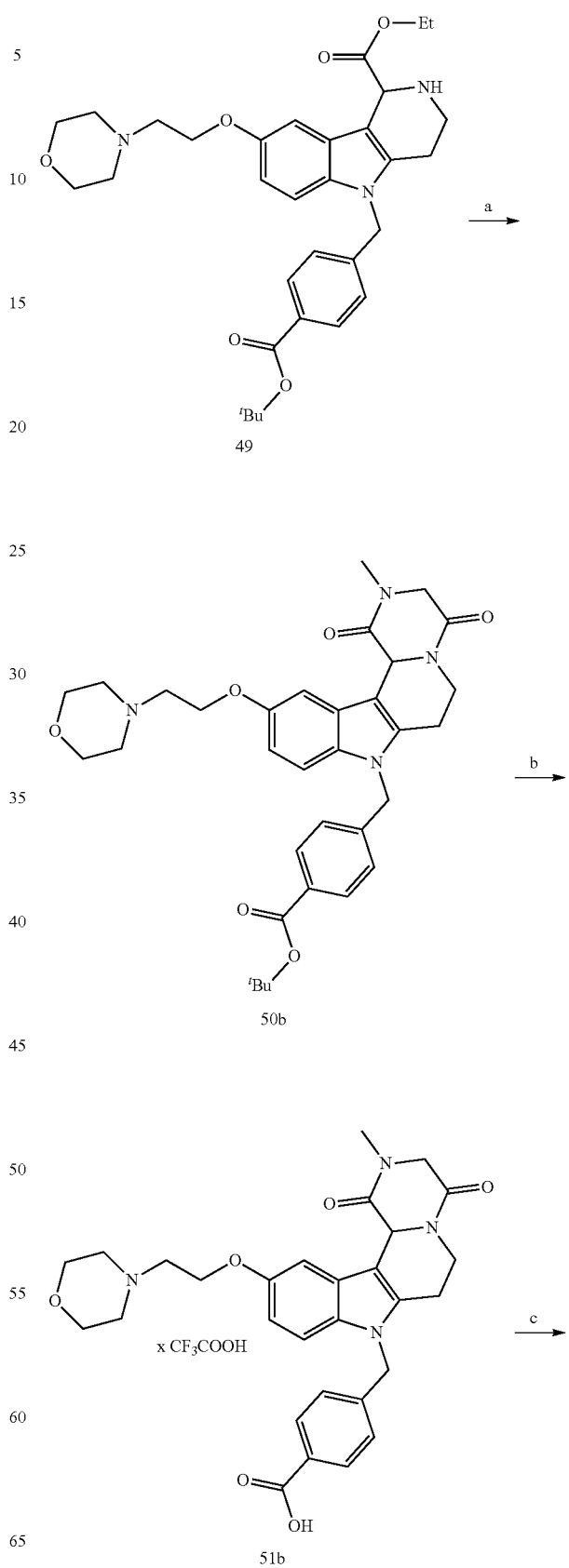
Scheme 3b: Synthesis of compound 53b as example.
To obtain a compound 53b with core structure 31b, which possess an additional solubility enhancing substructure, this part can be introduced as shown in scheme 3b by use of 27 instead of 22.

-continued

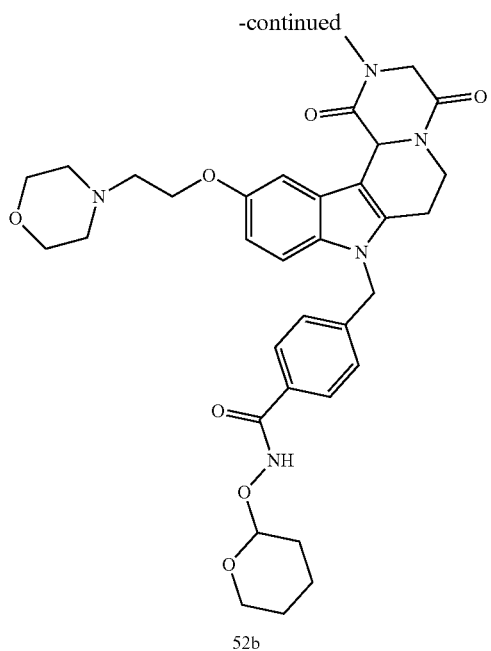

52b

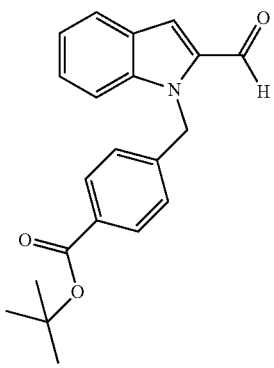 [SMILES: CC(C)(C)OC(=O)c1ccc(Cn2c(C=O)cc3ccccc32)cc1]

53b tert-Butyl 4-((2-formyl-1H-indol-1-yl)methyl)benzoate (23)

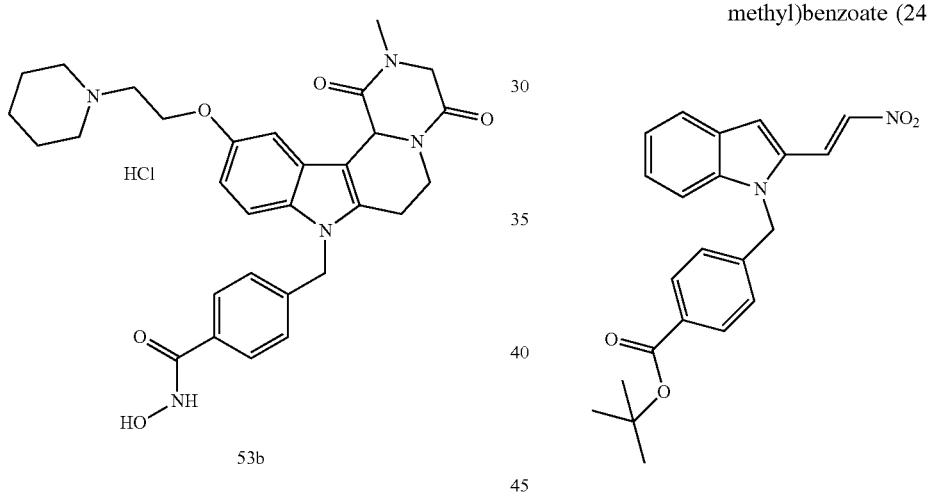

Under nitrogen a solution of the indole-2-carbaldehyde (18.5 g; 127.4 mmol) in DMF (300 mL) was cooled to 0° C. After addition of NaH (1.1 equ; 60% in paraffin) the mixture was stirred for 10 min. The alkylating agent, tert-butyl 4-(bromomethyl)benzoate (1.1 equ.) was added and stirring at rt continued until completion of the reaction (TLC). The mixture was poured into water. The crude product was isolated by extraction of the aqueous phase with Et$_2$O (4×250 mL). Silica gel chromatography (CH$_2$Cl$_2$/light petrol 1:1) afforded the desired product. Yield 27.16 g (80.98 mmol, 64%) yellow crystals after cc (CH$_2$Cl$_2$) from CH$_2$Cl$_2$/light petrol; mp.: 131.7-133.1° C., IR (KBr): 1709, 1671 cm$^{-1}$; $^1$H NMR (300 MHz, CDCl$_3$): δ 9.90 (s, 1H), 7.92-7.84 (m, 2H), 7.78 (d, J=8.1 Hz, 1H), 7.42-7.29 (m, 3H), 7.20 (ddd, J=8.0, 6.6, 1.3 Hz, 1H), 7.09 (d, J=8.4 Hz, 2H), 5.88 (s, 2H), 1.54 (s, 9H); HRMS (ESI-MS) m/z: calc.: 336.1594 [MH$^+$], found: 336.1603 [MH$^+$], Anal. calcd. for C$_{21}$H$_{21}$NO$_3$: C, 75.20; H, 6.31; N, 4.18; found C, 75.07; H, 6.33; N, 4.09.

(E)-tert-Butyl 4-((2-(2-nitrovinyl)-1H-indol-1-yl)methyl)benzoate (24)

(E)-tert-butyl 4-((2-(2-nitrovinyl)-1H-indol-1-yl)methyl)benzoate (24) was prepared according to a modified literature procedure (Yang, Li et al. 2016) as follows: A solution of tert-butyl 4-((2-formyl-1H-indol-1-yl)methyl)benzoate (23) (24.55 g; 73.20 mmol) and ammonium acetate (2.82 g, 36.6 mmol) in nitromethane (250 mL) was heated at reflux for 10 h under nitrogen. After removal of half of the solvent the mixture was cooled, the crystalline precipitating product removed by filtration and crystallized from ethanol. Yield 17.50 g (46.2 mmol, 63%) yellow crystals from ethanol; mp.: 196.3-199.5° C.; IR (KBr): 1704, 1632 cm$^{-1}$; $^1$H NMR (300 MHz, CDCl$_3$): δ 8.03 (d, J=13.3 Hz, 1H), 7.92 (d, J=8.3 Hz, 2H), 7.70 (d, J=8.0 Hz, 1H), 7.57 (d, J=13.4 Hz, 1H), 7.37-7.28 (m, 2H), 7.19 (td, J=6.2, 1.8 Hz, 2H), 7.04 (d, J=8.4 Hz, 2H), 5.53 (s, 2H), 1.56 (s, 9H). HRMS (ESI-MS) m/z: calcd.: 379.1652 [MH$^+$], found: 379.1657 [MH$^+$]. Anal. calcd. for C$_{22}$H$_{22}$N$_2$O$_4$: C, 69.83; H, 5.86; N, 7.40, found: C, 69.81; H, 5.92; N, 7.42.

tert-Butyl 4-((2-(2-nitroethyl)-1H-indol-1-yl)methyl)benzoate (25)

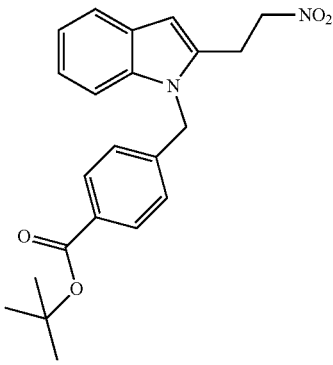 [SMILES: CC(C)(C)OC(=O)c1ccc(Cn2c(CC[N+](=O)[O-])cc3ccccc32)cc1]

To a solution of (E)-tert-butyl 4-((2-(2-nitrovinyl)-1H-indol-1-yl)methyl)benzoate (24) (15.0 g; 39.7 mmol) in CHCl$_3$ (750 mL) and $^i$propanol (75 mL) silica gel (75 g) and NaBH$_4$ (47.6 mmol; 1.80 g) were added and the mixture stirred over night at room temperature. Water (100 mL) was added dropwise while stirring, the mixture filtered over a pad of celite, the organic layer dried (Na$_2$SO$_4$) and purified by cc (SiO$_2$; CH$_2$Cl$_2$). Yield 11.18 g (29.4 mmol, 74%) yellow crystals from CH$_2$Cl$_2$; mp.: 150.4-152.2° C.; IR (KBr): 1704, 1555 cm$^{-1}$; $^1$H NMR (300 MHz, CDCl$_3$) δ 7.94-7.87 (m, 2H), 7.60 (dd, J=6.5, 1.7 Hz, 1H), 7.23-7.09 (m, 3H), 6.98 (d, J=8.3 Hz, 2H), 6.41 (s, 1H), 5.40 (s, 2H), 4.63 (t, J=7.3 Hz, 2H), 3.38 (t, J=7.3 Hz, 2H), 1.56 (s, 9H). HRMS (ESI-MS) m/z: calcd.: 381.1809 [MH$^+$], found: 381.1814 [MH$^+$]; Anal. calcd. for C$_{22}$H$_{24}$N$_2$O$_4$: C, 69.46; H, 6.36; N, 7.36; found: C, 69.29; H, 6.33; N, 7.19.

tert-Butyl 4-((2-(2-aminoethyl)-1H-indol-1-yl)methyl)benzoate hydrochloride (26)

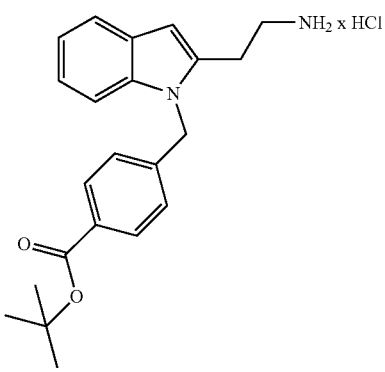

To a stirred solution of tert-butyl 4-((2-(2-nitroethyl)-1H-indol-1-yl)methyl)benzoate (25) (10.80 g; 28.4 mmol) in HOAc (108 mL) zinc dust (170 mmol; 11.13 g) was added in small portions at 20° C. After 4 h, ice was added (250 g) and the mixture alkalized with aqueous ammonia (25%) till pH=14. The mixture was filtered, the aqueous layer extracted with ethyl acetate (3×100 mL), the combined organic layers dried (Na$_2$SO$_4$) and the solvent removed under reduced pressure. The remaining solid was dissolved in THF (10 mL), the solution cooled to 0° C. and HCl (5-6N in $^i$propanol) was added dropwise till pH=2. Et$_2$O was added whilst stirring, the precipitating hydrochloride filtered off and washed with Et$_2$O. Yield 9.60 g (24.8 mmol, 84%) colorless crystals; mp.: 208.9-210.2° C.; IR (KBr): 3446, 1718, 1506 cm$^{-1}$; $^1$H NMR (300 MHz, DMSO) δ 7.86 (s, 2H), 7.82 (d, J=8.3 Hz, 2H), 7.54 (d, J=6.7 Hz, 1H), 7.35 (d, J=7.7 Hz, 1H), 7.10-6.99 (m, 4H), 6.46 (s, 1H), 5.54 (s, 2H), 3.08 (d, J=7.3 Hz, 2H), 2.99 (d, J=7.4 Hz, 2H), 1.51 (s, 9H). HRMS (ESI-MS) m/z: calcd.: 351.2067[MH$^+$], found: 351.2075[MH$^+$]; Anal. calcd. for C$_{22}$H$_{27}$ClNO$_2$: C, 68.29; H, 7.03; N, 7.24; found: C, 68.08; H, 7.04; N, 7.07.

Ethyl 5-(4-(tert-butoxycarbonyl)benzyl)-2,3,4,5-tetrahydro-1H-pyrido[4,3-b]indole-1-carboxylate (27)

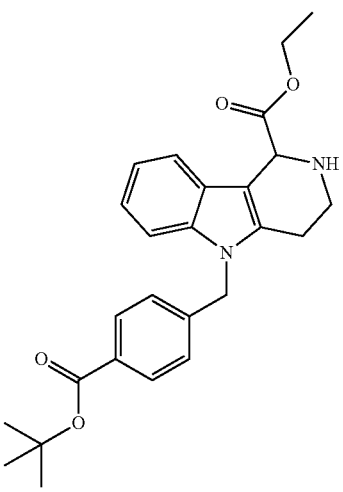 [SMILES: CCOC(=O)C1NCCc2c1c1ccccc1n2Cc1ccc(C(=O)OC(C)(C)C)cc1]

To a stirred solution of tert-butyl 4-((2-(2-aminoethyl)-1H-indol-1-yl)methyl)benzoate hydrochloride (26) (9.00 g; 23.3 mmol) in MeOH (200 mL) ethyl glyoxalate (5.56 mL; 50% in toluene) and silica gel (18.0 g) were added and the mixture stirred for 1 h. The solvents were removed under reduced pressure and the product purified by cc (SiO$_2$; CH$_2$Cl$_2$, MeOH, NH$_3$ (25%), 10:1:0.1) (dry load method). Yield 9.90 g (22.8 mmol, 98%) yellow foam; IR (KBr): 3049, 2931, 1733, 1712 cm$^{-1}$; $^1$H NMR (300 MHz, CDCl$_3$): δ 7.89 (d, J=8.3 Hz, 2H), 7.79-7.72 (m, 1H), 7.21-7.08 (m, 3H), 7.03 (d, J=8.3 Hz, 2H), 5.33 (d, J=17.6 Hz, 1H), 5.26 (d, J=17.4 Hz, 1H), 4.94 (s, 1H), 4.35-4.10 (m, 2H), 3.49 (ddd, J=13.0, 9.1, 4.7 Hz, 1H), 3.24 (ddd, J=12.5, 5.4, 4.0 Hz, 1H), 2.81-2.53 (m, 1H), 2.38 (s, 1H), 1.56 (s, 9H), 1.32 (t, J=7.1 Hz, 3H). HRMS (ESI-MS) m/z: calcd.: 435.2278 [MH$^+$], found: 435.2285 [MH$^+$]; Anal. calcd. for C$_{26}$H$_{30}$N$_2$O$_4$+0.5 H$_2$O: C, 70.41; H, 7.04; N, 6.32, found: C, 70.34; H, 6.79; N, 6.24.

tert-Butyl 4-((2-methyl-1,3-dioxo-2,3,5,6-tetrahydro-1H-imidazo[1',5':1,2]pyrido[4,3-b]indol-7(11cH)-yl)methyl)benzoate (28a)

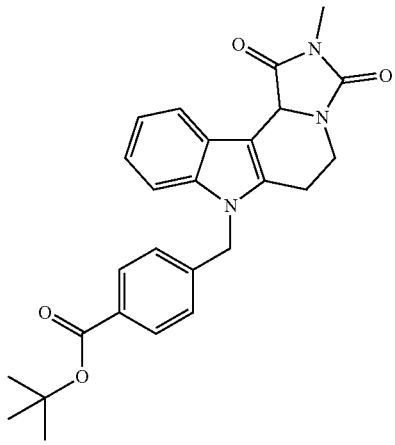 [SMILES: CN1C(=O)C2c3c(n(Cc4ccc(C(=O)OC(C)(C)C)cc4)c4ccccc34)CCN2C1=O]

Ethyl 5-(4-(tert-butoxycarbonyl)benzyl)-2,3,4,5-tetrahydro-1H-pyrido[4,3-b]indole-1-carboxylate (27) (3.00 g; 6.90 mmol) was dissolved in acetonitrile (15.0 mL). Diisopropylethylamine (3.0 mL) was added to the stirred mixture. After addition of N-succinimidyl-N-methylcarbamate (1.31 g; 7.60 mmol) stirring was continued for 16 h at rt. The mixture was poured into water and the crude product was extracted with EtOAc (3×50 mL). The combined organic layers were dried (Na$_2$SO$_4$) and evaporated. Yield 1.44 g (3.23 mmol, 47%) colorless foam after cc (CH$_2$Cl$_2$, ethyl acetate 10:1). $^1$H NMR (300 MHz, CDCl$_3$): δ 8.12-8.01 (m, 1H), 7.84 (d, J=8.3 Hz, 2H), 7.19-7.08 (m, 3H), 6.96 (d, J=8.3 Hz, 2H), 5.34 (t, J=1.8 Hz, 1H), 5.24 (s, 2H), 4.48 (dd, J=13.7, 6.0 Hz, 1H), 3.20-3.05 (m, 1H), 2.97 (s, 3H), 2.88-2.71 (m, 1H), 2.56 (dd, J=16.0, 4.7 Hz, 1H), 1.51 (s, 9H).

4-((2-Methyl-1,3-dioxo-2,3,5,6-tetrahydro-1H-imidazo[1',5':1,2]pyrido[4,3-b]indol-7(11cH)-yl)methyl)benzoic acid (29a)

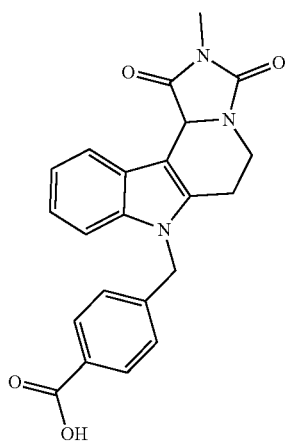 [SMILES: CN1C(=O)C2c3c(n(Cc4ccc(C(=O)O)cc4)c4ccccc34)CCN2C1=O]

tert-Butyl 4-((2-methyl-1,3-dioxo-2,3,5,6-tetrahydro-1H-imidazo[1',5':1,2]pyrido[4,3-b]indol-7(11cH)-yl)methyl)benzoate (28a) (1.00 g; 2.24 mmol) was dissolved in trifluoro acetic acid (10.0 mL) and the mixture stirred for 15 min. at room temperature. The solution was added to water (100 mL), the precipitating product collected by filtration and dried in vacuo. mp.: 267.2-269.6° C.; IR (KBr): 1717, 1678 cm$^{-1}$; $^1$H NMR (300 MHz, DMSO) δ 12.91 (s, 1H), 7.94-7.89 (m, 1H), 7.86 (d, J=8.2 Hz, 2H), 7.43 (d, J=7.1 Hz, 1H), 7.15 (d, J=8.2 Hz, 2H), 7.13-7.05 (m, 2H), 5.52 (s, 1H), 5.46 (s, 2H), 4.33 (dd, J=13.6, 4.9 Hz, 1H), 3.28-3.15 (m, 2H), 2.86 (s, 3H), 2.78 (s, 1H). HRMS (ESI-MS) m/z: calcd.: 390.1361 [MH$^+$], found: 390.1360[MH$^+$]; Anal. calcd. for C$_{22}$H$_{19}$N$_3$O$_4$+0.5 H$_2$O: C, 66.32; H, 5.06; N, 10.55; found: C, 66.01; H, 5.09; N, 10.19.

4-((2-Methyl-1,3-dioxo-2,3,5,6-tetrahydro-1H-imidazo[1',5':1,2]pyrido[4,3-b]indol-7(11cH)-yl)methyl)-N—((tetrahydro-2H-pyran-2-yl)oxy)benzamide (30a)

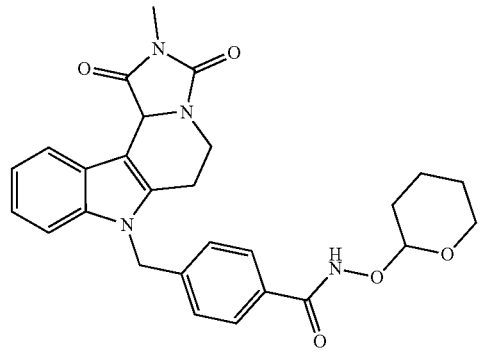 [SMILES: CN1C(=O)C2c3c(n(Cc4ccc(C(=O)NOC5CCCCO5)cc4)c4ccccc34)CCN2C1=O]

4-((2-Methyl-1,3-dioxo-2,3,5,6-tetrahydro-1H-imidazo[1',5':1,2]pyrido[4,3-b]indol-7(11cH)-yl)methyl)benzoic acid (29a) (0.78 g, 2.00 mmol) was dissolved in DMF (15.0 mL) and BOP (1.2 equ.), EtN(iProp)$_2$ (0.78 mL) and O-(tetrahydro-2H-pyran-2-yl)hydroxylamine (3.0 equ.) were added. The solution was stirred over night at room temperature, poured into water and extracted with ethyl acetate (3×50 mL). CC (SiO$_2$, CH$_2$Cl$_2$, MeOH (10:1) and removal of the solvent under reduced pressure yielded the product as colorless foam; mp.: 184.7-186.9° C.; $^1$H NMR (300 MHz, DMSO) δ 11.58 (s, 1H), 7.91 (dd, J=6.6, 2.1 Hz, 1H), 7.67 (d, J=8.2 Hz, 2H), 7.43 (d, J=7.2 Hz, 1H), 7.16-7.04 (m, 4H), 5.52 (s, 1H), 5.44 (s, 2H), 4.95 (s, 1H), 4.33 (dd, J=13.5, 5.1 Hz, 1H), 3.49 (d, J=11.3 Hz, 1H), 3.28-3.14 (m, 1H), 2.87 (s, 3H), 2.76 (d, J=17.0 Hz, 2H), 2.09 (s, 1H), 1.61 (d, J=49.2 Hz, 6H). HRMS (ESI-MS) m/z: calcd.: 489.2132 [MH$^+$], found: 489.2133 [MH$^+$].

N-Hydroxy-4-((2-methyl-1,3-dioxo-2,3,5,6-tetrahydro-1H-imidazo[1',5':1,2]pyrido[4,3-b]indol-7(11cH)-yl)methyl)benzamide (31a)

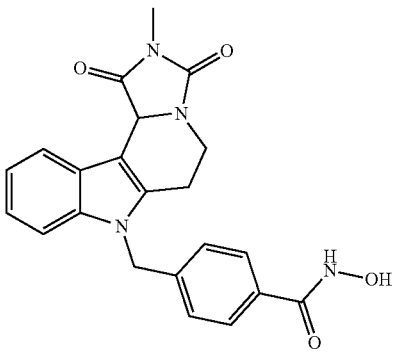 [SMILES: CN1C(=O)C2c3c(n(Cc4ccc(C(=O)NO)cc4)c4ccccc34)CCN2C1=O]

mp.: 248.1-251.7° C.; IR (KBr): 3251, 1769, 1690, 1650 cm$^{-1}$; $^1$H NMR (300 MHz, DMSO) δ 11.14 (s, 1H), 9.02 (d, J=1.7 Hz, 1H), 7.91 (dd, J=6.7, 2.1 Hz, 1H), 7.65 (d, J=8.2 Hz, 2H), 7.44 (dd, J=6.8, 1.7 Hz, 1H), 7.16-7.09 (m, 3H), 7.08-7.03 (m, 1H), 5.52 (s, 1H), 5.42 (s, 2H), 4.33 (dd, J=13.7, 4.9 Hz, 1H), 3.29-3.14 (m, 1H), 2.87 (s, 3H), 2.77 (d, J=16.5 Hz, 2H). HRMS (ESI-MS) m/z: calcd.: 405.1557 [MH$^+$], found: 405.1558 [MH$^+$]; Anal. calc. for $C_{22}H_{20}N_4O_4$+0.5 $H_2O$: C, 63.91; H, 5.12; N, 13.55; found: C, 64.10; H, 5.13; N, 13.19.

tert-Butyl 4-((2-methyl-1,4-dioxo-1,3,4,6,7,12c-hexahydropyrazino[1',2':1,2]pyrido[4,3-b]indol-8(2H)-yl)methyl)benzoate (28b)

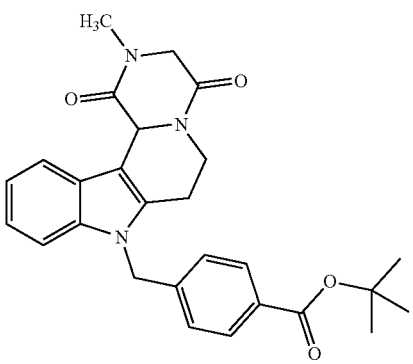 [SMILES: CN1CC(=O)N2CCc3c(c4ccccc4n3Cc3ccc(C(=O)OC(C)(C)C)cc3)C2C1=O]

Ethyl 5-(4-(tert-butoxycarbonyl)benzyl)-2,3,4,5-tetrahydro-1H-pyrido[4,3-b]indole-1-carboxylate (27) (3.55 g, 8.16 mmol) was dissolved in 50 mL of dichloromethane and cooled to −50° C. 0.68 mL (8.57 mmol) of chloroacetyl chloride and 1.55 mL (8.98 mmol) of diisopropylethylamine were added. The solution was brought to 0° C. within 1 h and the solvent was removed at this temperature under reduced pressure.

30 mL methylamine (40% in methanol) was added and the solution was stirred overnight at room temperature. 80 mL of ethyl acetate and 40 mL of water were added, the organic layer was separated, dried over Na$_2$SO$_4$ and the solvent removed.

Yield 2.40 g; 5.22 mmol (64%) yellow foam after silica gel chromatography with 1. ethyl acetate, 2. ethyl acetate/acetonitrile 1:1. mp.: 121.1-124.0° C.; IR (KBr): 1712, 1669 cm$^{-1}$; $^1$H NMR (300 MHz, DMSO) δ 7.91 (d, J=7.4 Hz, 1H), 7.84-7.78 (m, 2H), 7.37 (d, J=7.9 Hz, 1H), 7.12 (d, J=8.3 Hz, 2H), 7.09-6.94 (m, 2H), 5.59 (s, 1H), 5.44 (t, J=10.9 Hz, 2H), 4.63 (d, J=12.1 Hz, 1H), 4.16 (d, J=17.6 Hz, 1H), 3.96 (d, J=17.8 Hz, 1H), 2.99 (dd, J=12.5, 7.8 Hz, 1H), 2.90 (s, 3H), 2.78 (d, J=5.2 Hz, 2H), 1.50 (s, 9H). HRMS (ESI-MS) m/z: calcd.: 482.2050 [MNa$^+$], found: 482.2055 [MNa$^+$]; Anal. calcd. for $C_{27}H_{29}N_3O_4$+1 $H_2O$: C, 67.91; H, 6.54; N, 8.80; found: C, 67.86; H, 6.22; N, 8.64.

4-((2-Methyl-1,4-dioxo-1,3,4,6,7,12c-hexahydropyrazino[1',2':1,2]pyrido[4,3-b]indol-8(2H)-yl)methyl)benzoic acid (29b)

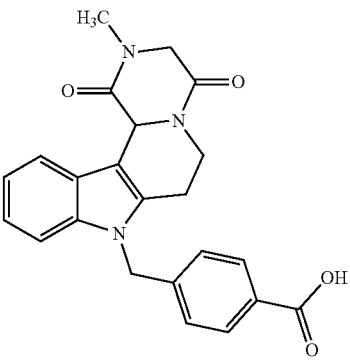 [SMILES: CN1CC(=O)N2CCc3c(c4ccccc4n3Cc3ccc(C(=O)O)cc3)C2C1=O]

tert-Butyl 4-((2-methyl-1,4-dioxo-1,3,4,6,7,12c-hexahydropyrazino[1',2':1,2]pyrido[4,3-b]indol-8(2H)-yl)methyl)benzoate (28b) (0.46 g, 1.00 mmol) was dissolved in 20 mL of dichloromethane. After addition of 10 mL trifluoroacetic acid stirring at rt was continued for 16 h. The solution was diluted with 40 mL of dichloromethane and the organic solution was washed with water. Removal of the solvent left a light brown solid. Yield 0.40 g (quant.). mp.: 283.3-287.4° C.; IR (KBr): 1700, 1669 cm$^{-1}$; $^1$H NMR (300 MHz, DMSO) δ 12.75 (s, 1H), 7.91 (d, J=7.9 Hz, 1H), 7.86 (d, J=8.2 Hz, 2H), 7.38 (d, J=7.9 Hz, 1H), 7.12 (d, J=8.2 Hz, 2H), 7.03 (dt, J=22.5, 7.3 Hz, 2H), 5.59 (s, 1H), 5.55-5.38 (m, 2H), 4.63 (d, J=12.1 Hz, 1H), 4.16 (d, J=17.7 Hz, 1H), 3.96 (d, J=17.7 Hz, 1H), 3.06-2.94 (m, 1H), 2.90 (s, 3H), 2.80 (s, 2H). HRMS (ESI-MS) m/z: calcd.: 402.1452 [MH]$^-$, found: 402.1452 [MH]$^-$.

4-((2-Methyl-1,4-dioxo-1,3,4,6,7,12c-hexahydropyrazino[1',2':1,2]pyrido[4,3-b6]indol-8(2H)-yl)methyl)-N—((tetrahydro-2H-pyran-2-yl)oxy)benzamide (30b)

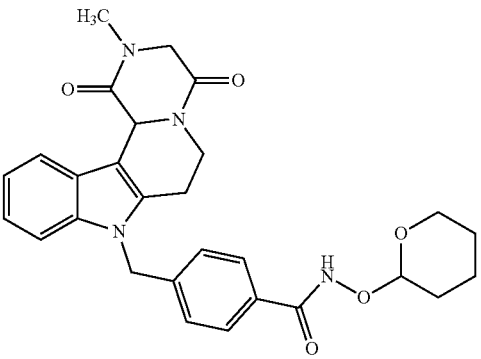 [SMILES: CN1CC(=O)N2CCc3c(c4ccccc4n3Cc3ccc(C(=O)NOC4CCCCO4)cc3)C2C1=O]

4-((2-Methyl-1,4-dioxo-1,3,4,6,7,12c-hexahydropyrazino[1',2':1,2]pyrido[4,3-b]indol-8(2H)-yl)methyl)benzoic acid (29b) (0.31 g, 0.77 mmol) was dissolved in 60 mL of tetrahydrofuran. 0.41 g (0.92 mmol) BOP, 0.52 mL 83.00 mmol) diisopropylethylamine and 0.23 g (2.00 mmol) NH$_2$OTHP were added. The mixture was stirred at room temperature for 3.5 h. TLC-control: SiO$_2$; dichloromethane/methanol 10:1. The solvent was removed under reduced pressure and the residue was dissolved in 100 mL of ethyl acetate and 50 mL of water. The organic layer was separated and the volume of the solvent was reduced until crystallization occurs. The crystals were filtered of, washed with diethylether and dried.

Yield 0.22 g; 0.44 mmol (57%) colorless crystals. mp.: 188.7-192.8° C.; IR (KBr): 1675, 1653 cm$^{-1}$; $^1$H NMR (300 MHz, DMSO) δ 11.58 (s, 1H), 7.91 (d, J=7.7 Hz, 1H), 7.67 (d, J=8.1 Hz, 2H), 7.38 (d, J=8.0 Hz, 1H), 7.11 (d, J=8.2 Hz, 2H), 7.07-6.95 (m, 2H), 5.59 (s, 1H), 5.54-5.34 (m, 2H), 4.95 (s, 1H), 4.63 (d, J=12.2 Hz, 1H), 4.16 (d, J=17.7 Hz, 1H), 4.03 (d, J=7.2 Hz, 1H), 3.96 (d, J=17.6 Hz, 1H), 3.49 (d, J=10.7 Hz, 1H), 3.06-2.94 (m, 1H), 2.89 (s, 3H), 2.81 (s, 2H), 1.61 (d, J=49.1 Hz, 6H). HRMS (ESI-MS) m/z: calcd.: 503.2289 [MH$^+$], found: 503.2289 [MH$^+$]; Anal. calcd. for C$_{28}$H$_{30}$N$_4$O$_5$+0.75 H$_2$O: C, 65.17; H, 6.15; N, 10.86; found: C, 65.11; H, 5.95; N, 10.87.

N-hydroxy-4-((2-methyl-1,4-dioxo-1,3,4,6,7,12c-hexahydropyrazino[1',2':1,2]pyrido[4,3-b]indol-8(2H)-yl)methyl)benzamide (31b)

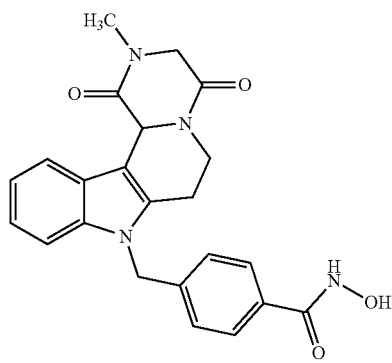 [SMILES: CN1CC(=O)N2CCc3c(c4ccccc4n3Cc3ccc(C(=O)NO)cc3)C2C1=O]

4-((2-Methyl-1,4-dioxo-1,3,4,6,7,12c-hexahydropyrazino[1',2':1,2]pyrido[4,3-b]indol-8(2H)-yl)methyl)-N-((tetrahydro-2H-pyran-2-yl)oxy)benzamide (30b) (0.18 g, 0.36 mmol) was dissolved in a mixture of 20 mL methanol, 20 mL tetrahydrofuran and 20 mL of dichloromethane. After addition of 0.2 mL of 6 N HCl in isopropanol the mixture was stirred for 45 min. at room temperature. TLC-control: SiO$_2$; dichloromethane/methanol 10:1. The solvent was removed, ethanol was added and the mixture heated to 70° C. for 15 min. After cooling the product was filtered of and dried.

Yield 0.12 g, 0.29 mmol (80%) light beige powder. mp.: 204.1-205.6° C.; IR (KBr): 1677, 1653 cm$^{-1}$; $^1$H NMR (300 MHz, DMSO) δ 11.16 (s, 1H), 9.02 (s, 1H), 7.90 (d, J=7.7 Hz, 1H), 7.66 (d, J=8.2 Hz, 2H), 7.39 (d, J=8.0 Hz, 1H), 7.08 (d, J=8.2 Hz, 3H), 7.00 (dd, J=14.7, 7.4 Hz, 1H), 5.59 (s, 1H), 5.51-5.34 (m, 2H), 4.64 (d, J=12.2 Hz, 11), 4.16 (d, J=17.7 Hz, 1H), 3.95 (d, J=17.7 Hz, 1H), 3.00 (dd, J=12.1, 7.8 Hz, 1H), 2.89 (s, 3H), 2.82 (s, 2H). HRMS (ESI-MS) m/z: calcd.: 419.1714 [MH$^+$], found: 419.1715 [MH$^+$].

Example 3: Synthesis of Compound 41

Scheme 4a: Synthesis of compound 41 with 33, 34, 35, 36, 37, 38, 39, 40 as examples.

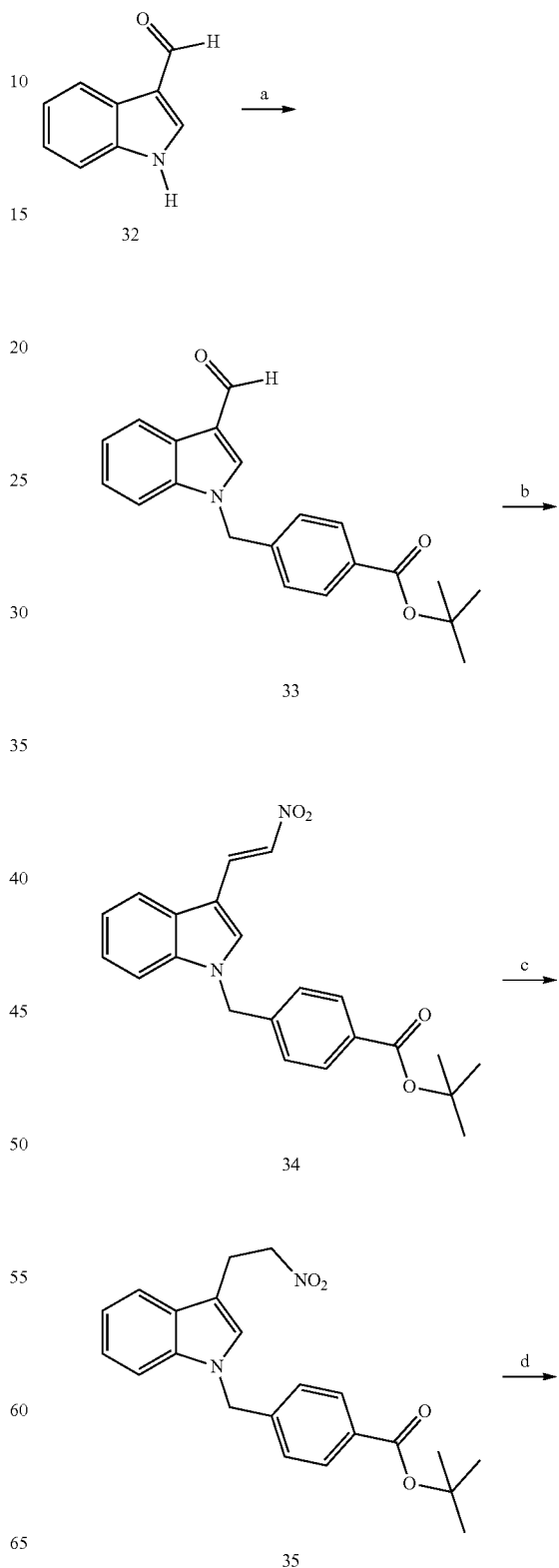

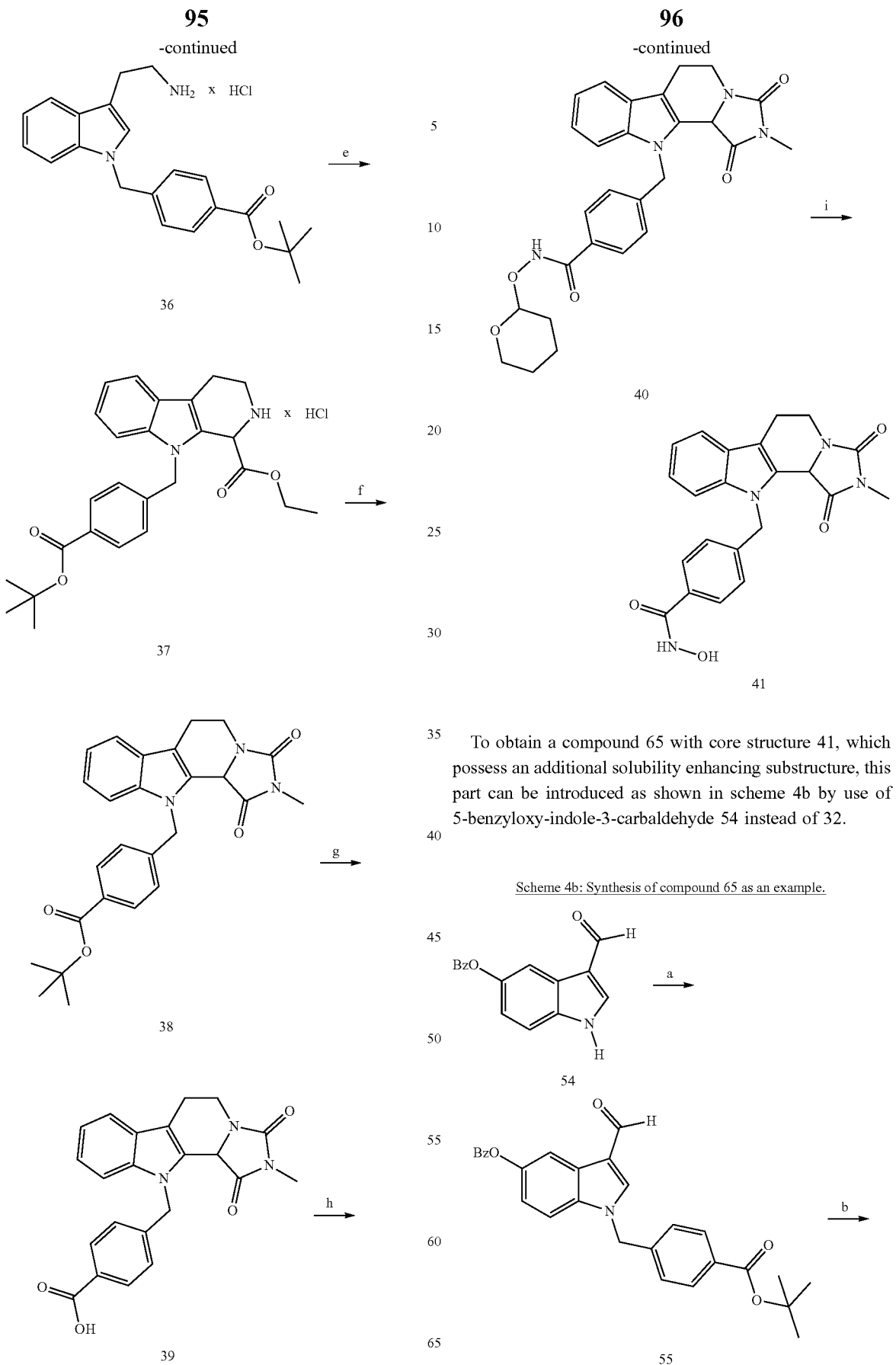
To obtain a compound 65 with core structure 41, which possess an additional solubility enhancing substructure, this part can be introduced as shown in scheme 4b by use of 5-benzyloxy-indole-3-carbaldehyde 54 instead of 32.
Scheme 4b: Synthesis of compound 65 as an example.

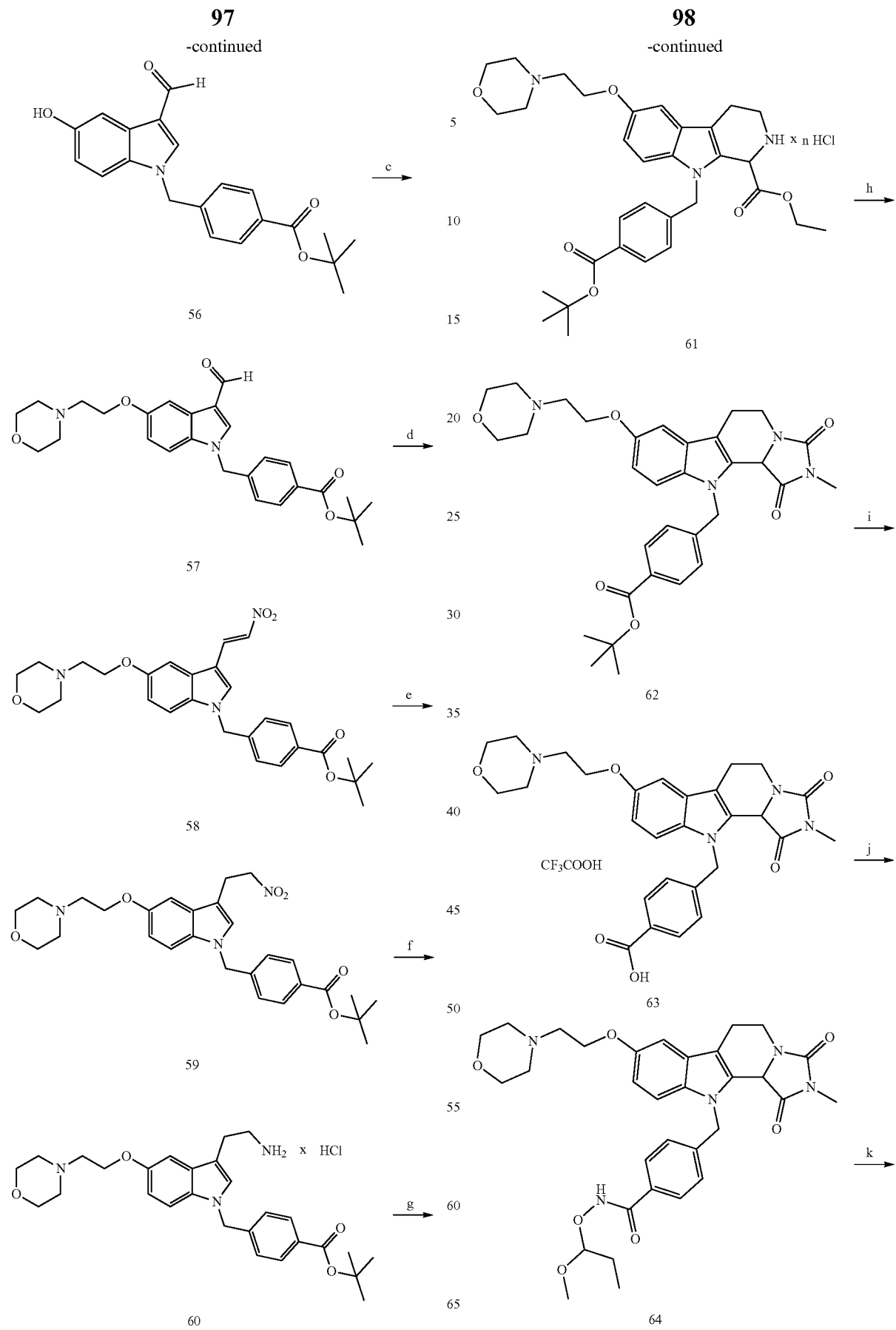

-continued

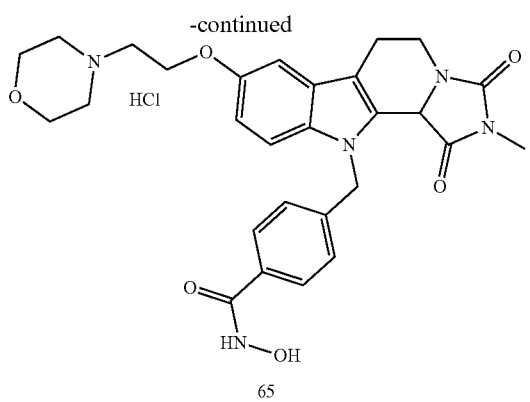

65 tert-Butyl 4-((3-formyl-1H-indol-1-yl)methyl)benzoate (33)

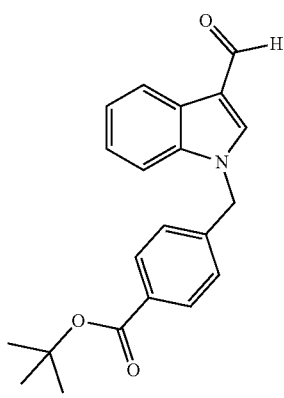 [SMILES: CC(C)(C)OC(=O)c1ccc(Cn2cc(C=O)c3ccccc32)cc1]

Preparation from 1H-indole-3-carbaldehyde (32) (9.60 g, 66.2 mmol) and tert-butyl 4-(bromomethyl)benzoate (18.0 g, 66.4 mmol) as described for 23.

Yield 18.2 g (52 mmol, 78%) colorless solid. mp.: 112.7-114.9° C.; IR(KBr): 1704, 1664 cm$^{-1}$; $^1$H NMR (300 MHz, CDCl$_3$) δ 10.02 (s, 1H), 8.34 (dd, J=6.2, 2.0 Hz, 1H), 7.96 (d, J=8.3 Hz, 2H), 7.74 (s, 1H), 7.36-7.26 (m, 3H), 7.20 (d, J=8.3 Hz, 2H), 5.42 (s, 2H), 1.57 (s, 9H).

(E)-tert-Butyl 4-((3-(2-nitrovinyl)-1H-indol-1-yl)methyl)benzoate (34)

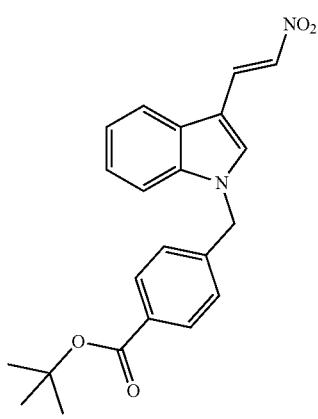 [SMILES: CC(C)(C)OC(=O)c1ccc(Cn2cc(/C=C/[N+](=O)[O-])c3ccccc32)cc1]

Preparation from tert-Butyl 4-((3-formyl-1H-indol-1-yl)methyl)benzoate (33) (10.0 g, 29.8 mmol) as described for 24. Yield 11.17 g (29.5 mmol, 99%) yellow crystals. mp.: 144.2-146.7° C.; IR (KBr): 1714, 1619, 1320 cm$^{-1}$; $^1$H NMR (300 MHz, CDCl$_3$) δ 8.26 (d, J=13.5 Hz, 1H), 7.96 (d, J=8.4 Hz, 2H), 7.83-7.78 (m, 1H), 7.76 (s, 1H), 7.58 (s, 1H), 7.38-7.28 (m, 3H), 7.18 (d, J=8.4 Hz, 2H), 5.41 (s, 2H), 1.57 (s, 9H).

tert-Butyl 4-((3-(2-nitroethyl)-1H-indol-1-yl)methyl)benzoate (35)

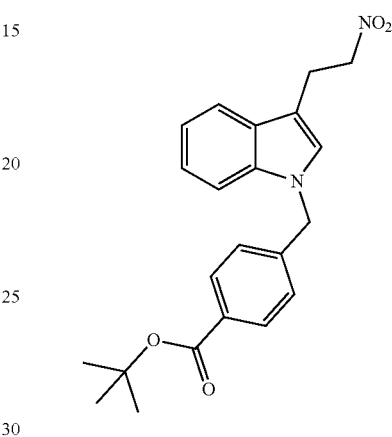

Preparation from (E)-tert-Butyl 4-((3-(2-nitrovinyl)-1H-indol-1-yl)methyl)benzoate (34) (10.5 g, 27.7 mmol) as described for 25.

Yield 6.30 g (16.6 mmol, 59%) light yellow oil after cc (SiO$_2$, CH$_2$Cl$_2$). IR (KBr): 1707, 1549, 1311 cm$^{-1}$; $^1$H NMR (300 MHz, CDCl$_3$) δ 7.95-7.88 (m, 2H), 7.61-7.56 (m, 1H), 7.23-7.12 (m, 3H), 7.10 (d, J=8.4 Hz, 2H), 6.99 (s, 1H), 5.32 (s, 2H), 4.67 (t, J=7.2 Hz, 2H), 3.50 (t, J=7.1 Hz, 2H), 1.56 (s, 9H).

tert-Butyl 4-((3-(2-aminoethyl)-1H-indol-1-yl)methyl)benzoate hydrochloride (36)

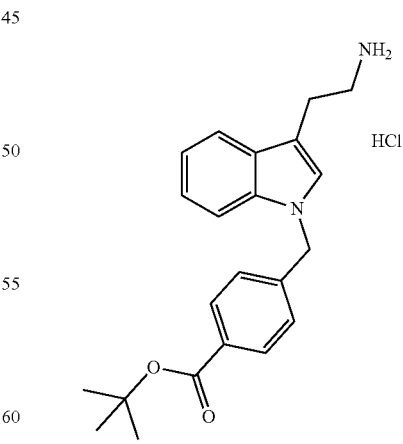

Preparation from tert-Butyl 4-((3-(2-nitroethyl)-1H-indol-1-yl)methyl)benzoate (35) (6.0 g, 15.8 mmol) as described for 26. Yield 3.60 g (10.3 mml, 65%) colorless crystals. mp.: 196.9-198.5° C.; IR (KBr): 1714, 1297 cm$^{-1}$; $^1$H NMR (300 MHz, CDCl$_3$) δ 8.27 (s, 2H), 7.88 (d, J=8.3

Hz, 2H), 7.61 (d, J=6.8 Hz, 1H), 7.15-7.02 (m, 6H), 5.26 (s, 2H), 3.23 (s, 4H), 1.54 (s, 9H).

Ethyl 9-(4-(tert-butoxycarbonyl)benzyl)-2,3,4,9-tetrahydro-1H-pyrido[3,4-b]indole-1-carboxylate hydrochloride (37)

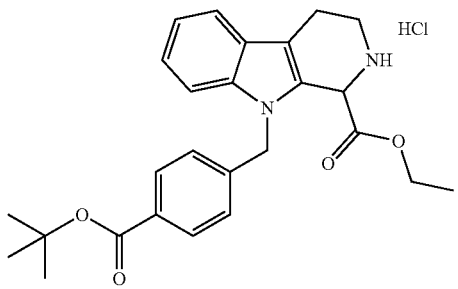 [SMILES: CCOC(=O)C1NCCc2c1n(Cc1ccc(C(=O)OC(C)(C)C)cc1)c1ccccc21 ; Cl]

Preparation from tert-Butyl 4-((3-(2-aminoethyl)-1H-indol-1-yl)methyl)benzoate hydrochloride (36) (3.50 g, 9.07 mmol) as described for 27 without purification by cc.

Yield 2.45 g (5.10 mmol, 56%) colorless crystals from a saturated solution in MeOH by addition of Et$_2$O. mp.: 211.2-214.9° C.; IR (KBr): 1747, 1714, 1253 cm$^{-1}$; $^1$H NMR (300 MHz, DMF) δ 10.11 (s, 2H), 7.80 (d, J=8.3 Hz, 2H), 7.57 (d, J=6.9 Hz, 1H), 7.17 (dd, J=15.8, 6.4 Hz, 2H), 7.12-7.07 (m, 3H), 5.81 (s, 1H), 5.63 (q, J=17.5 Hz, 2H), 4.17 (tt, J=14.3, 7.1 Hz, 1H), 4.02-3.86 (m, 1H), 3.72 (d, J=12.8 Hz, 1H), 3.53 (s, 1H), 3.04 (d, J=4.8 Hz, 2H), 1.51 (s, 9H), 1.08 (t, J=7.1 Hz, 3H).

tert-Butyl 4-((2-methyl-1,3-dioxo-2,3,5,6-tetrahydro-1H-imidazo[1',5':1,2]pyrido[3,4-b]indol-11(11bH)-yl)methyl)benzoate (38)

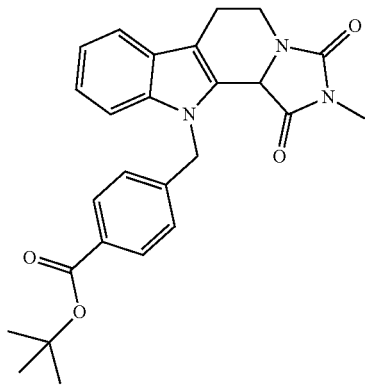 [SMILES: CN1C(=O)C2c3c(c4ccccc4n3Cc3ccc(C(=O)OC(C)(C)C)cc3)CCN2C1=O]

Preparation from ethyl 9-(4-(tert-butoxycarbonyl)benzyl)-2,3,4,9-tetrahydro-1H-pyrido[3,4-b]indole-1-carboxylate hydrochloride (37) (2.45 g, 5.10 mmol) as described for 28a.

Yield 2.05 g (4.60 mmol, 90%) colorless foam after cc (SiO$_2$, ethyl acetate). mp.: 120.3-123.0° C.; IR (KBr): 1714, 1461 cm$^{-1}$; $^1$H NMR (300 MHz, CDCl$_3$) δ 7.88 (d, J=8.4 Hz, 2H), 7.54 (d, J=7.5 Hz, 1H), 7.25-7.11 (m, 3H), 6.99 (d, J=8.4 Hz, 2H), 6.16 (d, J=17.3 Hz, 1H), 5.64 (d, J=17.2 Hz, 1H), 5.10 (s, 1H), 4.57-4.45 (m, 1H), 3.03 (s, 3H), 3.01 (d, J=7.9 Hz, 1H), 2.97-2.89 (m, 1H), 2.89-2.81 (m, 1H), 1.55 (s, 9H).

4-((2-Methyl-1,3-dioxo-2,3,5,6-tetrahydro-1H-imidazo[1',5':1,2]pyrido[3,4-b]indol-11(11bH)-yl)methyl)-N—((tetrahydro-2H-pyran-2-yl)oxy)benzamide (40)

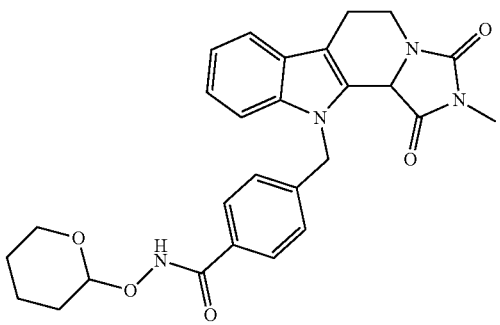 [SMILES: CN1C(=O)C2c3c(c4ccccc4n3Cc3ccc(C(=O)NOC4CCCCO4)cc3)CCN2C1=O]

Preparation from 4-((2-methyl-1,3-dioxo-2,3,5,6-tetrahydro-1H-imidazo[1',5':1,2]pyrido[3,4-b]indol-11(11bH)-yl)methyl)benzoic acid (39) (1.62 g, 4.16 mmol) as described for 30a.

The crude 4-((2-methyl-1,3-dioxo-2,3,5,6-tetrahydro-1H-imidazo[1',5':1,2]pyrido[3,4-b]indol-11(11 bH)-yl)methyl)benzoic acid (39) used therefore was obtained in quantitative yield from tert-butyl 4-((2-methyl-1,3-dioxo-2,3,5,6-tetrahydro-1H-imidazo[1',5':1,2]pyrido[3,4-b]indol-11(11 bH)-yl)methyl)benzoate (38) following the procedure described for 29a und used without purification.

Yield 0.86 g (1.76 mmol, 42%) colorless foam. mp.: 151.2-154.0° C.; IR (KBr): 2946, 1713 cm$^{-1}$; $^1$H NMR (300 MHz, CDCl$_3$) δ 7.65 (d, J=8.3 Hz, 2H), 7.55 (d, J=7.6 Hz, 1H), 7.21 (d, J=3.6 Hz, 2H), 7.19-7.11 (m, 1H), 7.02 (d, J=7.9 Hz, 2H), 6.13 (d, J=17.2 Hz, 1H), 5.64 (d, J=17.1 Hz, 1H), 5.08 (d, J=16.0 Hz, 2H), 4.52 (d, J=9.1 Hz, 1H), 4.02-3.88 (m, 1H), 3.63 (d, J=11.0 Hz, 1H), 3.03 (d, J=3.8 Hz, 3H), 3.00 (s, 1H), 2.90 (dd, J=23.1, 12.0 Hz, 2H), 1.73 (d, J=76.3 Hz, 6H).

N-Hydroxy-4-((2-methyl-1,3-dioxo-2,3,5,6-tetrahydro-1H-imidazo[1',5':1,2]pyrido[3,4-b]indol-11(11bH)-yl)methyl)benzamide (41)

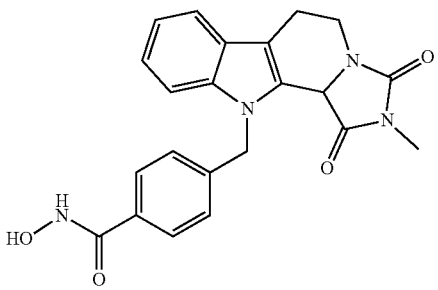 [SMILES: CN1C(=O)C2c3c(c4ccccc4n3Cc3ccc(C(=O)NO)cc3)CCN2C1=O]

Preparation from 4-((2-Methyl-1,3-dioxo-2,3,5,6-tetrahydro-1H-imidazo[1',5':1,2]pyrido[3,4-b]indol-11(11 bH)-yl)methyl)-N—((tetrahydro-2H-pyran-2-yl)oxy)benzamide (40) (0.50 g, 1.02 mmol) as described for 31a.

Yield 225 mg (0.56 mmol, 55%). mp.: 134.5-136.9° C.; IR (KBr): 1710, 1462 cm$^{-1}$; $^1$H NMR (300 MHz, DMSO) δ 11.15 (s, 1H), 9.03 (s, 1H), 7.64 (d, J=8.2 Hz, 2H), 7.52 (d, J=7.1 Hz, 1H), 7.27 (d, J=7.7 Hz, 1H), 7.12 (d, J=6.0 Hz, 1H), 7.06 (d, J=8.1 Hz, 3H), 6.00 (d, J=17.2 Hz, 1H), 5.79-5.61 (m, 2H), 4.32 (dd, J=13.3, 4.8 Hz, 1H), 3.17-3.05 (m, 1H), 2.90 (s, 3H), 2.85-2.72 (m, 2H).

Example 4: Biological Evaluation

Enzymatic Inhibitory Activities on HDACs 2, 6 and 8

HDAC enzyme inhibition assays were conducted by Reaction Biology Corporation (Malvern, Pa., USA) using a ten point dose response curve with half-log serial dilutions, fluorogenic peptides at 50 μM as enzymatic substrates. Substrate for HDAC 2 and 6: fluorogenic peptide from p53 residues 379-382 (RHKK(Ac)AMC). Substrate for HDAC-8: fluorogenic peptide from p53 residues 379-382 (RHK(Ac)K(Ac)AMC). The investigated compounds inhibited HDAC6 selectively, on the basis of the enzymatic inhibitory study.

TABLE 1

Inhibition of HDAC-subtypes HDAC2, HDAC6 and HDAC8 ($IC_{50}$-values [nM])[a].

| Compound | Cpd. No. | HDAC2 | HDAC6 | HDAC8 |
|---|---|---|---|---|
| | 21 | 3 135 ± 885 | 2.41 ± 0.76 | 121 ± 10 |
| | (R)-21 | 13 000 | 7.05 | 1 970 |
| | (S)-21 | 1 795 | 3.02 | 364 |
| | 31a | 9 580 ± 380 | 8.99 ± 1.11 | 1 095 ± 75 |

TABLE 1-continued

Inhibition of HDAC-subtypes HDAC2, HDAC6 and HDAC8 ($IC_{50}$-values [nM])[a].

| Compound | Cpd. No. | HDAC2 | HDAC6 | HDAC8 |
|---|---|---|---|---|
| (structure) | 31b | 5 195 ± 565 | 16.45 ± 0.75 | 251.5 ± 32.5 |
| (structure) | 41 | 410 000 ± 700 | 30.7 ± 5.8 | 83 ± 6 |

[a]Compounds were tested in a 10-dose $IC_{50}$ mode with 3-fold serial dilution starting from 100 μM solutions for HDAC2 and HDAC8, respectively starting from 1 μM solutions for HDAC6. $IC_{50}$ values were extracted by curve-fitting the dose/response slopes. TSA was used as an internal standard.
ND: Not Determined.
Assays were performed by Reaction Biology Corporation, USA. Determination in duplicate ± SD.

Cellular Data.

Since acetylated α-tubulin (ac-Tub) accumulates when HDAC6 is inhibited, its extent of accumulation is a valuable surrogate parameter for inhibitory efficiency. MS-275 only blocks the nuclear enzymes HDAC1, 2 and 3, which leads to hyperacetylation of histones without affecting the acetylation status of tubulin and was therefore used as negative control. Due to the poor potency of MS-275 it was used in a concentration of 5 μM. The absence of acetylated histone $H_3$ (ac-$H_3$) revealed that our inhibitors are selective and have no effect on nuclear deacetylases. HSP90 served as loading control. HDAC6 blots underlined that the target enzyme stays intact although being affected by our compounds (FIG. 2).

Cell Culture and Western Blot

MV4-11 (human, biphenotypic B myelomonocytic leukemia, American Type Culture Collection, ATCC Accession No.: CRL-9591) cells were used for the cellular test system. The cells were cultured in Rosewell Park Memorial Institute (RPMI) 1640 medium (Biochrom, Berlin, Germany, CAT #: F1215) supplemented with 10% heat inactivated fetal bovine serum (FBS Superior, Biochrom, CAT #: S0615), 2 mM glutamine (Biochrom, CAT #: K0283) and 1% penicillin and streptomycin (Biochrom, CAT #: A2212). The cells were cultured at 37° C. in a humidified atmosphere enriched with 5% $CO_2$. Etinostat (MS-275, 29) was purchased from Biotrend (Cologne, Germany). Chemicals were blotting or cell culture grade and purchased from commercial suppliers (Carl Roth, Germany: Dimethylsulfoxide (DMSO), NaCl, Tris-(hydroxymethyl)-aminoethan (TRIS), glycerin, ethylenediaminetetraacetic acid (EDTA), bovine serum albumin (IgG free), sodium dodecylsulfate (SDS), ammonium persulfate (APS), glycine, dry milk, Tween 20; Sigma Aldrich, Germany: Nonidet P 40 substitute, N,N;N',N'-Tetraethylethylendiamine (TEMED), protease inhibitor cocktail tablets cOmplete™ (CAT #: 04693116001), phosphatase inhibitor cocktail 2 (CAT #: P5726), Sample buffer according to Lämmli (CAT #: 11337), Dulbecco's phosphate buffered saline (PBS)) or purchased as indicated. Exclusively ultrapure water was used throughout the assays (Astacus Membrane Pure, MembraPure GmbH, Bodenheim, Germany).

The assay was carried out as a modification of Buchwald et al. (Buchwald, Pietschmann, et al. 2010; Buchwald, Pietschmann, et al. 2013; Beyer, Kiweler, et. al. 2017). In brief, the cells were counted using a Neubauer counting chamber and 1,000,000 cells per 5 mL were seeded in every well of a 6 well plate. The cells were allowed to adapt for 2 h and then stimulated with the respective compound at the indicated final concentration (5 nM to 800 nM). The DMSO control concentration corresponded to the maximum concentration of DMSO used in the assay. 10 mM stock solutions in DMSO were stored at −80° C. and diluted 1:100 or 1:1000 with PBS immediately before the stimulation. MS-275 stock solution was stored at a concentration of 5 mM.

The cells were collected on ice after the indicated time, centrifuged at 1000×g at 4° C., the supernatant was removed and cell pellets were washed with cold PBS buffer. After centrifugation at 14200×g at 4° C. and removal of the supernatant, cells were lysed with 120 μL NET-N buffer (100 mM NaCl, 1 mM EDTA, 10 mM TRIS-HCl (pH 8.0), 0.5% Nonidet P-40 (NP-40), 10% glycerin, protease inhibitor cocktail tablets cOmplete™ (1 per 10 mL of buffer), phosphatase inhibitor cocktail 2 (100 μL per 10 mL of buffer, added freshly)) for 1 h on ice. In the case that cells were not analyzed immediately after harvesting, cell pellets were flash frozen in liquid nitrogen (−196° C.), stored at −80° C. and lysed right after thawing. In the next step, the protein concentration was determined by Bradford assay[78] for all lysates. Sample buffer according to Lämmli was added in a proportion of 1:1 (v/v) and the lysates were heated to 95° C. for 5 minutes. The proteins (40 μg) were separated by SDS-polyacrylamide gel electrophoresis (SDS-PAGE) and blotted with a Mini-Protean Tetra Handcast System (Bio-Rad, Munich, Germany). A 10% polyacrylamide (Rotiphorese NF-Acrylamide/Bis Solution 30%, Carl Roth, Germany) gel was used to analyze HDAC6, acetylated α-tubulin and a 12.5% polyacrylamide gel was used for ac-H$_3$. HSP90 served as loading control. The proteins were blotted on an Immobilon-P Transfer Membrane (Merck Millipore, Darmstadt, Germany, CAT #: IPVH00010). The membranes were washed three times with TRIS buffered saline containing Tween 20 (TBST-T; 20 mM Tris, 140 mM NaCl, 0.05% Tween 20) for at least 5 minutes. After blocking with 5% dry milk in TBS-T for 1 h under shaking, the membranes were washed again as mentioned before. The membranes were incubated with the primary antibodies diluted 1:1000 in 2% dry milk in TBS-T overnight: HDAC6 (160 kDa, monoclonal rabbit antibody, D2E5, Cell signaling, Germany, CAT #: 7558S), HSP90 (90 kDa, monoclonal mouse antibody, AC88, Enzo Life Science, Germany, CAT #: ADI-SPA-830), acetylated α-tubulin (55 kDa, monoclonal mouse antibody, Sigma Aldrich, Germany, CAT #: T7451), acetylated Histone H$_3$ (15 kDa, monoclonal rabbit antibody, Merck Millipore, CAT #: 06-599). Membranes were washed again with TBS-T and then incubated for 2 h with the secondary antibody diluted 1:10000 in 2% dry milk in TBS-T. HDAC6 and ac-H$_3$ membranes were incubated with Licor IRDye 800 CW donkey fluorescence anti-rabbit IgG (H+L) antibody (LiCor Biosciences, Germany, CAT #: 92532213). HSP90 and α-tubulin were incubated with Licor IRDye 800 CW donkey fluorescence anti-mouse IgG (H+L) antibody (CAT #: 92532212). Finally, the membranes were washed three times and were imaged with a LICOR Odyssey Imager (LI-COR, Lincoln, USA) and measured with ImageStudioLite (Version 5.2.5).

Example 5: Enhancement of Solubility

TABLE 2

Comparison of the solubility of compounds with and without a solubility improving Y—(CH$_2$)$_p$—Q— Part

| Compound | Y—(CH$_2$)$_p$—Q— Part | Solubility in H$_2$O |
|---|---|---|
| 21 | + | 200-1000 g/L |
| Marbostat-100 | − | <1 g/L |

REFERENCES 1. 1Brandl, A, T. Heinzel, et al. (2009). "Histone deacetylases: salesmen and customers in the post-translational modification market." *Biology of the Cell* 101(4): 193-205.
2. Beyer, M., N. Kiweler, et. al. (2017) "How to distinguish between the activity of HDAC1-3 and HDAC6 with western blot" in: HDAC HAT Funct. Assess. Inhib. Dev., Springer: pp. 355-364
3. Buchwald, M., K. Pietschmann, et al. (2010) "Ubiquitin conjugase UBCH8 targets active FMS-like tyrosine kinase 3 for proteasomal degradation" *Leukemia* 24: 1412-1421.
4. Buchwald, M., K. Pietschmann, et al. (2013) "SIAH ubiquitin ligases target the nonreceptor tyrosine kinase ACK1 for ubiquitinylation and proteasomal degradation" *Oncogene* 32: 4913-4920.
5. Buchwald, M., O. H. Krämer, et al. (2009). "HDACi—Targets beyond chromatin." *Cancer Letters* 280(2): 160-167.

6 Butler, K. V., J. Kalin, et al. (2010). "Rational design and simple chemistry yield a superior neuroprotective HDAC6 inhibitor, tubastatin A." *J. Am. Chem. Soc.* 132 (31): 10842-10846.

7 Chou, C. J., E. S. Inks, et al. (2012). *Unique HDAC6 inhibitors targeting Hsp90 complexes.* 243rd ACS National Meeting & Exposition, San Diego, Calif., United States.

8 Choudhary, C., C. Kumar, et al. (2009). "Lysine Acetylation Targets Protein Complexes and Co-Regulates Major Cellular Functions." *Science* 325(5942): 834-840.

9 Lee, Y.-S., K.-H. Lim, et al. (2008). "The Cytoplasmic Deacetylase HDAC6 Is Required for Efficient Oncogenic Tumorigenesis." *Cancer Res.* 68 (Copyright (C) 2013 American Chemical Society (ACS). All Rights Reserved.): 7561-7569.

10 Mahboobi, S., A. Sellmer, et al. (2016). Preparation of fused heterocyclic compounds as HDAC6 inhibitors and their uses, Universität Regensburg, Germany; Friedrich-Schiller-Universitaet Jena; Universitaetsklinikum Jena. 257 pp.

11 Mahboobi, S., S. Teller, et al. (2002). "Bis(1H-2-indolyl) methanones as a Novel Class of Inhibitors of the Platelet-Derived Growth Factor Receptor Kinase." *Journal of Medicinal Chemistry* 45(5): 1002-1018.

12 Müller, S. and O. H. Krämer (2010). "Inhibitors of HDACs—Effective Drugs Against Cancer?" *Current Cancer Drug Targets* 10(2): 210-228.

13 Pandey, U. B., Z. Nie, et al. (2007). "HDAC6 rescues neurodegeneration and provides an essential link between autophagy and the UPS." *Nature* 447(7146): 860-864.

14 Quintas-Cardama, A., F. P. S. Santos, et al. (2011). "Histone deacetylase inhibitors for the treatment of myelodysplastic syndrome and acute myeloid leukemia." *Leukemia* 25: 226-235.

15 Schneider, G., O. H. Krämer, et al. (2010). "Targeting histone deacetylases in pancreatic ductal adenocarcinoma." *Journal of Cellular and Molecular Medicine* 14(6a): 1255-1263.

16 Scott, G. K., C. Marx, et al. (2008). "Destabilization of ERBB2 Transcripts by Targeting 3 Untranslated Region Messenger RNA Associated HuR and Histone Deacetylase-6." *Mol Cancer Res* 6: 1250-1258.

17 Sellmer, A., H. Stangl, et al. (2018). "Marbostat-100 Defines a New Class of Potent and Selective Antiinflammatory and Antirheumatic Histone Deacetylase 6 Inhibitors." *Journal of Medicinal Chemistry.*

18 Spange, S., T. Wagner, et al. (2009). "Acetylation of non-histone proteins modulates cellular signalling at multiple levels." *The International Journal of Biochemistry & Cell Biology* 41(1): 185-198.

19 Yang, W.-L., C.-Y. Li, et al. (2016). "Cu(I)—Catalyzed Chemoselective and Stereoselective [3+3] Cycloaddition of Azomethine Ylides with 2-Indolylnitroethylenes: Facile Access to Highly Substituted Tetrahydro-γ-Carbolines." *ACS Catal.* 6(9): 5685-5690.

The invention claimed is:

1. A compound having the general formula I $$Y\text{—}[CH_2]_p\text{-}Q\text{-}H\text{-}L\text{-}(HAm) \quad \text{(formula I)}$$

wherein H is

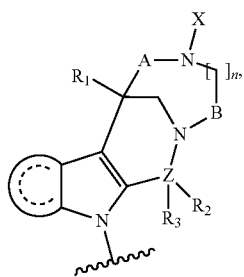

(head group 1)

wherein L is a linker having the formula

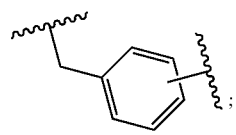

wherein (HAm) is hydroxamic acid with the formula

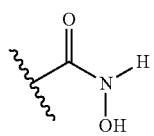 [SMILES: *C(=O)NO]

or a carbamate-protected hydroxyamic acid;

wherein A is $CH_2$, C=O or C=S;

B is $CH_2$, C=O or C=S;

n is 0 or 1;

p is 0 to 6;

Q is selected from —$CH_2$—, O, NH, alkylamino, an ester, and an amide-group;

$R_1$ to $R_3$ are each independently selected from the group consisting of hydrogen, branched or unbranched alkyl selected from $C_1$ to $C_6$, and aryl;

X is a branched or unbranched alkyl selected from $C_1$ to $C_6$;

Y is selected from the group consisting of amino; cyclic alkylamino; dialkylamino; cyclic diaminoalkyl; heterocyclic alkylamino; amino acid substituents connected either via their α-amino group or their carboxy group; and pharmaceutically acceptable salts thereof;

Z is carbon, nitrogen or oxygen; with the proviso that when Z is nitrogen, only one of R2 and R3 is present, and when Z is oxygen, neither of R2 and R3 is present; and wherein the symbol

represents a five or six membered aromatic or heteroaromatic ring system;

and wherein Q is connected to said head group H at said

or a pharmaceutically acceptable salt thereof.

2. The compound of claim 1, wherein at least one of A and B is C=O.

3. The compound according to claim 1, wherein n is 0.

4. The compound according to claim 1, wherein Q is O and p is 2.

5. The compound according to claim 1, wherein Y is selected from the group consisting of amino, cyclic alkylamino, dialkylamino, cyclic diaminoalkyl, and heterocyclic alkylamino.

6. The compound according to claim 1, wherein the hydroxyamic acid (HAm) is protected by a carbamate, such that the hydroxamic acid is represented by the formula

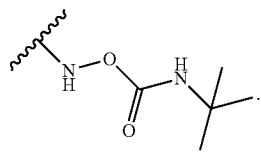 [SMILES: *NOC(=O)NC(C)(C)C]

7. The compound according to claim 1, wherein said compound is selected from the group consisting of:

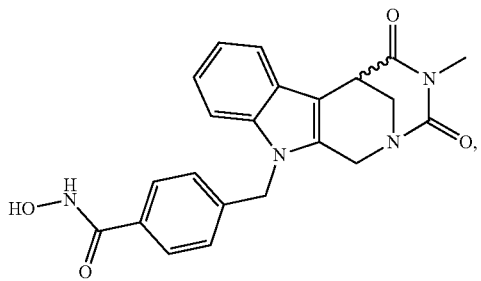

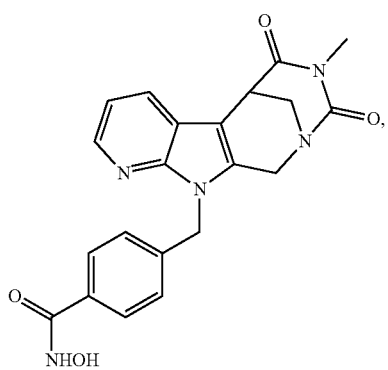

-continued

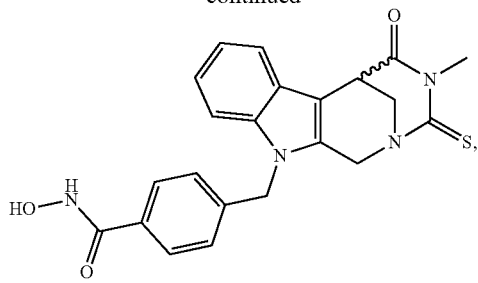

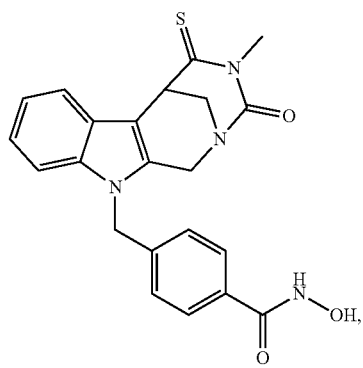

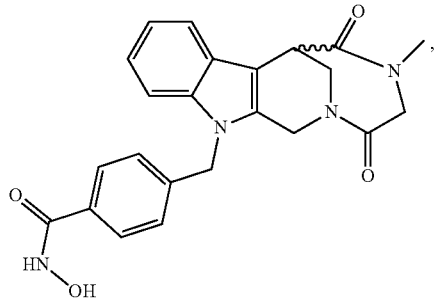

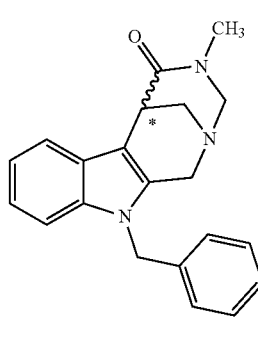

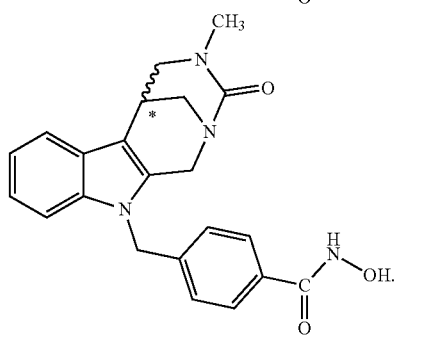

8. The compound according to claim 1, wherein said compound is selected from

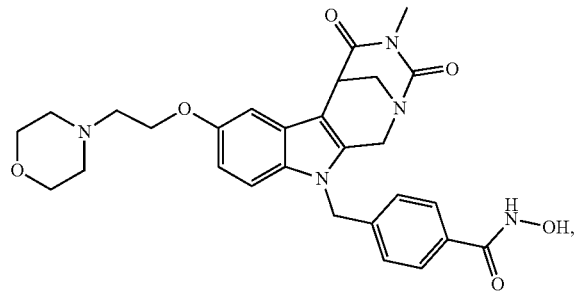

21

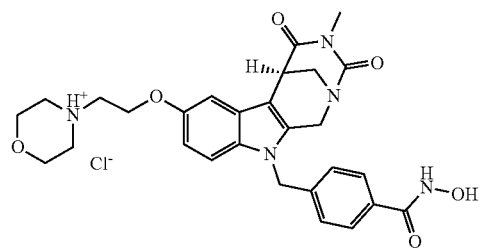

R-21

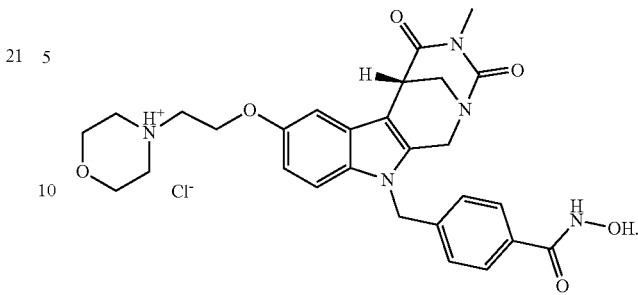

S-21

9. A pharmaceutical composition comprising
(a) at least one compound, or a pharmaceutically acceptable salt thereof, according to claim 1,
(b) optionally, one or more further agent(s) or drug(s), and
(c) optionally, one or more pharmaceutically acceptable excipient(s) and/or carrier(s).

10. A method for treating acute myeloid leukemia (AML); wherein said method comprises administering, to a subject in need of such treatment, a compound of claim 1.

11. The method according to claim 10, wherein such treatment is in combination with one or more further agent(s) or drug(s) selected from tyrosine kinase inhibitor(s) and proteasome inhibitor(s),
and/or wherein such treatment is in combination with a therapy comprising sensitizing AML cells.

12. The compound, according to claim 1, wherein Y is selected from 1-methylpiperazinyl and morpholinyl.

13. The pharmaceutical composition, according to claim 9, further comprising a tyrosine kinase inhibitor and/or a proteasome inhibitor.

14. The method according to claim 10, wherein the therapy comprising sensitizing AML cells is a radiation therapy.

* * * * *